United States Patent
Shailubhai

(10) Patent No.: US 10,758,541 B2
(45) Date of Patent: Sep. 1, 2020

(54) FORMULATIONS OF MILCICLIB AND THERAPEUTIC COMBINATIONS OF THE SAME FOR USE IN THE TREATMENT OF CANCER

(71) Applicant: Tiziana Life Sciences PLC, London (GB)

(72) Inventor: Kunwar Shailubhai, Line Lexington, PA (US)

(73) Assignee: Tiziana Life Sciences PLC, London (GB)

(*) Notice: Subject to any disclaimer, the term of this patent is extended or adjusted under 35 U.S.C. 154(b) by 0 days.

(21) Appl. No.: 16/182,036

(22) Filed: Nov. 6, 2018

(65) Prior Publication Data
US 2019/0134044 A1 May 9, 2019

Related U.S. Application Data

(60) Provisional application No. 62/582,288, filed on Nov. 6, 2017.

(51) Int. Cl.
| | |
|---|---|
| *A61K 31/519* | (2006.01) |
| *A61K 31/4412* | (2006.01) |
| *A61K 31/47* | (2006.01) |
| *A61K 9/00* | (2006.01) |
| *A61P 35/00* | (2006.01) |
| *A61K 31/404* | (2006.01) |
| *A61K 9/20* | (2006.01) |
| *A61K 9/48* | (2006.01) |

(52) U.S. Cl.
CPC .......... *A61K 31/519* (2013.01); *A61K 9/0053* (2013.01); *A61K 31/404* (2013.01); *A61K 31/4412* (2013.01); *A61K 31/47* (2013.01); *A61P 35/00* (2018.01); *A61K 9/20* (2013.01); *A61K 9/48* (2013.01); *A61K 2300/00* (2013.01)

(58) Field of Classification Search
CPC .. A61K 31/519; A61K 31/4412; A61K 31/47; A61K 9/00
See application file for complete search history.

(56) References Cited

U.S. PATENT DOCUMENTS 4,522,811 A 6/1985 Eppstein et al.

FOREIGN PATENT DOCUMENTS

| WO | WO 2007/090794 A1 | 8/2007 |
| WO | WO 2010/012777 A1 | 2/2010 |
| WO | WO 2016/015605 A1 | 2/2016 |
| WO | WO 2016/100882 A1 | 6/2016 |

OTHER PUBLICATIONS

Sacco et al. BMC Gastroenterology, 2011, vol. 11, No. 4, pp. 1-6.*
Albanese, C. et al. "Dual Targeting of CDK and Tropomyosin Receptor Kinase Families by the Oral Inhibitor PHA-848125, an Agent with Broad-Spectrum Antitumor Efficacy", Molecular Cancer Therapeutics, 2010, vol. 9, p. 2243-2254.
Choudhari, S. R. et al. "Deactivation of Akt and STAT3 signaling promotes apoptosis, inhibits proliferation, and enhances the sensitivity of hepatocellular carcinoma cells to an anticancer agent, Atiprimod", Molecular Cancer Therapeutics, 2007, vol. 6, No. 1, p. 112-121.
Ito, H. et al. "Ketamine Causes Mitochondrial Dysfunction in Human Induced Pluripotent Stem Cell-Derived Neurons", PLoS One, 2015, 10(5): e0128445, 20 pages.
Law, M. E. et al. "Cyclin-Dependent Kinase Inhibitors as Anticancer Therapeutics", Molecular Pharmacology, 2015, vol. 88, p. 846-852.
Park, J-K. et al. "miR-221 Silencing blocks hepatocellular carcinoma and promotes survival", Cancer Research, 2011, vol. 71, No. 24, p. 7608-7616.
Saxena, N. K. et al. "Concomitant Activation of the JAK/STAT, PI3K/AKT, and ERK Signaling Is Involved in Leptin-Mediated Promotion of Invasion and Migration of Hepatocellular Carcinoma Cells", Cancer Research, 2007, vol. 67, No. 6, p. 2497-2507.
Shailubhai, K. et al. "Atiprimod is an inhibitor of cancer cell proliferation and angiogenesis", Journal of Experimental Therapeutics and Oncology, 2004, vol. 4, p. 267-279.
Weiss, G. J. et al. "Phase I dose-escalation study to examine the safety and tolerability of LY2603618, a checkpoint 1 kinase inhibitor, administered 1 day after pemetrexed 500 mg/m² every 21 days in patients with cancer", Invest New Drugs, 2013, vol. 31, p. 136-144.
Abou-Alfa, G.K., et al., "Cabozantinib in Patients with Advanced and Progressing Hepatocellular Carcinoma" N Engl J Med, 2018, 379(1), p. 54-63.
Albanese, C., et al., "Anti-tumour efficacy on glioma models of PHA-848125, a multi-kinase inhibitor able to cross the blood-brain barrier" Br J Pharmacol, 2013, 169(1), p. 156-166.
Aspeslagh, S., et al., "Phase I dose-escalation study of milciclib in combination with gemcitabine in patients with refractory solid tumors", Cancer Chemother Pharmacol, 2017, 79(6), p. 1257-1265.
Besse, B., et al., "Efficacy of milciclib (PHA-848125AC), a pan-cyclin d-dependent kinase inhibitor, in two phase II studies with thymic carcinoma (TC) and B3 thymoma (B3T) patients", Journal of Clinical Oncology, 2018, 36(15 suppl), p. 8519.
Boland, P. and Wu, J., "Systemic therapy for hepatocellular carcinoma: beyond sorafenib", Chin Clin Oncol, 2018, 7(5), p. 50-55.
Callegari, E., et al., "Liver tumorigenicity promoted by microRNA-221 in a mouse transgenic model", Hepatology, 2012, 56(3), p. 1025-1033.

(Continued)

*Primary Examiner* — Samira J Jean-Louis
(74) *Attorney, Agent, or Firm* — Cooley LLP; Ivor R. Elrifi; Thomas J. Paxton

(57) ABSTRACT

This application relates to methods of treating and/or preventing cancer (e.g., non-small cell lung cancer, renal cell carcinoma, hepatocellular carcinoma, thyroid carcinoma, colorectal cancer, gastrointestinal stromal tumors, breast cancer, prostate cancer, pancreatic cancer, or thymoma) in patients in need thereof comprising administering to the patient a therapeutically effective amount of a CDK inhibitor (e.g., milciclib) in combination with a therapeutically effective amount of another anticancer drug (e.g., sorafenib, lenvatinib, regorafenib, sunitinib, nivolumab, gemcitabine, and palbociclib).

30 Claims, 57 Drawing Sheets
(53 of 57 Drawing Sheet(s) Filed in Color)

(56) References Cited

OTHER PUBLICATIONS

Chang, T.M., et al., "The regulatory role of aberrant Phosphatase and Tensin Homologue and Liver Kinase B1 on AKT/mTOR/c-Myc axis in pancreatic neuroendocrine tumors", Oncotarget, 2017, 8(58), p. 98068-98083.
Chiang, D.Y., et al., "Focal gains of VEGFA and molecular classification of hepatocellular carcinoma", Cancer Res, 2008, 68(16), p. 6779-6788.
Degrassi, A., et al., "Efficacy of PHA-848125, a cyclin-dependent kinase inhibitor, on the K-Ras$^{G12D}$LA2 lung adenocarcinoma transgenic mouse model: evaluation by multimodality imaging", Mol Cancer Ther, 2010, 9(3), p. 673-681.
Di Martino, M.T., et al., "In vitro and in vivo anti-tumor activity of miR-221/222 inhibitors in multiple myeloma", Oncotarget, 2013, 4(2), p. 242-255.
Fornari, F., et al., "MiR-221 controls CDKN1C/p57 and CDKN1B/p27 expression in human hepatocellular carcinoma", Oncogene, 2008, 27(43), p. 5651-61.
Fornari, F., et al., "In Hepatocellular Carcinoma miR-221 Modulates Sorafenib Resistance through Inhibition of Caspase-3-Mediated Apoptosis", Clin Cancer Res, 2017, 23(14), p. 3953-3965.
Forner, A., et al., "Hepatocellular carcinoma", Lancet, 2018, 14 pages.
Galardi, S., et al., "miR-221 and miR-222 expression affects the proliferation potential of human prostate carcinoma cell lines by targeting p27$^{Kip1}$", J Biol Chem, 2007, 282(32), p. 23716-24.
Gao, J.J., et al., "Sorafenib-based combined molecule targeting in treatment of hepatocellular carcinoma", World J Gastroenterol, 2015, 21(42), p. 12059-12070.
Gao, Y.S., et al., "Nude mice model of human hepatocellular carcinoma via orthotopic implantation of histologically intact tissue", World J Gastroenterol, 2004, 10(21), p. 3107-3111.
Gedaly, R., et al., "PKI-587 and sorafenib targeting PI3K/AKT/mTOR and Ras/Raf/MAPK pathways synergistically inhibit HCC cell proliferation", J Surg Res, 2012, 176(2), p. 542-548.
Gill, R.M., et al., "Regulation of expression and activity of distinct pRB, E2F, D-type cyclin, and CKI family members during terminal differentiation of P19 cells", Exp Cell Res, 1998, 244(1), p. 157-70.
Gramantieri, L., et al., "MicroRNA involvement in hepatocellular carcinoma", J Cell Mol Med, 2008, 12(6A), p. 2189-204.
He, L., et al., "Mouse models of liver cancer: Progress and recommendations", Oncotarget, 2015, 6(27), p. 23306-22.
He, A.R. and Goldenberg, A.S., "Treating hepatocellular carcinoma progression following first-line sorafenib: therapeutic options and clinical observations" Therap Adv Gastroenterol, 2013, 6(6), p. 447-58.
Hemming, A.W., et al., "Hepatitis B and Hepatocellular Carcinoma", Clin Liver Dis, 2016, 20(4), p. 703-720.
Henley, S.A. and Dick, F.A., "The retinoblastoma family of proteins and their regulatory functions in the mammalian cell division cycle", Cell Division, 2012, 7(1), p. 10. (14 pages).
Heo, Y.A. and Syed, Y.Y., "Regorafenib: A Review in Hepatocellular Carcinoma", Drugs, (2018) 78:951-958.
Heron-Milhavet, L., et al., "Only Akt1 is required for proliferation, while Akt2 promotes cell cycle exit through p21 binding", Mol Cell Biol, 2006, 26(22), p. 8267-8280.
Jindal, A., et al., "Oral Treatment with Milciclib Either Alone or in Combination with Sorafenib Inhibited Tumor Growth in an Orthotopic Model of Hepatocellular Carcinoma", Hepatology, 2018, 68(1 (Supplement)), p. 879A.
Jindal, A., et al., "Hepatocellular Carcinoma: Etiology and Current and Future Drugs", J Clin Exp Hepatol, 2019, 9(2), p. 221-232.

Kudo, M., et al., "Lenvatinib versus sorafenib in first-line treatment of patients with unresectable hepatocellular carcinoma: a randomised phase 3 non-inferiority trial", Lancet, 2018, 391, p. 1163-1173.
Le Sage, C., et al., "Regulation of the p27$^{Kip1}$ tumor suppressor by miR-221 and miR-222 promotes cancer cell proliferation", EMBO J, 2007, 26(15), p. 3699-708.
Li, Y., et al., "Establishment of cell clones with different metastatic potential from the metastatic hepatocellular carcinoma cell line MHCC97", World J Gastroenterol, 2001, 7(5), p. 630-636.
Llovet, J.M., et al., "Molecular therapies and precision medicine for hepatocellular carcinoma", Nat Rev Clin Oncol, 2018, 15(10), p. 599-616.
Llovet, J.M. and Bruix, J., "Molecular targeted therapies in hepatocellular carcinoma", Hepatology, 2008, 48(4), p. 1312-27.
Lu, C., et al., "Expression of Wnt3a in hepatocellular carcinoma and its effects on cell cycle and metastasis", Int J Oncol, 2017, 51(4), p. 1135-1145.
Lurje, I., et al., "Treatment Strategies for Hepatocellular Carcinoma—a Multidisciplinary Approach", Int J Mol Sci, 2019, 20(6), 27 pages.
MacLachlan, T.K., et al., "Cyclins, cyclin-dependent kinases and cdk inhibitors: implications in cell cycle control and cancer", Crit Rev Eukaryot Gene Expr, 1995, 5(2), p. 127-56.
Moshiri, F., et al., "Inhibiting the oncogenic mir-221 by microRNA sponge: toward microRNA-based therapeutics for hepatocellular carcinoma", Gastroenterol Hepatol Bed Bench, 2014, 7(1), p. 43-54.
Newell, P., et al., "Ras pathway activation in hepatocellular carcinoma and anti-tumoral effect of combined sorafenib and rapamycin in vivo", J Hepatol, 2009, 51(4), p. 725-33.
Pelosof, L., et al., "Benefit-Risk Summary of Regorafenib for the Treatment of Patients with Advanced Hepatocellular Carcinoma That Has Progressed on Sorafenib", Oncologist, 2018, 23(4), p. 496-500.
Personeni, N. et al., "Lenvatinib for the treatment of unresectable hepatocellular carcinoma: evidence to date", J Hepatocell Carcinoma, 2019, 6, p. 31-39.
Peyressatre, M., et al., "Targeting cyclin-dependent kinases in human cancers: from small molecules to Peptide inhibitors", Cancers (Basel), 2015, 7(1), p. 179-237.
Pineau, P., et al., "miR-221 overexpression contributes to liver tumorigenesis", Proc Natl Acad Sci USA, 2010, 107(1), p. 264-9.
Pinter, M. and Peck-Radosavljevic, M. "Review article: systemic treatment of hepatocellular carcinoma", Aliment Pharmacol Ther, 2018, 12 pages.
Prieto-Dominguez, N., et al., "Modulation of Autophagy by Sorafenib: Effects on Treatment Response", Front Pharmacol, 2016, 7, Article 151, 16 pages.
Shamloo, B. and Usluer, S. "p21 in Cancer Research" Cancers (Basel), 2019, 11(8), 19 pages.
Szymonowicz, K., et al., "New Insights into Protein Kinase B/Akt Signaling: Role of Localized Akt Activation and Compartment-Specific Target Proteins for the Cellular Radiation Response", Cancers (Basel), 2018, 10(3), 33 pages.
Xu, X., et al., "The Role of MicroRNAs in Hepatocellular Carcinoma", J Cancer, 2018, 9(19), p. 3557-3569.
Zhou, K. and Fountzilas, C. "Outcomes and Quality of Life of Systemic Therapy in Advanced Hepatocellular Carcinoma", Cancers (Basel), 2019, 11(6), 17 pages.
Zhu, Y.J., et al., "New knowledge of the mechanisms of sorafenib resistance in liver cancer", Acta Pharmacol Sin, 2017, 38(5), p. 614-622.
Wang, Y., et al., "miR-221 Mediates Chemoresistance of Esophageal Adenocarcinoma by Direct Targeting of DKK2 Expression", Ann Surg, 2016, 264(5), p. 804-814.
Wu, X., et al., "Application of PD-1 Blockade in Cancer Immunotherapy", Comput Struct Biotechnol J, 2019, 17, p. 661-674.

* cited by examiner

IC$_{50}$ Values of Milciclib in MHCC97H

IC$_{50}$ Values of Milciclib in MHCC97L

IC$_{50}$ Values of Milciclib HepG2.2.15

MHCC97H

MHCC97H

MHCC97H

MHCC97H

MHCC97H

MHCC97-low

MHCC97-low

MHCC97-low

MHCC97-low

MHCC97-low

MHCC97L

MHCC97L

MHCC97L

MHCC97L

MHCC97L

IC$_{50}$ Value of Sunitinib – HepG2.2.15

IC$_{50}$ Value of Sorafenib – HepG2.2.15

IC$_{50}$ Value of Regorafenib – HepG2.2.15

IC$_{50}$ Value of Lenvatinib – HepG2.2.15

IC$_{50}$ Value of Palbociclib – HepG2.2.15

HepG2.2.15

HepG2.2.15

HepG2.2.15

HepG2.2.15

Promega Triplex Assay – TKIs and CDKIs on MHCC97h cell line
Viability, Cytotoxicity and Apoptosis (Caspase 3/7)
$IC_{50}$: 1.3 μm Promega Triplex Assay – TKIs and CDKIs on MHCC97h cell line
Viability, Cytotoxicity and Apoptosis (Caspase 3/7)
$IC_{50}$: 12 μm Promega Triplex Assay – TKIs and CDKIs on MHCC97h cell line
Viability, Cytotoxicity and Apoptosis (Caspase 3/7)
$IC_{50}$: 4.7 μm Promega Triplex Assay – TKIs and CDKIs on MHCC97h cell line
Viability, Cytotoxicity and Apoptosis (Caspase 3/7)
$IC_{50}$: 30.4 μm Promega Triplex Assay – TKIs and CDKIs on MHCC97h cell line
Viability, Cytotoxicity and Apoptosis (Caspase 3/7)
IC$_{50}$: 0.28 μm Promega Triplex Assay – Milciclib combination with MHCC97H cell line
Viability, Cytotoxicity and Apoptosis (Caspase 3/7)
IC$_{50}$: 6.7 μm Promega Triplex Assay – Milciclib combination with MHCC97H cell line
Viability, Cytotoxicity and Apoptosis (Caspase 3/7)
IC$_{50}$: 1.9 μm Promega Triplex Assay – Milciclib combination with MHCC97H cell line
Viability, Cytotoxicity and Apoptosis (Caspase 3/7)
IC$_{50}$: 0.12 μm Promega Triplex Assay – Milciclib combination with MHCC97H cell line
Viability, Cytotoxicity and Apoptosis (Caspase 3/7)
IC$_{50}$: 17.2 μm

MHCC97L
Promega Triplex Assay –
Viability, Cytotoxicity and Apoptosis (Caspase 3/7)
Milciclib (IC$_{50}$: 0.91 μm)

MHCC97L
Promega Triplex Assay –
Viability, Cytotoxicity and Apoptosis (Caspase 3/7)
Regorafenib ($IC_{50}$: 3.20 μm)

MHCC97L
Promega Triplex Assay –
Viability, Cytotoxicity and Apoptosis (Caspase 3/7)
Sunitinib ($IC_{50}$: 3.2 μm)

MHCC97L
Promega Triplex Assay –
Viability, Cytotoxicity and Apoptosis (Caspase 3/7)
Sorafenib (IC$_{50}$: 8.6 µm)

Promega Triplex Assay –
Viability, Cytotoxicity and Apoptosis (Caspase 3/7)
Lenvatinib (IC$_{50}$: 0.18 µm)

Promega Triplex Assay –
Viability, Cytotoxicity and Apoptosis (Caspase 3/7)
Palbociclib (IC$_{50}$: 8.44 μm)

Promega Triplex Assay – Milciclib combination with MHCC97L cell line
Viability, Cytotoxicity and Apoptosis (Caspase 3/7)
IC50: 3.18 μM Promega Triplex Assay – Milciclib combination with MHCC97L cell line
Viability, Cytotoxicity and Apoptosis (Caspase 3/7)
IC50: 1.6 µM Promega Triplex Assay – Milciclib combination with MHCC97L cell line
Viability, Cytotoxicity and Apoptosis (Caspase 3/7)
IC50: 3.99 µM Promega Triplex Assay – Milciclib combination with MHCC97L cell line
Viability, Cytotoxicity and Apoptosis (Caspase 3/7)
IC50: 0.08 μM Promega Triplex Assay – Milciclib combination with MHCC97L cell line
Viability, Cytotoxicity and Apoptosis (Caspase 3/7)
IC50: 3.94 μM MHCC97h cell line
Wound Healing Assay - milciclib MHCC97h cell line
Wound Healing Assay – sorafenib and milciclib
(V = vehicle, S = sorafenib (12 μm), + = sorafenib (6 μm) + milciclib (1 μm))

MHCC97h cell line
Wound Healing Assay – sunitinib and milciclib
(V = vehicle, S = sunitinib (30 μm), + = sunitinib (17 μm) + milciclib (1 μm))

MHCC97h cell line
Wound Healing Assay – lenvatinib and milciclib
(V = vehicle, L = lenvatinib (0.24 μm), + = lenvatinib (0.12 μm) + milciclib (1 μm))

MHCC97h cell line
Wound Healing Assay – regorafenib and milciclib
(V = vehicle, R = regorafenib (4.7 μm), + = regorafenib (2 μm) + milciclib (1 μm))

Wound Healing Assay – milciclib
MHCC97L cell line

MHCC97L cell line
Wound Healing Assay – sorafenib and milciclib
(V = vehicle, S = sorafenib (8.8 μm), + = sorafenib (8.8 μm) + milciclib (1 μm))

MHCC97L cell line
Wound Healing Assay – regorafenib and milciclib
(V = vehicle, R = regorafenib (3.5 μm), + = regorafenib (3.5 μm) + milciclib (1 μm))

MHCC97L cell line
Wound Healing Assay – sunitinib and milciclib
(V = vehicle, S = sunitinib (8.2 μm), + = sunitinib (8.2 μm) + milciclib (1 μm))

MHCC97L cell line
Wound Healing Assay – lenvatenib and milciclib
(V = vehicle, L = lenvatenib (0.14 μm), + = lenvatenib (0.14 μm) + milciclib (1 μm))

HepG2.2.15 Wound Healing Assay - Milciclib
(V = vehicle, M = milciclib (1 μm))

HepG2.2.15 Wound Healing Assay – Sorafenib and Milciclib
(V = vehicle, S = sorafenib (12 μm), + = sorafenib (6 μm) + milciclib (1 μm))

HepG2.2.15 Wound Healing Assay – Regorafenib and Milciclib
(V = vehicle, S = regorafenib (4.7 μm), + = regorafenib (2 μm) + milciclib (1 μm))

P value: *P<0.001, P<0.01, *P<0.05

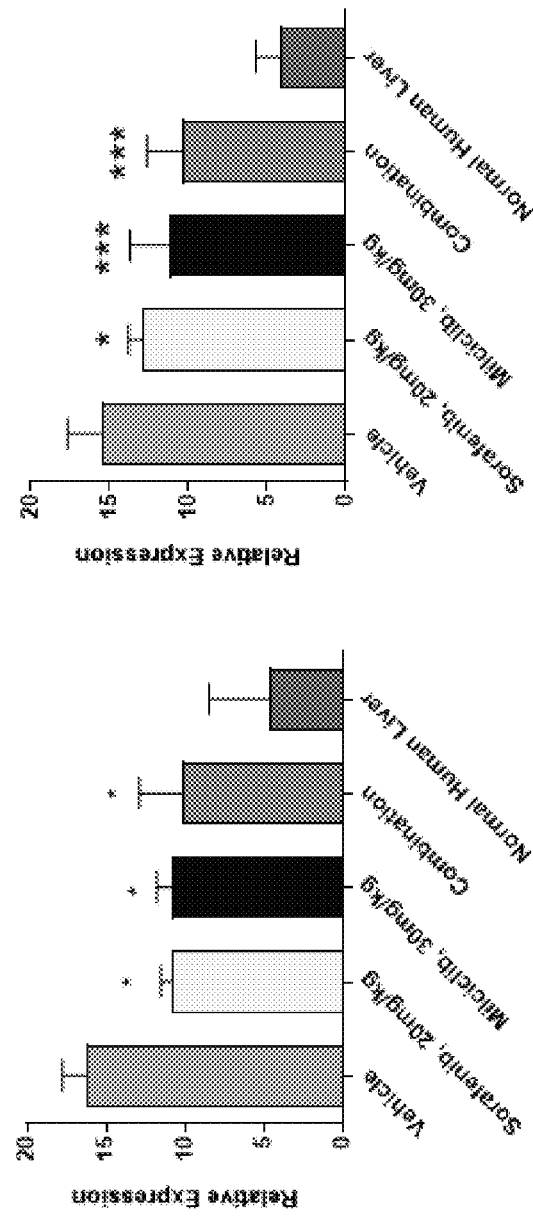
FIGURE 74A
FIGURE 74B
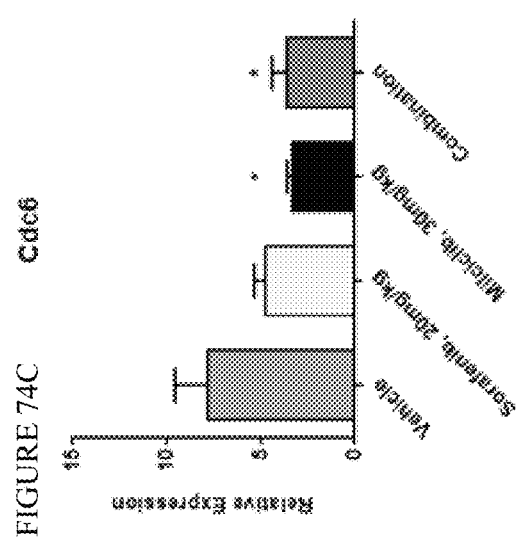
FIGURE 74C

FORMULATIONS OF MILCICLIB AND THERAPEUTIC COMBINATIONS OF THE SAME FOR USE IN THE TREATMENT OF CANCER

RELATED APPLICATIONS

This application claims the benefit of, and priority to, U.S. Provisional Application No. 62/582,288, filed Nov. 6, 2017, which is incorporated by reference herein in its entirety for all purposes.

TECHNICAL FIELD

This application relates generally to the treatment of cancers, and more particularly relates to the treatment of cancers with a combination of a cyclin-dependent kinase (CDK) inhibitor and at least one additional anticancer drug. The invention finds utility in the fields of medicine and pharmacotherapy.

BACKGROUND

Milciclib, which may be referred herein to as Compound 1, or N,1,4,4-tetramethyl-8-((4-(4-methylpiperazin-1-yl)phenyl)amino)-4,5-dihydro-1H-pyrazolo[4,3-h]quinazoline-3-carboxamide, has the following structure:

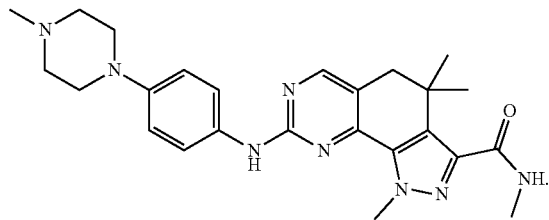 [SMILES: CNC(=O)c1nn(C)c2c1C(C)(C)Cc1cnc(Nc3ccc(N4CCN(C)CC4)cc3)nc1-2]

Milciclib is a small molecule inhibitor of multiple CDKs, including CDK1, CDK2, CDK4, CDK5, CDK7, and CDK9, and TRKs (TPKA and TRKC), has shown efficacy in several preclinical tumor models (Albanese C et al. (2010) *Mol Cancer Ther* 9:2243-2254.). In a phase I study, oral treatment with milciclib was found to be well-tolerated and the drug showed promising clinical responses in patients with advanced solid malignancies such as in thymic carcinoma, pancreatic carcinoma and colon cancer (Weiss G J et al. (2013) *Invest New Drugs* 31:136-144.) The major toxicity profile consisted of tremors and gastrointestinal toxicity which was reversible upon treatment suspension. Results from this study recommended a RP2D of 150 mg/day.

Particularly, hepatocellular carcinoma (HCC) is an extremely complex multi-factorial condition associated with many confounding factors affecting disease course and patient prognosis. A broad range of mechanisms, including telomere dysfunction, activation of oncogenic pathways, abrogation of DNA damage checkpoints, activation of pro-inflammatory and metastatic pathways, and induction of the oxidative stress response. Thus, an effective therapy for HCC needs to control proliferation of hepatocytes and also suppress their metastatic potential. Milciclib, exhibiting broad-spectrum inhibitory activities against CDKs, effectively retards proliferation of cancer cells. Therefore, it is reasonable to propose that anticancer activity of milciclib may be potentiated by an inhibitor of tyrosine kinase to produce synergistic anti-tumorigenic activity.

There is a need for novel therapies by using milciclib in combination with a second anticancer drug or agent for the treatment of cancer. The present application addresses such a need.

SUMMARY OF THE INVENTION

In one aspect, this application pertains to a method of treating or preventing cancer in a patient in need thereof, comprising administering to the patient a therapeutically effective amount of a CDK inhibitor, or a pharmaceutically acceptable salt, isomer, or tautomer thereof, in combination with a therapeutically effective amount of another anticancer drug.

In one aspect, this application pertains to a method of treating or preventing cancer in a patient in need thereof, wherein the cancer is non-small cell lung cancer, renal cell carcinoma, hepatocellular carcinoma, thyroid carcinoma, melanoma, multiple myeloma, mantle cell lymphoma, non-Hodgkin's lymphoma, colorectal cancer, acute lymphocytic leukemia, chronic lymphocytic leukemia, chronic myelogenous leukemia, skin cancer, ovarian cancer, gastrointestinal stromal tumors, breast cancer, prostate cancer, pancreatic cancer, or thymoma.

In one aspect, this application pertains to a method of treating or preventing cancer in a patient in need thereof, wherein the CDK inhibitor is milciclib or a pharmaceutically acceptable salt thereof, and the other anticancer drug is sorafenib, lenvatinib, regorafenib, sunitinib, nivolumab, gemcitabine, palbociclib, afatinib, alectinib, axitinib, bortezomib, bosutinib, cabozantinib, carfilzomib, ceritinib, cobimetinib, crizotinib, dabrafenib, erlotinib, gefitinib, ibrutinib, idelalisib, imatinib, ixazomib, lapatinib, nilotinib, nintedanib, niraparib, osimertinib, pazopanib, pegaptanib, ponatinib, rucaparib, ruxolitinib, sonidegib, tofacitinib, trametinib, vandetanib, vemurafenib, vismodegibor, or a pharmaceutically acceptable salt thereof.

In one aspect, this application pertains to a method of treating or preventing cancer in a patient in need thereof, wherein the other anticancer drug is sorafenib or a pharmaceutically acceptable salt thereof.

In one aspect, this application pertains to a method wherein the therapeutically effective amount of sorafenib is 400 mg twice daily, 200 mg twice daily, or 200 mg once daily.

In one aspect, this application pertains to a method of treating or preventing cancer in a patient in need thereof, wherein the cancer is renal cell carcinoma, hepatocellular carcinoma, or thyroid carcinoma.

In one aspect, this application pertains to a method of treating or preventing cancer in a patient in need thereof, wherein the other anticancer drug is lenvatinib or a pharmaceutically acceptable salt thereof.

In one aspect, this application pertains to a method of treating or preventing cancer in a patient in need thereof, wherein the therapeutically effective amount of lenvatinib is 8, 10, 12, 14, 18, 20, 22, 24, 26, 28, 30, 32, or 34 mg once daily.

In one aspect, this application pertains to a method of treating or preventing cancer in a patient in need thereof, wherein the cancer is renal cell carcinoma or thyroid carcinoma.

In one aspect, this application pertains to a method of treating or preventing cancer in a patient in need thereof, wherein the other anticancer drug is regorafenib or a pharmaceutically acceptable salt thereof.

In one aspect, this application pertains to a method of treating or preventing cancer in a patient in need thereof, wherein the therapeutically effective amount of regorafenib is 80, 100, or 120 mg once daily for three weeks, followed by one week of no administration, wherein the cycle is optionally repeated.

In one aspect, this application pertains to a method of treating or preventing cancer in a patient in need thereof, wherein the cancer is colorectal cancer or gastrointestinal stromal tumors.

In one aspect, this application pertains to a method of treating or preventing cancer in a patient in need thereof, wherein the other anticancer drug is sunitinib or a pharmaceutically acceptable salt thereof.

In one aspect, this application pertains to a method of treating or preventing cancer in a patient in need thereof, wherein the therapeutically effective amount of sunitinib is 12.5, 25, 37.5, 50, 62.5, 75, 87.5, or 100 mg once daily continuously or for 4 weeks followed by two weeks of no administration, wherein the cycle is optionally repeated.

In one aspect, this application pertains to a method of treating or preventing cancer in a patient in need thereof, wherein the cancer is renal cell carcinoma or gastrointestinal stromal tumors.

In one aspect, this application pertains to a method of treating or preventing cancer in a patient in need thereof, wherein the other anticancer drug is nivolumab.

In one aspect, this application pertains to a method of treating or preventing cancer in a patient in need thereof, wherein the cancer is non-small cell lung cancer or renal cell carcinoma.

In one aspect, this application pertains to a method of treating or preventing cancer in a patient in need thereof, wherein the other anticancer drug is gemcitabine or a pharmaceutically acceptable salt thereof.

In one aspect, this application pertains to a method of treating or preventing cancer in a patient in need thereof, wherein the therapeutically effective amount of gemcitabine is 1000 mg/m$^2$ over 30 minutes once weekly for seven weeks, followed by one week of no administration, wherein the cycle is optionally repeated.

In one aspect, this application pertains to a method of treating or preventing cancer in a patient in need thereof, wherein the cancer is breast cancer.

In one aspect, this application pertains to a method of treating or preventing cancer in a patient in need thereof, wherein the other anticancer drug is palbociclib or a pharmaceutically acceptable salt thereof.

In one aspect, this application pertains to a method of treating or preventing cancer in a patient in need thereof, wherein the therapeutically effective amount of palbociclib is 75, 100, or 125 mg once daily for 3 weeks followed by one week of no administration, wherein the cycle is optionally repeated.

In one aspect, this application pertains to a method of treating or preventing cancer in a patient in need thereof, wherein the cancer is breast cancer.

In one aspect, this application pertains to a method of treating or preventing cancer in a patient in need thereof, wherein the therapeutically effective amount of milciclib is 50, 75, 100, 125, or 150 mg once daily for four consecutive days, followed by non-administration for 3 consecutive days, wherein the cycle is optionally repeated.

In one aspect, this application pertains to any of the methods described herein, wherein milciclib and the other anticancer drug are administered to the patient simultaneously.

In one aspect, this application pertains to any of the methods described herein, wherein milciclib and the other anticancer drug are administered in a single pharmaceutical formulation that further includes a pharmaceutically acceptable excipient.

In one aspect, this application pertains to any of the methods described herein, wherein the pharmaceutical formulation is in a controlled release form.

In one aspect, this application pertains to any of the methods described herein, wherein milciclib and the other anticancer drug are each administered in separate pharmaceutical formulations, wherein each formulation further includes a pharmaceutically acceptable excipient.

In one aspect, this application pertains to any of the methods described herein, wherein one or both of the pharmaceutical formulations is in a controlled release form.

In one aspect, this application pertains to any of the methods described herein, wherein milciclib and the other anticancer drug are administered to the patient sequentially.

In one aspect, this application pertains to any of the methods described herein, wherein administration of milciclib begins before administration of the other anticancer to the patient.

In one aspect, this application pertains to any of the methods described herein, wherein administration of milciclib begins after administration of the other anticancer to the patient.

In one aspect, this application pertains to any of the methods described herein, wherein milciclib is administered in a single pharmaceutical formulation that further includes a pharmaceutically acceptable excipient.

In one aspect, this application pertains to any of the methods described herein, wherein the pharmaceutical formulation is formulated for oral administration.

In one aspect, this application pertains to any of the methods described herein, wherein the pharmaceutical formulation is in the form of a tablet, pill, or capsule.

In one aspect, this application pertains to a method of treating or preventing renal cell carcinoma in a patient in need thereof comprising administering to the patient a therapeutically effective amount of milciclib, or a pharmaceutically acceptable salt, isomer, or tautomer thereof, in combination with a therapeutically effective amount of sorafenib, or a pharmaceutically acceptable salt, isomer, or tautomer thereof.

In one aspect, this application pertains to a method of treating or preventing hepatocellular carcinoma in a patient in need thereof comprising administering to the patient a therapeutically effective amount of milciclib, or a pharmaceutically acceptable salt, isomer, or tautomer thereof, in combination with a therapeutically effective amount of sorafenib, or a pharmaceutically acceptable salt, isomer, or tautomer thereof.

In one aspect, this application pertains to a method of treating or preventing thyroid carcinoma in a patient in need thereof comprising administering to the patient a therapeutically effective amount of milciclib, or a pharmaceutically acceptable salt, isomer, or tautomer thereof, in combination with a therapeutically effective amount of sorafenib, or a pharmaceutically acceptable salt, isomer, or tautomer thereof.

In one aspect, this application pertains to any of the methods described herein, wherein the therapeutically effective amount of sorafenib is 400 mg twice daily, 200 mg twice daily, or 200 mg once daily.

In one aspect, this application pertains to any of the methods described herein, wherein the therapeutically effective amount of milciclib is 50, 75, 100, 125, or 150 mg once daily for four consecutive days, followed by non-administration for 3 consecutive days, wherein the cycle is optionally repeated.

In one aspect, this application pertains to any of the methods described herein, wherein milciclib and sorafenib are administered to the patient simultaneously.

In one aspect, this application pertains to any of the methods described herein, wherein milciclib and sorafenib are administered in a single pharmaceutical formulation that further includes a pharmaceutically acceptable excipient.

In one aspect, this application pertains to any of the methods described herein, wherein the pharmaceutical formulation is in a controlled release form.

In one aspect, this application pertains to any of the methods described herein, wherein milciclib and sorafenib are administered in separate pharmaceutical formulations, wherein each formulation further includes a pharmaceutically acceptable excipient.

In one aspect, this application pertains to any of the methods described herein, wherein one or both of the pharmaceutical formulations is in a controlled release form.

In one aspect, this application pertains to any of the methods described herein, wherein milciclib and sorafenib are administered to the patient sequentially.

In one aspect, this application pertains to any of the methods described herein, wherein administration of milciclib begins before administration of sorafenib to the patient.

In one aspect, this application pertains to any of the methods described herein, wherein administration of milciclib begins after administration of sorafenib to the patient.

In one aspect, this application pertains to any of the methods described herein, wherein milciclib and sorafenib are each administered in separate pharmaceutical formulations that each further include a pharmaceutically acceptable excipient.

In one aspect, this application pertains to any of the methods described herein, wherein one or both pharmaceutical formulations are formulated for oral administration.

In one aspect, this application pertains to any of the methods described herein, wherein each pharmaceutical formulation is independently in the form of a tablet, pill, or capsule.

In one aspect, this application pertains to any of the methods described herein, wherein milciclib and sorafenib are administered in temporal proximity.

In one aspect, this application pertains to any of the methods described herein, wherein the CDK inhibitor and the other anticancer drug are administered in temporal proximity.

In one aspect, this application pertains to a pharmaceutical composition comprising milciclib or a pharmaceutically acceptable salt, isomer, or tautomer thereof, and another anticancer drug.

In one aspect, this application pertains to a pharmaceutical composition comprising milciclib or a pharmaceutically acceptable salt, isomer, or tautomer thereof, and another anticancer drug for use in the treatment or prevention of non-small cell lung cancer, renal cell carcinoma, hepatocellular carcinoma, thyroid carcinoma, melanoma, multiple myeloma, mantle cell lymphoma, non-Hodgkin's lymphoma, colorectal cancer, acute lymphocytic leukemia, chronic lymphocytic leukemia, chronic myelogenous leukemia, skin cancer, ovarian cancer, gastrointestinal stromal tumors, breast cancer, prostate cancer, pancreatic cancer, or thymoma.

In one aspect, this application pertains to the use of a pharmaceutical composition comprising milciclib or a pharmaceutically acceptable salt, isomer, or tautomer thereof, and another anticancer drug in the manufacture of a medicament for the treatment or prevention of non-small cell lung cancer, renal cell carcinoma, hepatocellular carcinoma, thyroid carcinoma, melanoma, multiple myeloma, mantle cell lymphoma, non-Hodgkin's lymphoma, colorectal cancer, acute lymphocytic leukemia, chronic lymphocytic leukemia, chronic myelogenous leukemia, skin cancer, ovarian cancer, gastrointestinal stromal tumors, breast cancer, prostate cancer, pancreatic cancer, or thymoma.

In one aspect, this application pertains to milciclib for use in the treatment or prevention of non-small cell lung cancer, renal cell carcinoma, hepatocellular carcinoma, thyroid carcinoma, melanoma, multiple myeloma, mantle cell lymphoma, non-Hodgkin's lymphoma, colorectal cancer, acute lymphocytic leukemia, chronic lymphocytic leukemia, chronic myelogenous leukemia, skin cancer, ovarian cancer, gastrointestinal stromal tumors, breast cancer, prostate cancer, pancreatic cancer, or thymoma, by co-administration with another anticancer drug.

In one aspect, this application pertains to sorafenib, lenvatinib, regorafenib, sunitinib, nivolumab, gemcitabine, palbociclib, afatinib, alectinib, axitinib, bortezomib, bosutinib, cabozantinib, carfilzomib, ceritinib, cobimetinib, crizotinib, dabrafenib, erlotinib, gefitinib, ibrutinib, idelalisib, imatinib, ixazomib, lapatinib, nilotinib, nintedanib, niraparib, osimertinib, pazopanib, pegaptanib, ponatinib, rucaparib, ruxolitinib, sonidegib, tofacitinib, trametinib, vandetanib, vemurafenib, vismodegibor, or a pharmaceutically acceptable salt thereof, for use in the treatment or prevention of non-small cell lung cancer, renal cell carcinoma, hepatocellular carcinoma, thyroid carcinoma, melanoma, multiple myeloma, mantle cell lymphoma, non-Hodgkin's lymphoma, colorectal cancer, acute lymphocytic leukemia, chronic lymphocytic leukemia, chronic myelogenous leukemia, skin cancer, ovarian cancer, gastrointestinal stromal tumors, breast cancer, prostate cancer, pancreatic cancer, or thymoma, by co-administration with milciclib.

In one aspect, this application pertains to the use of milciclib in the manufacture of a medicament for the treatment or prevention of non-small cell lung cancer, renal cell carcinoma, hepatocellular carcinoma, thyroid carcinoma, melanoma, multiple myeloma, mantle cell lymphoma, non-Hodgkin's lymphoma, colorectal cancer, acute lymphocytic leukemia, chronic lymphocytic leukemia, chronic myelogenous leukemia, skin cancer, ovarian cancer, gastrointestinal stromal tumors, breast cancer, prostate cancer, pancreatic cancer, or thymoma, by co-administration with another anticancer drug.

In one aspect, this application pertains to use of sorafenib, lenvatinib, regorafenib, sunitinib, nivolumab, gemcitabine, palbociclib, afatinib, alectinib, axitinib, bortezomib, bosutinib, cabozantinib, carfilzomib, ceritinib, cobimetinib, crizotinib, dabrafenib, erlotinib, gefitinib, ibrutinib, idelalisib, imatinib, ixazomib, lapatinib, nilotinib, nintedanib, niraparib, osimertinib, pazopanib, pegaptanib, ponatinib, rucaparib, ruxolitinib, sonidegib, tofacitinib, trametinib, vandetanib, vemurafenib, vismodegibor, or a pharmaceutically acceptable salt thereof, in the manufacture of a medicament for the treatment or prevention of non-small cell lung cancer, renal cell carcinoma, hepatocellular carcinoma, thyroid carcinoma, melanoma, multiple myeloma, mantle cell lymphoma, non-Hodgkin's lymphoma, colorectal cancer, acute lymphocytic leukemia, chronic lymphocytic leukemia, chronic myelogenous leukemia, skin cancer, ovarian cancer, gastrointestinal stromal tumors, breast cancer, prostate cancer, pancreatic cancer, or thymoma, by co-administration with milciclib.

In one aspect, this application pertains to a product comprising milciclib, or a pharmaceutically acceptable salt thereof, and sorafenib, lenvatinib, regorafenib, sunitinib, nivolumab, gemcitabine, palbociclib, afatinib, alectinib, axitinib, bortezomib, bosutinib, cabozantinib, carfilzomib, ceritinib, cobimetinib, crizotinib, dabrafenib, erlotinib, gefitinib, ibrutinib, idelalisib, imatinib, ixazomib, lapatinib, nilotinib, nintedanib, niraparib, osimertinib, pazopanib, pegaptanib, ponatinib, rucaparib, ruxolitinib, sonidegib, tofacitinib, trametinib, vandetanib, vemurafenib, vismodegibor, or a pharmaceutically acceptable salt thereof, as a combined preparation for simultaneous, separate, or sequential use in the treatment or prevention of non-small cell lung cancer, renal cell carcinoma, hepatocellular carcinoma, thyroid carcinoma, melanoma, multiple myeloma, mantle cell lymphoma, non-Hodgkin's lymphoma, colorectal cancer, acute lymphocytic leukemia, chronic lymphocytic leukemia, chronic myelogenous leukemia, skin cancer, ovarian cancer, gastrointestinal stromal tumors, breast cancer, prostate cancer, pancreatic cancer, or thymoma.

In one aspect, this application pertains to kit comprising:
(a) a pharmaceutical composition comprising milciclib, or a pharmaceutically acceptable salt thereof;
(b) a pharmaceutical composition comprising sorafenib, lenvatinib, regorafenib, sunitinib, nivolumab, gemcitabine, palbociclib, afatinib, alectinib, axitinib, bortezomib, bosutinib, cabozantinib, carfilzomib, ceritinib, cobimetinib, crizotinib, dabrafenib, erlotinib, gefitinib, ibrutinib, idelalisib, imatinib, ixazomib, lapatinib, nilotinib, nintedanib, niraparib, osimertinib, pazopanib, pegaptanib, ponatinib, rucaparib, ruxolitinib, sonidegib, tofacitinib, trametinib, vandetanib, vemurafenib, vismodegibor, or a pharmaceutically acceptable salt thereof; and
(c) instructions for the use thereof in the treatment and/or prevention of cancer.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 74A, 74B, and 74C are a series of graphs depicting relative expression of MKI67 (74A), c-Myc (74B) and Cdc6 (74C) in athymic mice with livers injected with MHCC97H cells following treatment with vehicle, sorafenib, milciclib, or milciclib+sorafenib.

DETAILED DESCRIPTION OF THE INVENTION

Figure 1:
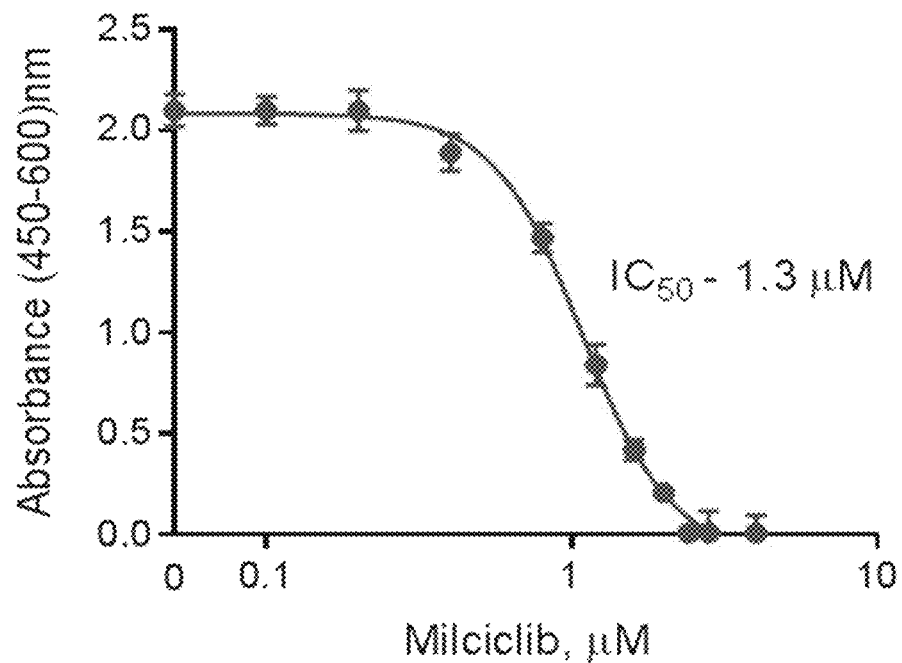
FIG. 1 is a graph showing the IC50 value of milciclib in MHCC97H cells.
Figure 2:
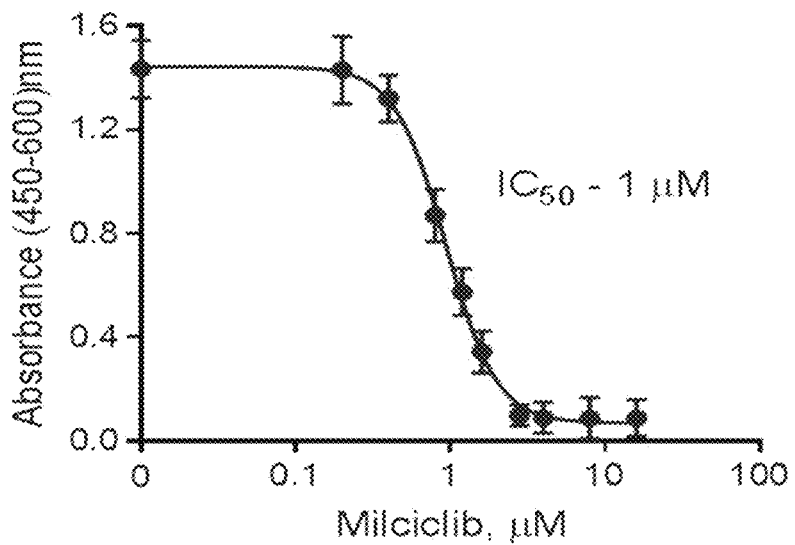
FIG. 2 is a graph showing the IC50 value of milciclib in MHCC97L cells.
Figure 3:
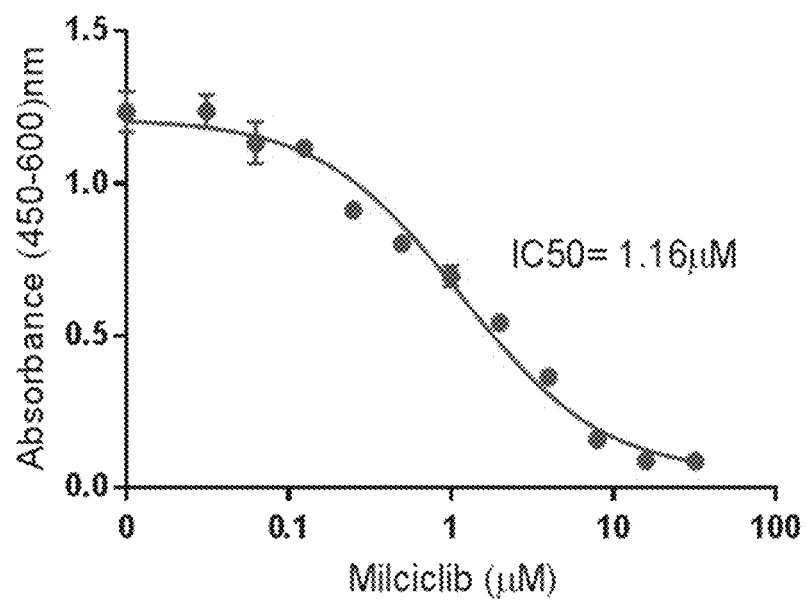
FIG. 3 is a graph showing the IC50 value of milciclib in HepG2.2.15 cells.

It must be noted that, as used in this specification and the appended claims, the singular forms "a," "an" and "the" include plural referents unless the context clearly dictates otherwise. Thus, for example, "a CDK inhibitor" refers not only to a single inhibitor but also to a combination of two or more different inhibitors, "a dosage form" refers to a combination of dosage forms as well as to a single dosage form, and the like.

Unless defined otherwise, all technical and scientific terms used herein have the meaning commonly understood by one of ordinary skill in the art to which the invention pertains. Specific terminology of particular importance to the description of the present invention is defined below.

As used herein, the term "patient" or "individual" or "subject" refers to any person or mammalian subject for whom or which therapy is desired, and generally refers to the recipient of the therapy to be practiced according to the invention.

As used herein, the term "CDK inhibitor" refers to a compound that inhibits the enzyme in humans referred to as cyclin-dependent kinase. Examples include, without limitation, milciclib, palbociclib, dinaciclib, P276-00, roniciclib, ribociclib, P1446A-05, AT7519M, SNS-032, SCH 727965, AG-024322, hygrolidin, fascaplysin, abemaciclib, arcyriaflavin A, CINK4, AM-5992, CDK4 Inhibitor (CAS #546102-60-7), CDK4 Inhibitor III (CAS #265312-55-8), Cdk4/6 Inhibitor IV (CAS #359886-84-3), MM-D37K, NSC 625987, ON-123300, or any pharmaceutically acceptable salt thereof. (See Law, M. E. et al. "Cyclin-Dependent Kinase Inhibitors as Anticancer Therapeutics" Mol. Pharmacol. 88:846-852 (2015), which is incorporated by reference herein in its entirety.). In one embodiment, the CDK inhibitor is milciclib.

As used here, the term "anticancer drug" or "anticancer agent" includes kinase inhibitor drugs which refers to any member of the group of anticancer drugs that specifically targets protein kinases that are altered in cancer cells and account for some of their abnormal growth. In one embodiment, the anticancer drug is selected from the group consisting of sorafenib, lenvatinib, regorafenib, sunitinib, palbociclib, afatinib, alectinib, axitinib, bortezomib, bosutinib, cabozantinib, carfilzomib, ceritinib, cobimetinib, crizotinib, dabrafenib, erlotinib, gefitinib, ibrutinib, idelalisib, imatinib, ixazomib, lapatinib, nilotinib, nintedanib, niraparib, osimertinib, pazopanib, pegaptanib, ponatinib, rucaparib, ruxolitinib, sonidegib, tofacitinib, trametinib, vandetanib, vemurafenib, vismodegibor, or any pharmaceutically acceptable salt thereof. In one embodiment, the anticancer drug is sorafenib. In one embodiment, the anticancer drug is lenvatinib. In one embodiment, the anticancer drug is regorafenib. In one embodiment, the anticancer drug is sunitinib. In one embodiment, the anticancer drug is palbociclib.

Other anticancer drugs, include, without limitation, an alkylating agent, an antibiotic, an anti-metabolite, a detoxifying agent, an interferon, a polyclonal or monoclonal antibody, an EGFR inhibitor, a HER2 inhibitor, a histone deacetylase inhibitor, a hormone; a mitotic inhibitor, an MTOR inhibitor, a multi-kinase inhibitor, a serine/threonine kinase inhibitor, a tyrosine kinase inhibitors, a VEGF/VEGFR inhibitor, a taxane or taxane derivative, an aromatase inhibitor, an anthracycline, a microtubule targeting drug, a topoisomerase poison drug, an inhibitor of a molecular target or enzyme (e.g., a kinase inhibitor), a cytidine analogue drug, or any chemotherapeutic, anti-neoplastic or anti-proliferative agent listed in www.cancer.org/docroot/cdg-cdg_0.asp. In one embodiment, the anticancer drug is nivolumab. In one embodiment, the anticancer drug is gemcitabine.

When referring to an active agent, applicant intends the term "active agent" to encompass not only the specified molecular entity but also its pharmaceutically acceptable, pharmacologically active analogs, including, but not limited to, salts, esters, amides, prodrugs, conjugates, active metabolites, crystalline forms (including polymorphs), enantiomers, and other such derivatives, analogs, and related compounds.

The terms "treating" and "treatment" include the following actions: (i) preventing a particular disease or disorder from occurring in a subject who may be predisposed to the disease or disorder but has not yet been diagnosed as having it; (ii) inhibiting the disease, i.e., arresting its development; or (iii) relieving the disease by reducing or eliminating symptoms and/or by causing regression of the disease.

The term "unit dosage forms" as used herein refers to physically discrete units suited as unitary dosages for the individuals to be treated. That is, the compositions are formulated into discrete dosage units each containing a predetermined, "unit dosage" quantity of an active agent calculated to produce the desired therapeutic effect in association with the required pharmaceutical carrier. The specifications of unit dosage forms of the invention are dependent on the unique characteristics of the active agent to be delivered. Dosages can further be determined by reference to the usual dose and manner of administration of the ingredients. It should be noted that, in some cases, two or more individual dosage units in combination provide a therapeutically effective amount of the active agent, e.g., two tablets or capsules taken together may provide a therapeutically effective dosage of milciclib, such that the unit dosage in each tablet or capsule is approximately 50% of the therapeutically effective amount.

By the terms "effective amount" and "therapeutically effective amount" of a compound is meant a nontoxic but sufficient amount of an active agent to provide the desired effect, i.e., treatment of cancer.

As used herein, a "subject in need thereof" is a subject having cancer, or a subject having an increased risk of developing cancer relative to the population at large.

The term "cancer" includes solid tumors, as well as, hematologic tumors and/or malignancies. A "cancer cell" or "cancerous cell" is a cell manifesting a cell proliferative disorder that is a cancer. Any reproducible means of measurement may be used to identify cancer cells. Cancer cells can be identified by histological typing or grading of a tissue sample (e.g., a biopsy sample). Cancer cells can be identified through the use of appropriate molecular markers.

Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, triple negative breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular carcinoma, hepatocellular (liver) cancer, Hodgkin lymphoma, hypopharyngeal cancer, intraocular melanoma, ocular cancer, islet cell tumors (endocrine pancreas), Kaposi's sarcoma, kidney cancer (renal cell carcinoma), renal cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, Ewing family of sarcoma tumors, Kaposi Sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, thyroid carcinoma, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

Methods of Treatment

The present application provides methods of treating cancer, comprising administering to a subject in need thereof a therapeutically effective amount of milciclib, or a pharmaceutically acceptable salt thereof, with one or more pharmaceutically acceptable carriers or excipients, in combination with a therapeutically effective amount of a second agent, i.e., an anticancer drug, with one or more pharmaceutically acceptable carriers or excipients, wherein the cancer is treated. In one embodiment, the anticancer drug is any compound disclosed herein other than milciclib.

The cancer can be a hematologic tumor or malignancy, or a solid tumor (or tumors), or a refractory solid tumor.

In one embodiment, the cancer is selected from the group consisting of non-small cell lung cancer, renal cell carcinoma, hepatocellular carcinoma, thyroid carcinoma, colorectal cancer, gastrointestinal stromal tumors, breast cancer (e.g., triple negative breast cancer), prostate cancer, pancreatic cancer, or thymoma (i.e., thymic carcinoma).

This method of treating cancer includes a reduction in tumor size. Alternatively, or in addition, the cancer is metastatic cancer and this method of treatment includes inhibition of metastatic cancer cell invasion.

The other anticancer drug or agent can be an alkylating agent; an antibiotic; an anti-metabolite; a detoxifying agent; an interferon; a polyclonal or monoclonal antibody; an EGFR inhibitor; a HER2 inhibitor; a histone deacetylase inhibitor; a hormone; a mitotic inhibitor; an MTOR inhibitor; a multi-kinase inhibitor; a serine/threonine kinase inhibitor; a tyrosine kinase inhibitors; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase inhibitor), a cytidine analogue drug or any chemotherapeutic, anti-neoplastic or anti-proliferative agent listed in www.cancer.org/docroot/cdg/cdg_0.asp.

In one embodiment, the other anticancer agent is an anti-metabolite or a nucleoside analog. Exemplary anti-metabolites or nucleoside analogs include, but are not limited to, fluorouracil (Adrucil); capecitabine (Xeloda); hydroxyurea (Hydrea); mercaptopurine (Purinethol); pemetrexed (Alimta); fludarabine (Fludara); nelarabine (Arranon); cladribine (Cladribine Novaplus); clofarabine (Clolar); cytarabine (Cytosar-U); decitabine (Dacogen); cytarabine liposomal (DepoCyt); hydroxyurea (Droxia); pralatrexate (Folotyn); floxuridine (FUDR); gemcitabine (Gemzar); cladribine (Leustatin); fludarabine (Oforta); methotrexate (MTX; Rheumatrex); methotrexate (Trexall); thioguanine (Tabloid); TS-1 or cytarabine (Tarabine PFS).

In one embodiment, the other anticancer drug or agent is selected from the group consisting of sorafenib, lenvatinib, regorafenib, sunitinib, nivolumab, gemcitabine, and palbociclib.

Milciclib or a pharmaceutically acceptable salt thereof, and/or the other anticancer drug, can be incorporated into pharmaceutical compositions suitable for administration. Such compositions typically comprise the compound (i.e. including the active compound), and a pharmaceutically acceptable excipient or carrier. As used herein, "pharmaceutically acceptable excipient" or "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field. Preferred examples of such carriers or diluents include, but are not limited to, water, saline, ringer's solutions, dextrose solution, and 5% human serum albumin.

Pharmaceutically acceptable carriers include solid carriers such as lactose, terra alba, sucrose, talc, gelatin, agar, pectin, acacia, magnesium stearate, stearic acid and the like. Exemplary liquid carriers include syrup, peanut oil, olive oil, water and the like. Similarly, the carrier or diluent may include time-delay material known in the art, such as glyceryl monostearate or glyceryl distearate, alone or with a wax, ethylcellulose, hydroxypropylmethylcellulose, methylmethacrylate or the like. Other fillers, excipients, flavorants, and other additives such as are known in the art may also be included in a pharmaceutical composition according to this application. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

In one aspect, milciclib, or a pharmaceutically acceptable salt thereof, and/or the other anticancer drug, is administered in a suitable dosage form prepared by combining a therapeutically effective amount (e.g., an efficacious level sufficient to achieve the desired therapeutic effect through inhibition of tumor growth, killing of tumor cells, etc.) of milciclib, or a pharmaceutically acceptable salt thereof (as an active ingredient) and/or the other anticancer drug or agent, with standard pharmaceutical carriers or diluents according to conventional procedures (i.e., by producing a pharmaceutical composition of the application). These procedures may involve mixing, granulating, and compressing or dissolving the ingredients as appropriate to attain the desired preparation.

As used herein, "treating" describes the management and care of a subject for the purpose of combating a disease, condition, or disorder and includes decreasing or alleviating the symptoms or complications, or eliminating the disease, condition or disorder.

As used herein, "preventing" describes stopping the onset of the symptoms or complications of the disease, condition or disorder.

In one aspect, treating cancer results in a reduction in size of a tumor. A reduction in size of a tumor may also be referred to as "tumor regression." Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. In a preferred aspect, size of a tumor may be measured as a diameter of the tumor.

In another aspect, treating cancer results in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

In another aspect, treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. In a preferred aspect, number of tumors may be measured by counting tumors visible to the naked eye or at a specified magnification. In a preferred aspect, the specified magnification is 2×, 3×, 4×, 5×, 10×, or 50×.

In another aspect, treating cancer results in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. In a preferred aspect, the number of metastatic lesions may be measured by counting metastatic lesions visible to the naked eye or at a specified magnification. In a preferred aspect, the specified magnification is 2×, 3×, 4×, 5×, 10×, or 50×.

In another aspect, treating cancer results in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. In a preferred aspect, an increase in average survival time of a population may be measured, for example, by calculating for a population the average length of survival following initiation of treatment with an active compound. In another preferred aspect, an increase in average survival time of a population may also be measured, for example, by calculating for a population the average length of survival following completion of a first round of treatment with an active compound.

In another aspect, treating cancer results in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. In a preferred aspect, an increase in average survival time of a population may be measured, for example, by calculating for a population the average length of survival following initiation of treatment with an active compound. In another preferred aspect, an increase in average survival time of a population may also be measured, for example, by calculating for a population the average length of survival following completion of a first round of treatment with an active compound.

In another aspect, treating cancer results in increase in average survival time of a population of treated subjects in comparison to a population receiving monotherapy with a drug that is not milciclib, or a pharmaceutically acceptable salt, prodrug, metabolite, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means.

In a preferred aspect, an increase in average survival time of a population may be measured, for example, by calculating for a population the average length of survival following initiation of treatment with an active compound. In another preferred aspect, an increase in average survival time of a population may also be measured, for example, by calculating for a population the average length of survival following completion of a first round of treatment with an active compound.

In another aspect, treating cancer results in a decrease in the mortality rate of a population of treated subjects in comparison to a population receiving carrier alone. In another aspect, treating cancer results in a decrease in the mortality rate of a population of treated subjects in comparison to an untreated population. In a further aspect, treating cancer results a decrease in the mortality rate of a population of treated subjects in comparison to a population receiving monotherapy with a drug that is not milciclib, or a pharmaceutically acceptable salt, prodrug, metabolite, analog or derivative thereof. Preferably, the mortality rate is decreased by more than 2%; more preferably, by more than 5%; more preferably, by more than 10%; and most preferably, by more than 25%. In a preferred aspect, a decrease in the mortality rate of a population of treated subjects may be measured by any reproducible means. In another preferred aspect, a decrease in the mortality rate of a population may be measured, for example, by calculating for a population the average number of disease-related deaths per unit time following initiation of treatment with an active compound. In another preferred aspect, a decrease in the mortality rate of a population may also be measured, for example, by calculating for a population the average number of disease-related deaths per unit time following completion of a first round of treatment with an active compound.

In another aspect, treating cancer results in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. In a preferred aspect, tumor growth rate is measured according to a change in tumor diameter per unit time.

In another aspect, treating cancer results in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. In a preferred aspect, tumor regrowth is measured, for example, by measuring an increase in the diameter of a tumor after a prior tumor shrinkage that followed treatment. In another preferred aspect, a decrease in tumor regrowth is indicated by failure of tumors to reoccur after treatment has stopped.

One skilled in the art may refer to general reference texts for detailed descriptions of known techniques discussed herein or equivalent techniques. These texts include Ausubel et al., Current Protocols in Molecular Biology, John Wiley and Sons, Inc. (2005); Sambrook et al., Molecular Cloning, A Laboratory Manual (3d ed.), Cold Spring Harbor Press, Cold Spring Harbor, N.Y. (2000); Coligan et al., Current Protocols in Immunology, John Wiley & Sons, N.Y.; Enna et al., Current Protocols in Pharmacology, John Wiley & Sons, N.Y.; Fingl et al., The Pharmacological Basis of Therapeutics (1975), Remington's Pharmaceutical Sciences, Mack Publishing Co., Easton, Pa., 18th edition (1990). These texts can, of course, also be referred to in making or using an aspect of the application.

The term "controlled release" or "controlled release form" refers to a drug-containing formulation or fraction thereof in which release of the drug is not immediate, i.e., with a "controlled release" formulation, administration does not result in immediate release of the drug into an absorption pool. The term is used interchangeably with "non-immediate release" as defined in Remington: The Science and Practice of Pharmacy, Nineteenth Ed. (Easton, Pa.: Mack Publishing Company, 1995). In general, the term "controlled release" as used herein includes sustained release and delayed release formulations.

The term "sustained release" (synonymous with "extended release") is used in its conventional sense to refer to a drug formulation that provides for gradual release of a drug over an extended period of time, and that preferably, although not necessarily, results in substantially constant blood levels of a drug over an extended time period. The term "delayed release" is also used in its conventional sense, to refer to a drug formulation which, following administration to a patient, provides a measurable time delay before drug is released from the formulation into the patient's body.

By "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration. "Pharmacologically active" (or simply "active") as in a "pharmacologically active" derivative or analog, refers to a derivative or analog having the same type of pharmacological activity as the parent compound and approximately equivalent in degree.

Administration of the active agents may be carried out using any appropriate mode of administration. Thus, administration can be, for example oral or parenteral, although oral administration is preferred.

Depending on the intended mode of administration, the pharmaceutical formulation may be a solid, semi-solid or liquid, such as, for example, a tablet, a capsule, a caplet, a liquid, a suspension, an emulsion, a suppository, granules, pellets, beads, a powder, or the like, preferably in unit dosage form suitable for single administration of a precise dosage. Suitable pharmaceutical formulations and dosage forms may be prepared using conventional methods known to those in the field of pharmaceutical formulation and described in the pertinent texts and literature, e.g., in Remington: The Science and Practice of Pharmacy (Easton, Pa.: Mack Publishing Co., 1995). Oral administration and therefore oral dosage forms are generally preferred, and include tablets, capsules, caplets, solutions, suspensions and syrups, and may also comprise a plurality of granules, beads, powders, or pellets that may or may not be encapsulated. Preferred oral dosage forms are capsules and tablets.

As noted above, it is especially advantageous to formulate compositions of the invention in unit dosage form for ease of administration and uniformity of dosage. The term "unit dosage forms" as used herein refers to physically discrete units suited as unitary dosages for the individuals to be treated. That is, the compositions are formulated into discrete dosage units each containing a predetermined, "unit dosage" quantity of an active agent calculated to produce the desired therapeutic effect in association with the required pharmaceutical carrier. The specifications of unit dosage forms of the invention are dependent on the unique characteristics of the active agent to be delivered. Dosages can further be determined by reference to the usual dose and manner of administration of the ingredients. It should be noted that, in some cases, two or more individual dosage units in combination provide a therapeutically effective amount of the active agent, e.g., two tablets or capsules taken together may provide a therapeutically effective dosage of each active agent, such that the unit dosage in each tablet or capsule is approximately 50% of the therapeutically effective amount.

Tablets may be manufactured using standard tablet processing procedures and equipment. Direct compression and granulation techniques are preferred. In addition to the active agent, tablets will generally contain inactive, pharmaceutically acceptable carrier materials such as binders, lubricants, disintegrants, fillers, stabilizers, surfactants, coloring agents, and the like.

Capsules are also preferred oral dosage forms, in which case the active agent-containing composition may be encapsulated in the form of a liquid or solid (the latter including particulates such as granules, beads, powders or pellets). Suitable capsules may be either hard or soft, and are generally made of gelatin, starch, or a cellulosic material, with gelatin capsules preferred. Two-piece hard gelatin capsules are preferably sealed, such as with gelatin bands or the like. See, for example, Remington: The Science and Practice of Pharmacy, cited earlier herein, which describes materials and methods for preparing encapsulated pharmaceuticals.

Generally, as will be appreciated by those of ordinary skill in the art, sustained release dosage forms are formulated by dispersing the active agents within a matrix of a gradually hydrolyzable material such as a hydrophilic polymer, or by coating a solid, drug-containing dosage form with such a material. Hydrophilic polymers useful for providing a sustained release coating or matrix include, by way of example: cellulosic polymers such as hydroxypropyl cellulose, hydroxyethyl cellulose, hydroxypropyl methyl cellulose, methyl cellulose, ethyl cellulose, cellulose acetate, and carboxymethylcellulose sodium; acrylic acid polymers and copolymers, preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate; and vinyl polymers and copolymers such as polyvinyl pyrrolidone, polyvinyl acetate, and ethylene-vinyl acetate copolymer.

Sustained release dosage forms herein may be composed of the acrylate and methacrylate copolymers available under the tradename "Eudragit" from Rohm Pharma (Germany). The Eudragit series E, L, S, RL, RS, and NE copolymers are available as solubilized in organic solvent, in an aqueous dispersion, or as a dry powder. Preferred acrylate polymers are copolymers of methacrylic acid and methyl methacrylate, such as the Eudragit L and Eudragit S series polymers. In one embodiment, any of the pharmaceutical formulations may be formulated for sustained release, i.e., in a sustained release dosage form.

Preparations according to this invention for parenteral administration include sterile aqueous and non-aqueous solutions, suspensions, and emulsions. Injectable aqueous solutions contain the active agent in water-soluble form. Examples of non-aqueous solvents or vehicles include fatty oils, such as olive oil and corn oil, synthetic fatty acid esters, such as ethyl oleate or triglycerides, low molecular weight alcohols such as propylene glycol, synthetic hydrophilic polymers such as polyethylene glycol, liposomes, and the like. Parenteral formulations may also contain adjuvants such as solubilizers, preservatives, wetting agents, emulsifiers, dispersants, and stabilizers, and aqueous suspensions may contain substances that increase the viscosity of the suspension, such as sodium carboxymethyl cellulose, sorbitol, and dextran. Injectable formulations are rendered sterile by incorporation of a sterilizing agent, filtration through a bacteria-retaining filter, irradiation, or heat. They can also be manufactured using a sterile injectable medium. The active agent may also be in dried, e.g., lyophilized, form that may be rehydrated with a suitable vehicle immediately prior to administration via injection.

Each of the active agents may in addition be administered through the skin using conventional transdermal drug delivery systems, wherein the active agent or agents are contained within a laminated structure that serves as a drug delivery device to be affixed to the skin. In such a structure, the drug composition is contained in a layer, or "reservoir," underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during drug delivery. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. Transdermal drug delivery systems may in addition contain a skin permeation enhancer.

In addition to the formulations described previously, the active agents may be formulated in a depot preparation for controlled release of the active agents, preferably sustained release over an extended time period. These sustained release dosage forms are generally administered by implantation (e.g., subcutaneously or intramuscularly or by intramuscular injection).

A "daily dose" of a particular material refers the amount of the material administered in a day. A daily dose can be administered as a single dose or as multiple doses. When a daily dose is administered as multiple doses, the daily dose is the sum of the amount of material administered in all of the multiple doses that are administered over the course of one day. For example, a daily dose of 12 mg can be administered in a single 12 mg dose once per day, in 6 mg doses administered twice per day, in 4 mg doses administered three times per day, in 2 mg doses administered six times per day, etc. The multiple doses can be the same or different doses of the material, unless otherwise specified. When a daily dose is administered as multiple doses, the multiple doses can be administered by the same or different route of administration, unless otherwise specified. Thus, a daily dose of 12 mg can include, for example, a 10 mg intramuscular dose and a 2 mg oral dose administered over the course of one day.

Administration of one compound "with" a second compound, as used herein, includes but is not limited to cases where the two compounds are administered simultaneously or substantially simultaneously. For example, administration of a first compound with a second compound can include administering the first compound in the morning and administering the second compound in the evening, as well as administering the first and second compounds in the same dosage form or in two different dosage forms that at the same or nearly the same time.

In combining the active agents disclosed herein, i.e., milciclib with another anticancer drug or agent disclosed herein, milciclib will generally reduce the quantity of the second drug or agent needed to achieve a therapeutic effect when administered as a monotherapy, and, conversely, the other anticancer drug or agent will generally reduce the quantity of milciclib required.

As the method of the application involves combination therapy, the active agents may be administered separately, at the same or at different times of day, or they be administered in a single pharmaceutical formulation.

In some embodiments, "temporal proximity" means that administration of the other anticancer drug occurs within a time period before or after the administration of the CDK inhibitor (e.g., milciclib), such that the therapeutic effect of the other kinase inhibitor drug overlaps with the therapeutic effect of the CDK inhibitor (e.g., milciclib). In some embodiments, the therapeutic effect of the other kinase inhibitor drug completely overlaps with the therapeutic effect of the CDK inhibitor (e.g., milciclib). In some embodiments, "temporal proximity" means that administration of the other kinase inhibitor drug occurs within a time period before or after the administration of the CDK inhibitor (e.g., milciclib), such that there is a synergistic effect between the other kinase inhibitor drug and the CDK inhibitor.

"Temporal proximity" may vary according to various factors, including but not limited to, the age, gender, weight, genetic background, medical condition, disease history, and treatment history of the subject to which the therapeutic agents are to be administered; the disease or condition to be treated or ameliorated; the therapeutic outcome to be achieved; the dosage, dosing frequency, and dosing duration of the therapeutic agents; the pharmacokinetics and pharmacodynamics of the therapeutic agents; and the route(s) through which the therapeutic agents are administered. In some embodiments, "temporal proximity" means within 15 minutes, within 30 minutes, within an hour, within two hours, within four hours, within six hours, within eight hours, within 12 hours, within 18 hours, within 24 hours, within 36 hours, within 2 days, within 3 days, within 4 days, within 5 days, within 6 days, within a week, within 2 weeks, within 3 weeks, within 4 weeks, with 6 weeks, or within 8 weeks. In some embodiments, multiple administration of one therapeutic agent can occur in temporal proximity to a single administration of another therapeutic agent. In some embodiments, temporal proximity may change during a treatment cycle or within a dosing regimen.

SUMMARY OF DATA/EXAMPLES

IC50 values by cell proliferation assay were determined for MHCC97H and MHCC97L (highly metastatic hepatocellular carcinoma cell line, derived from humans) and HepG2.2.15 cells (derived from the human hepatoblastoma cell line HepG2). The cells were treated with milciclib, sorafenib, regorafenib, sunitinib, and lenvatinib, individually or in combination. Each inhibitor exhibited a dose dependent decrease in cell proliferation with comparable half maximal inhibitory concentration (IC50) across the three cell lines: (FIGS. 1 and 4—MHCC97H cells; FIGS. 2 and 10-14—MHCC97L cells; and FIGS. 3 and 20-24, HepG2.2.15 cells.)

A synergistic effect on inhibition of cell proliferation was observed upon treating MHCC97H, MHCC97L, and HepG2.2.15 cells with increasing concentration of TKIs (tyrosine kinase inhibitors) in the presence of fixed concentration corresponding to milciclib $IC_{50}$ value. In all cases, the $IC_{50}$ value of each TKI was reduced by ~50% (MHCC97H: FIGS. 5-9; MHCC97L: FIGS. 15-19; HepG2.2.15: FIGS. 25-28).

Figure 29A:
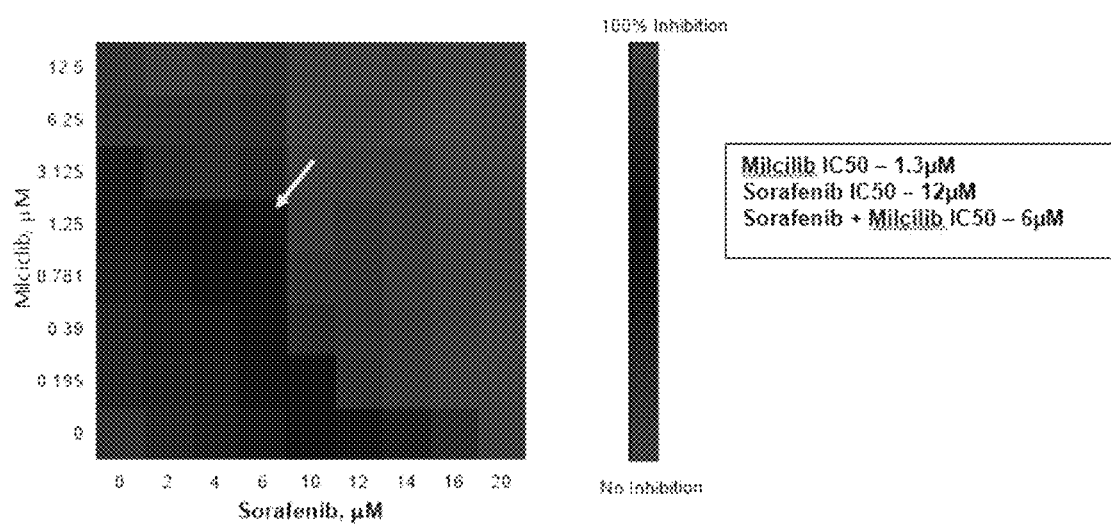
FIG. 29A is a heat map depicting synergism between milciclib and sorafenib in MHCC97H cells. Milciclib concentration is varied on the y-axis and sorafenib concentration is depicted along the x-axis. Red depicts 100% inhibition while green depicts 0% inhibition.
Figure 29B:
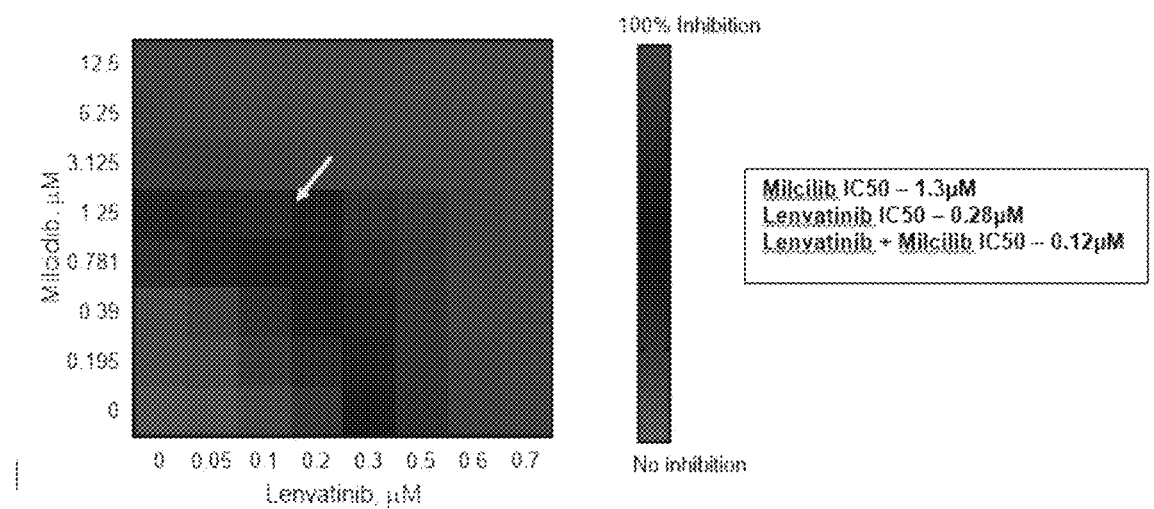
FIG. 29B is a heat map depicting synergism between milciclib and lenvatinib in MHCC97H cells. Milciclib concentration is varied on the y-axis and lenvatinib concentration is depicted along the x-axis. Red depicts 100% inhibition while green depicts 0% inhibition.
Figure 29C:
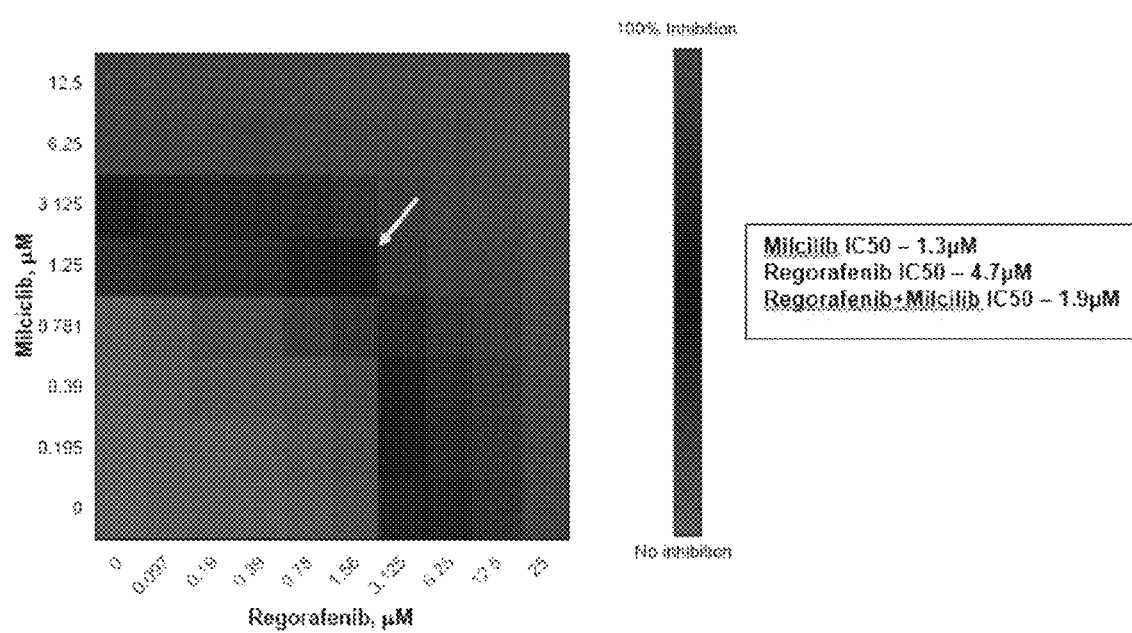
FIG. 29C is a heat map depicting synergism between milciclib and regorafenib in MHCC97H cells. Milciclib concentration is varied on the y-axis and regorafenib concentration is depicted along the x-axis. Red depicts 100% inhibition while green depicts 0% inhibition.

Increasing concentration of inhibitors with a fixed concentration of milciclib was tested on MHCC97L and MHCC97H cells to determine the synergistic effect on inhibition of cell proliferation. For sorafenib, the individual $IC_{50}$ was 12 µM but with the combination with milciclib the $IC_{50}$ was 6.7 µM in MHCC97H (FIG. 29A). For lenvatinib, the individual $IC_{50}$ was 0.28 µM but with the combination with milciclib the $IC_{50}$ was 0.12 µM in MHCC97H (FIG. 29B). For regorafenib, the individual $IC_{50}$ was 4.7 µM but with the combination with milciclib the $IC_{50}$ was 1.9 µM in MHCC97H (FIG. 29C).

Figure 30:
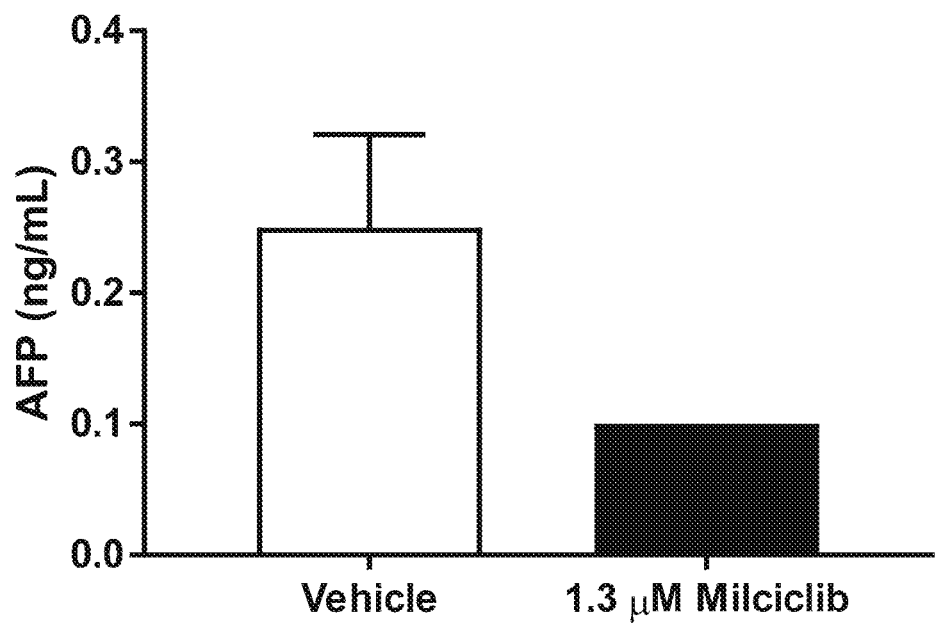
FIG. 30 is a graph showing changes in expression of alphafetoprotein (AFP) in MHCC97H cells treated with vehicle of milciclib.
Figure 31:
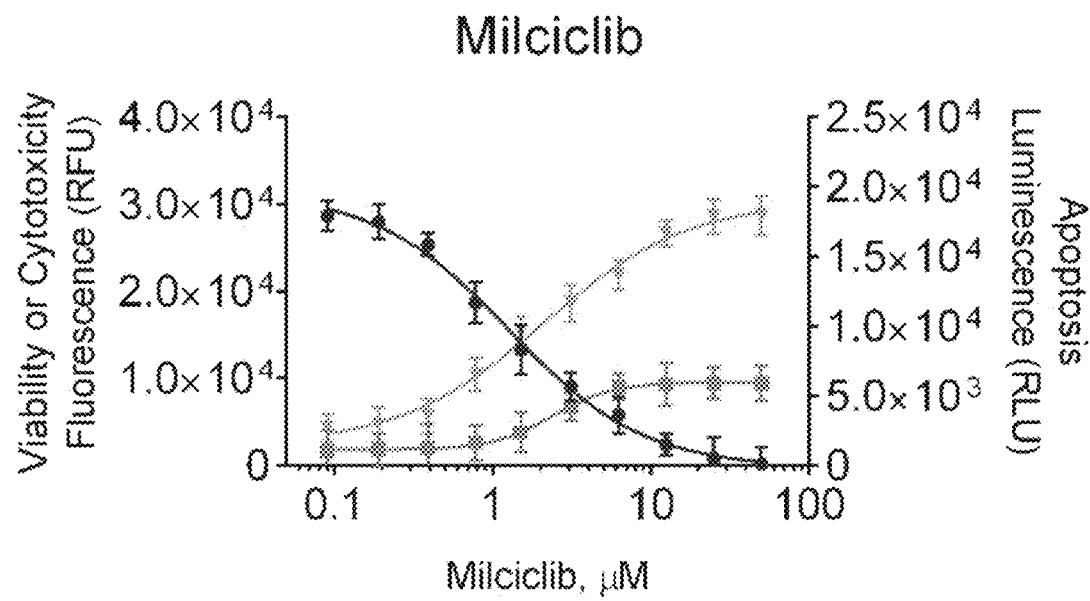
FIG. 31 is a series of graphs from the data collected in the Promega Triplex Assay of milciclib in MHCC97H cells.
Figure 32:
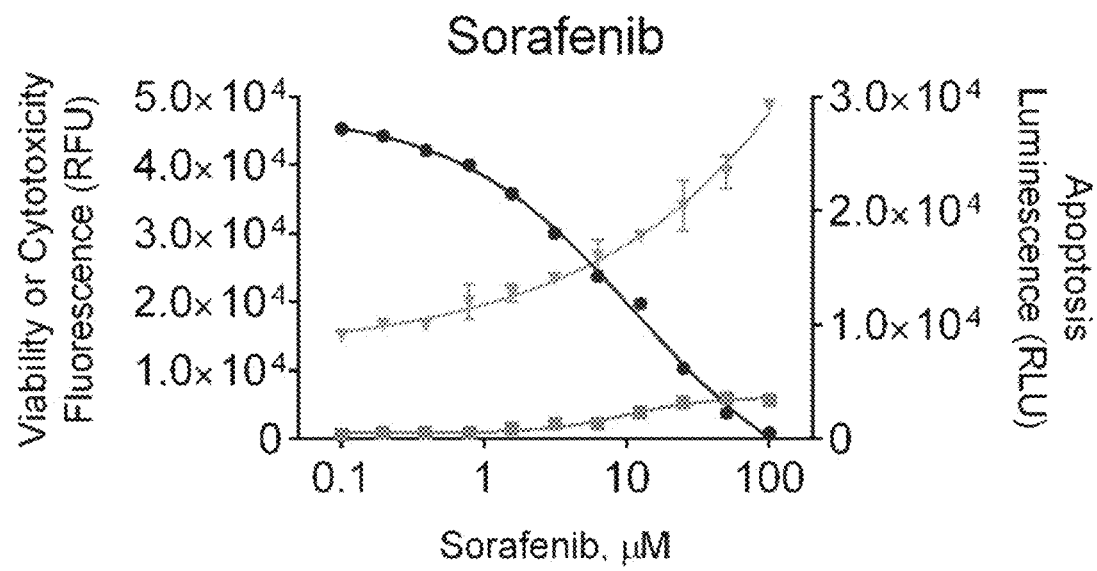
FIG. 32 is a series of graphs from the data collected in the Promega Triplex Assay of sorafenib in MHCC97H cells.
Figure 33:
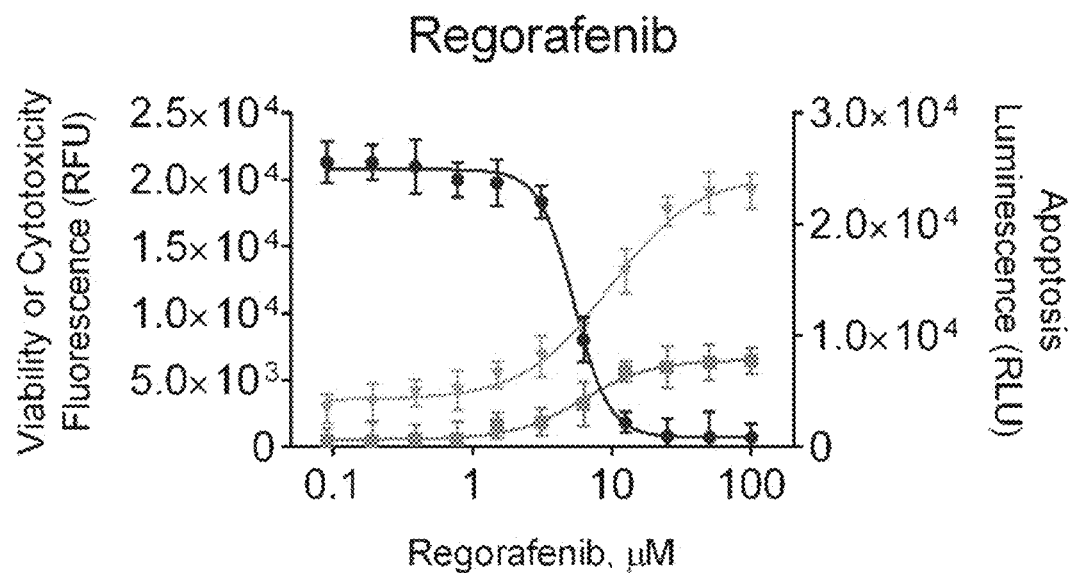
FIG. 33 is a series of graphs from the data collected in the Promega Triplex Assay of regorafenib in MHCC97H cells.
Figure 34:
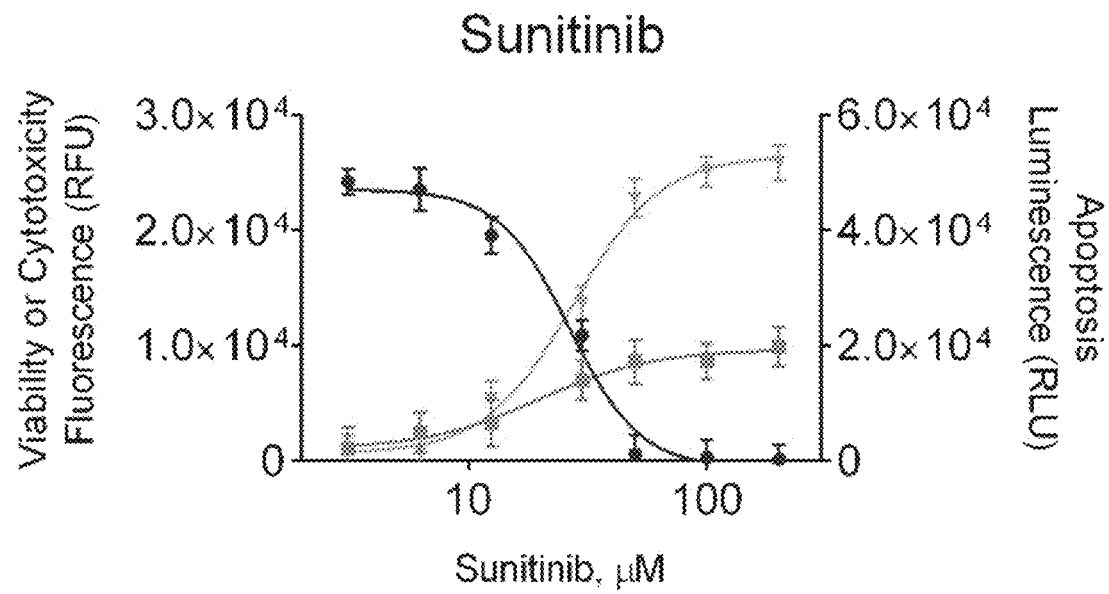
FIG. 34 is a series of graphs from the data collected in the Promega Triplex Assay of sunitinib in MHCC97H cells.
Figure 35:
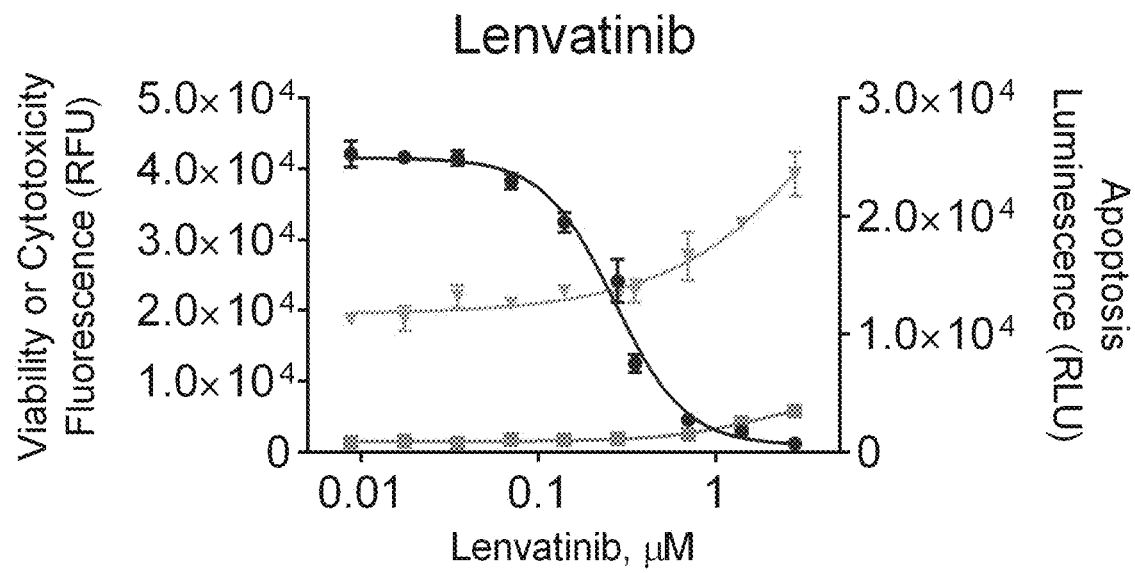
FIG. 35 is a series of graphs from the data collected in the Promega Triplex Assay of lenvatinib in MHCC97H cells.
Figure 36:
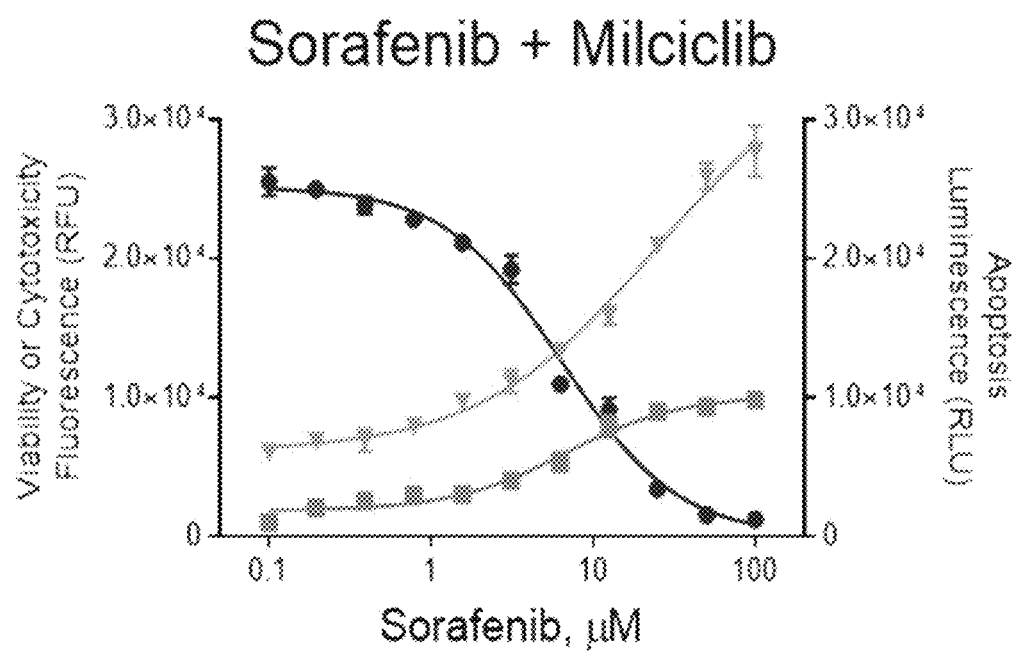
FIG. 36 is a series of graphs from the data collected in the Promega Triplex Assay of the combination of milciclib and sorafenib in MHCC97H cells.
Figure 37:
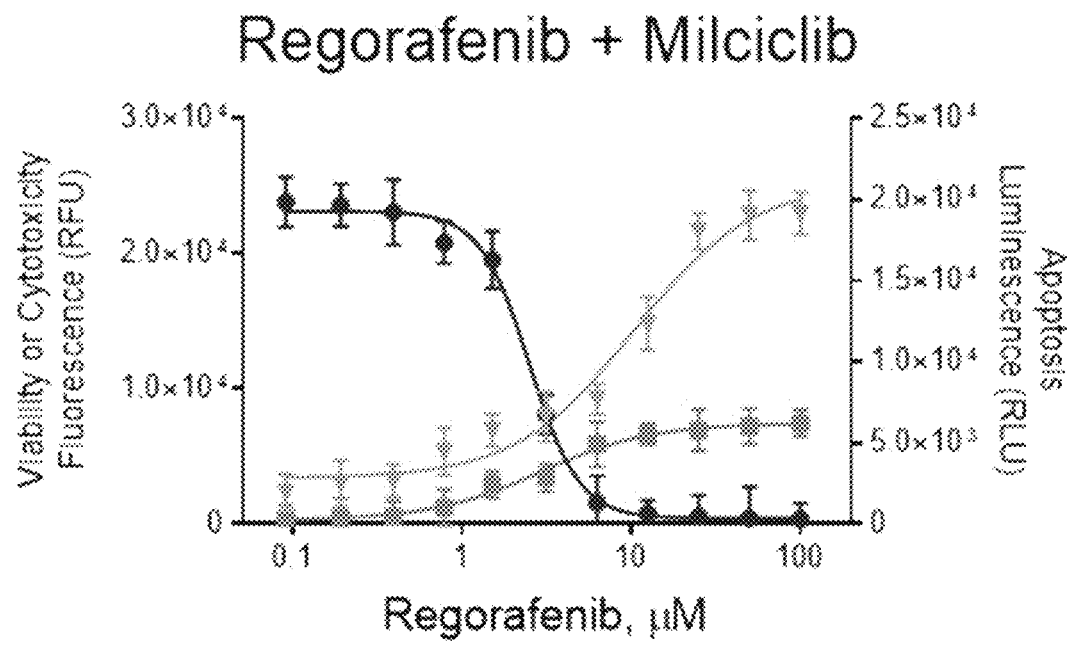
FIG. 37 is a series of graphs from the data collected in the Promega Triplex Assay of the combination of milciclib and regorafenib in MHCC97H cells.
Figure 38:
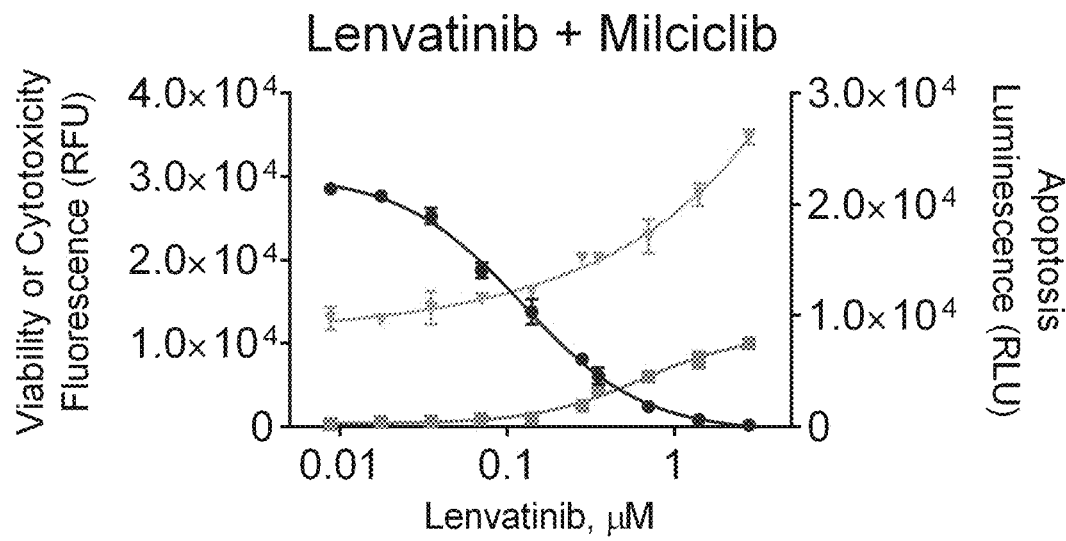
FIG. 38 is a series of graphs from the data collected in the Promega Triplex Assay of the combination of milciclib and lenvatinib in MHCC97H cells.
Figure 39:
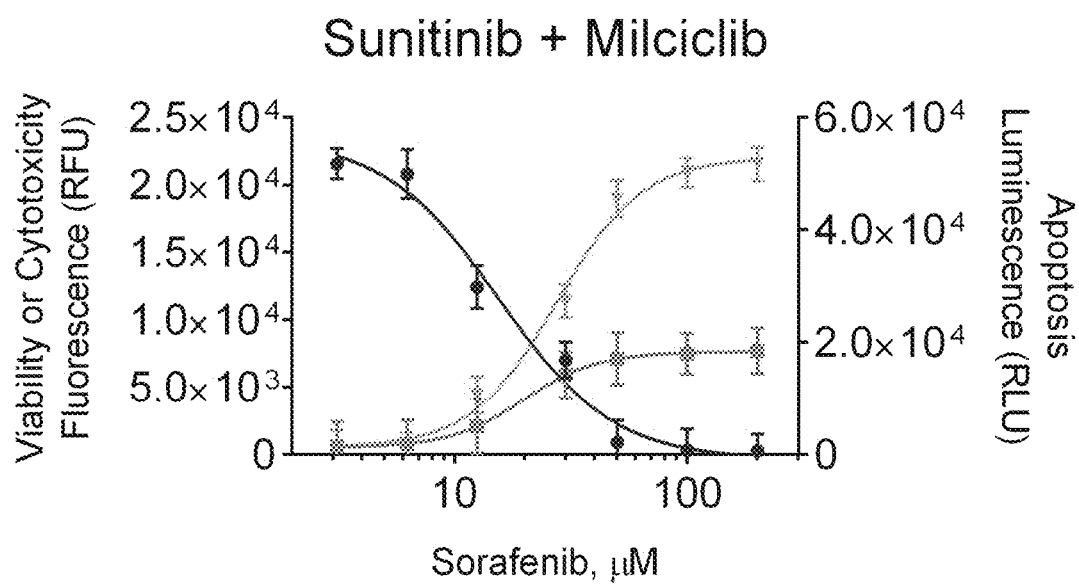
FIG. 39 is a series of graphs from the data collected in the Promega Triplex Assay of the combination of milciclib and sunitinib in MHCC97H cells.
Figure 40:
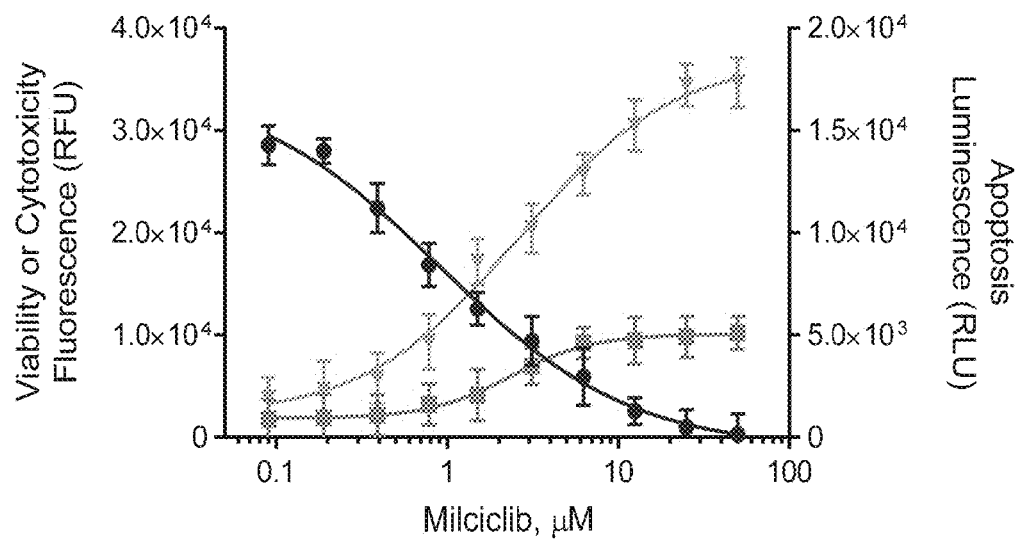
FIG. 40 is a series of graphs from the data collected in the Promega Triplex Assay of milciclib in MHCC97L cells.
Figure 41:
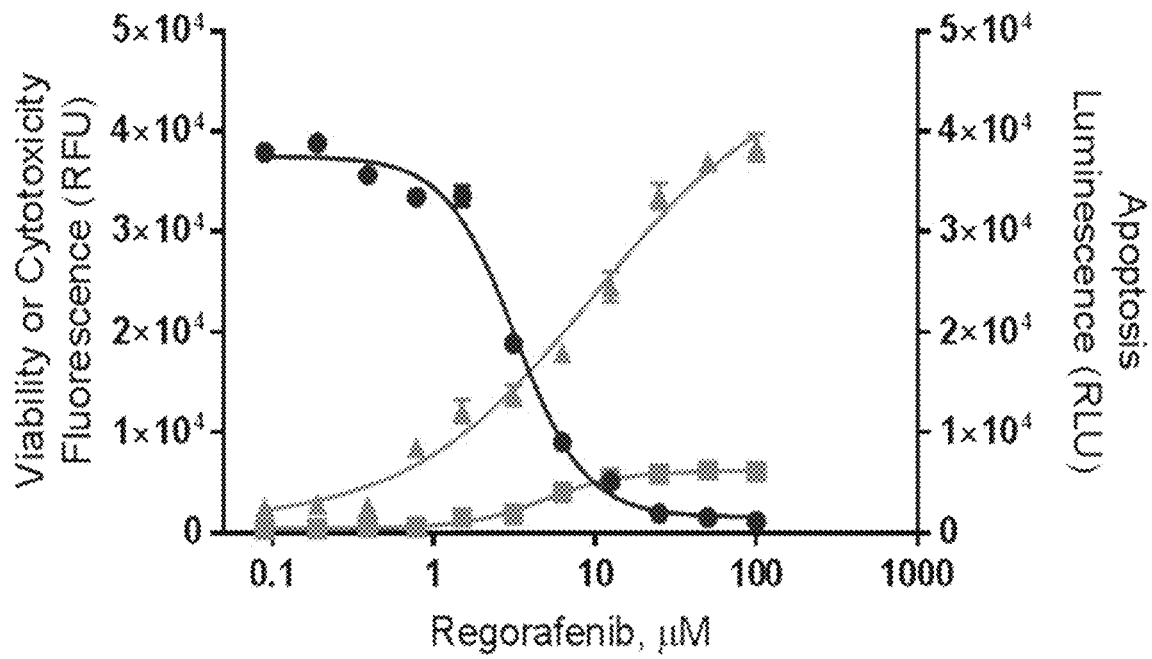
FIG. 41 is a series of graphs from the data collected in the Promega Triplex Assay of regorafenib in MHCC97L cells.
Figure 42:
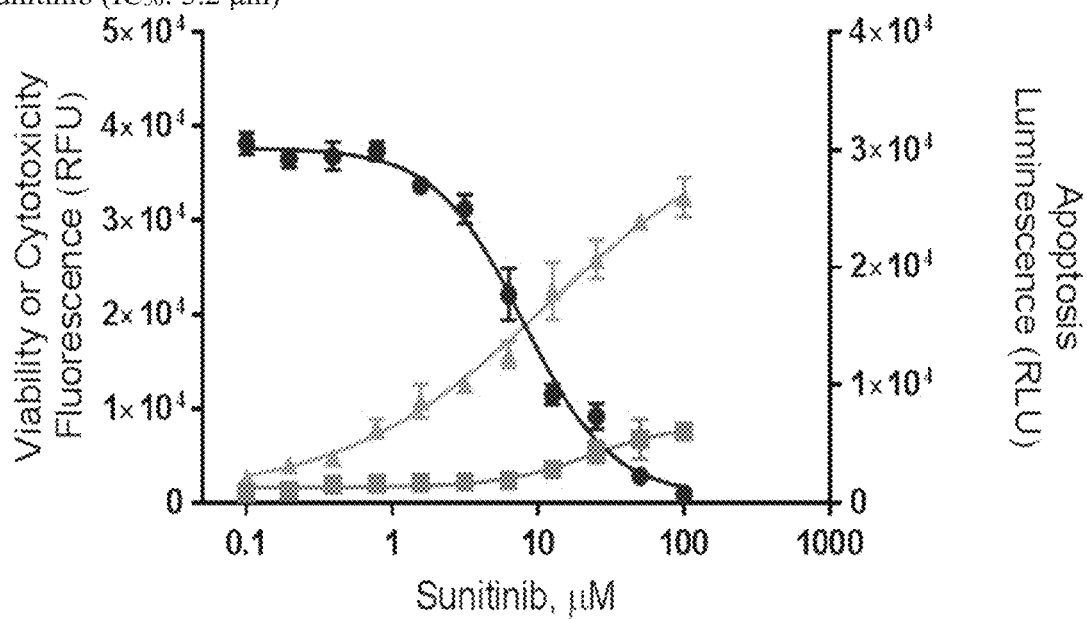
FIG. 42 is a series of graphs from the data collected in the Promega Triplex Assay of sunitinib in MHCC97L cells.
Figure 43:
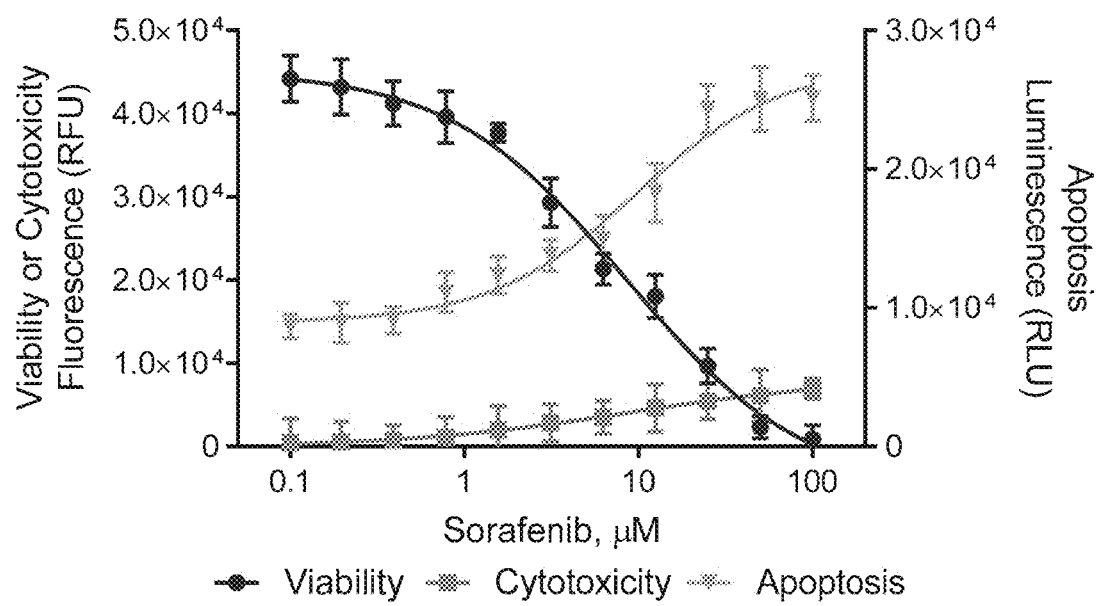
FIG. 43 is a series of graphs from the data collected in the Promega Triplex Assay of sorafenib in MHCC97L cells.
Figure 44:
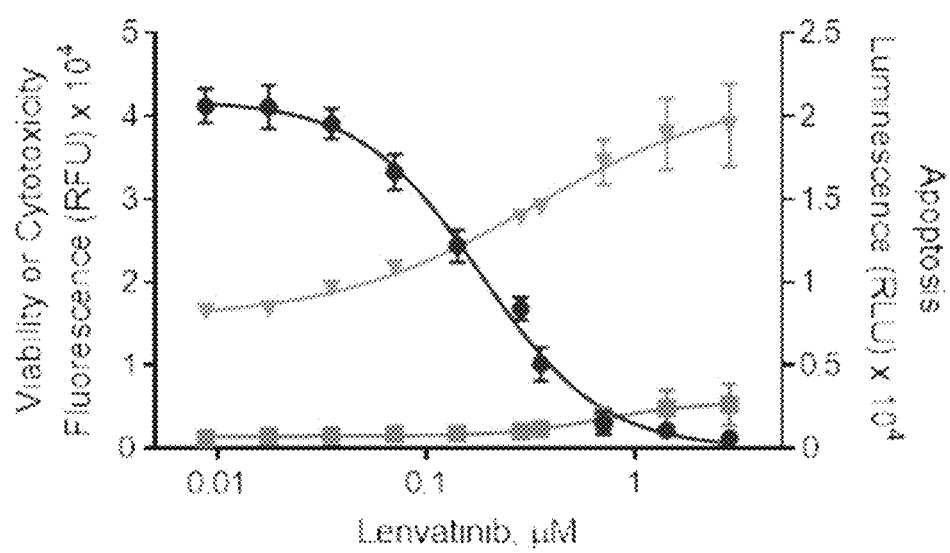
FIG. 44 is a series of graphs from the data collected in the Promega Triplex Assay of lenvatinib in MHCC97L cells.
Figure 45:
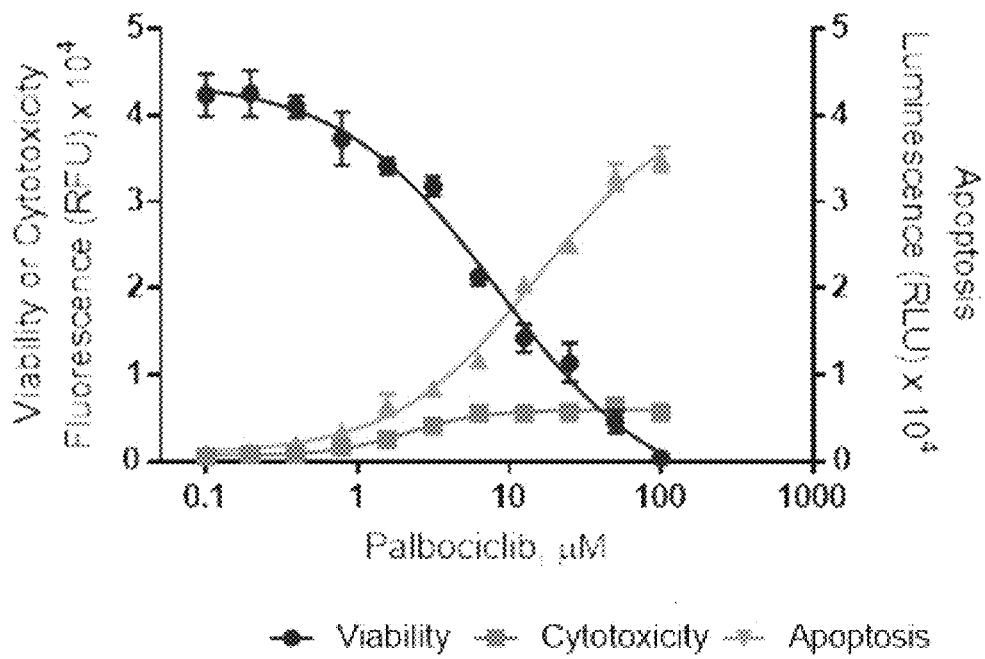
FIG. 45 is a series of graphs from the data collected in the Promega Triplex Assay of palbociclib in MHCC97L cells.
Figure 46:
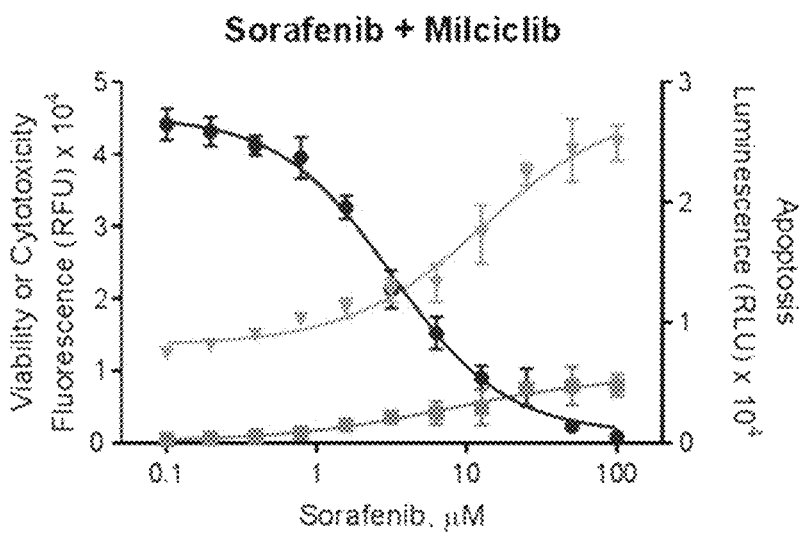
FIG. 46 is a series of graphs from the data collected in the Promega Triplex Assay of the combination of milciclib and sorafenib in MHCC97L cells.
Figure 47:
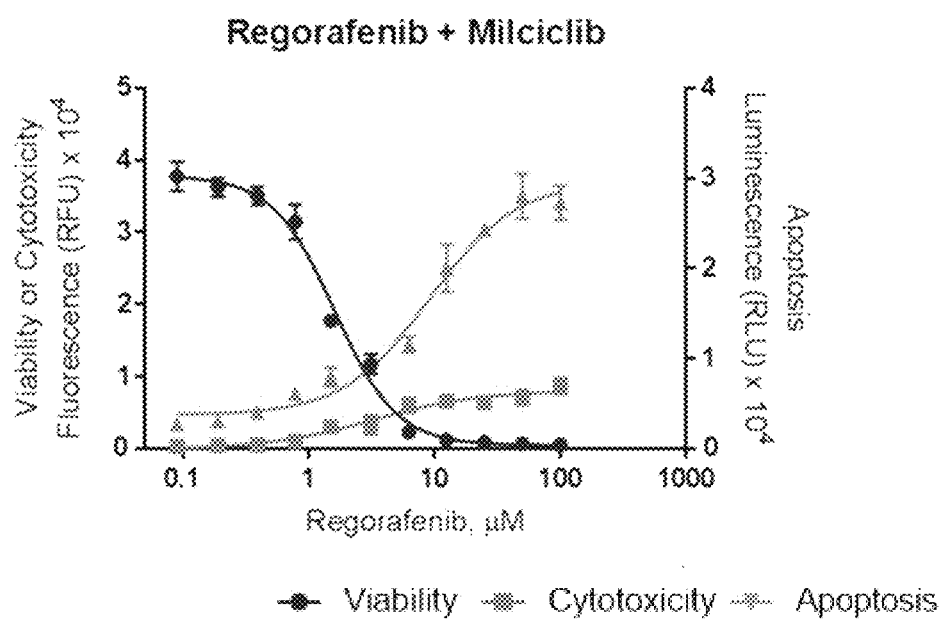
FIG. 47 is a series of graphs from the data collected in the Promega Triplex Assay of the combination of milciclib and regorafenib in MHCC97L cells.
Figure 48:
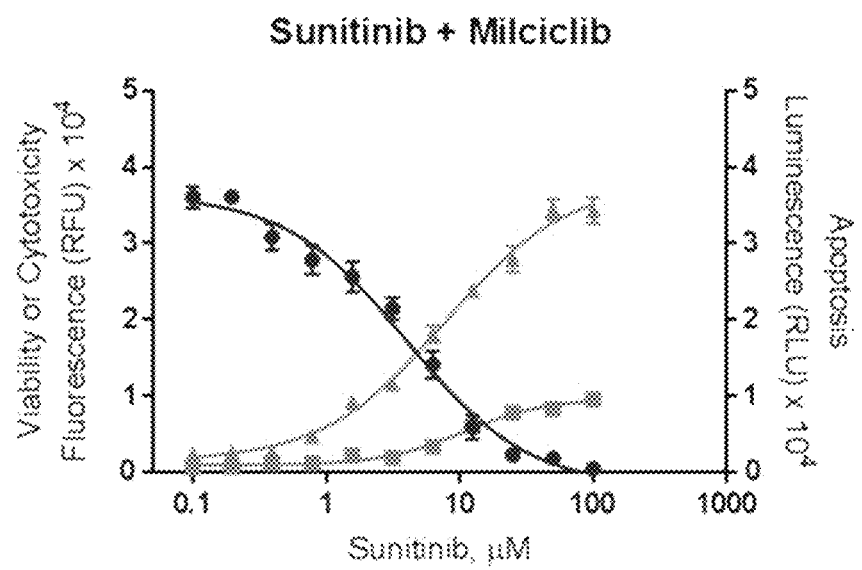
FIG. 48 is a series of graphs from the data collected in the Promega Triplex Assay of the combination of milciclib and sunitinib in MHCC97L cells.
Figure 49:
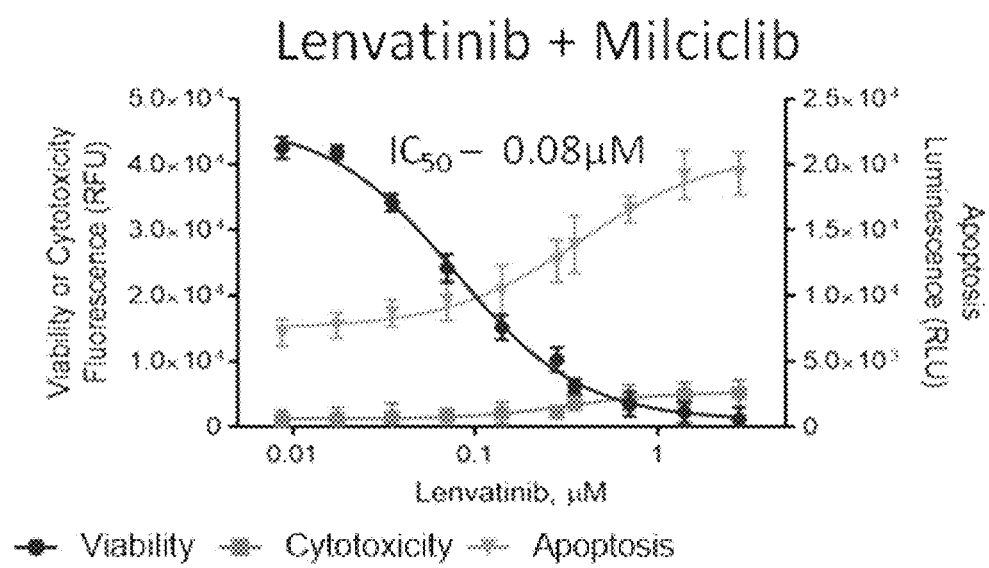
FIG. 49 is a series of graphs from the data collected in the Promega Triplex Assay of the combination of milciclib and lenvatinib in MHCC97L cells.
Figure 50:
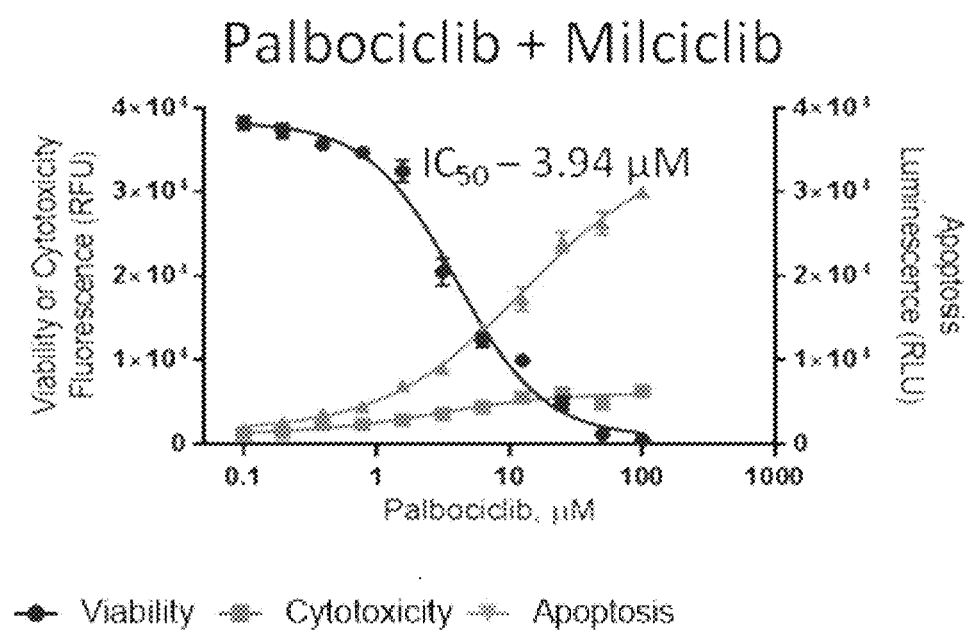
FIG. 50 is a series of graphs from the data collected in the Promega Triplex Assay of the combination of milciclib and palbociclib in MHCC97L cells.
Figure 51:
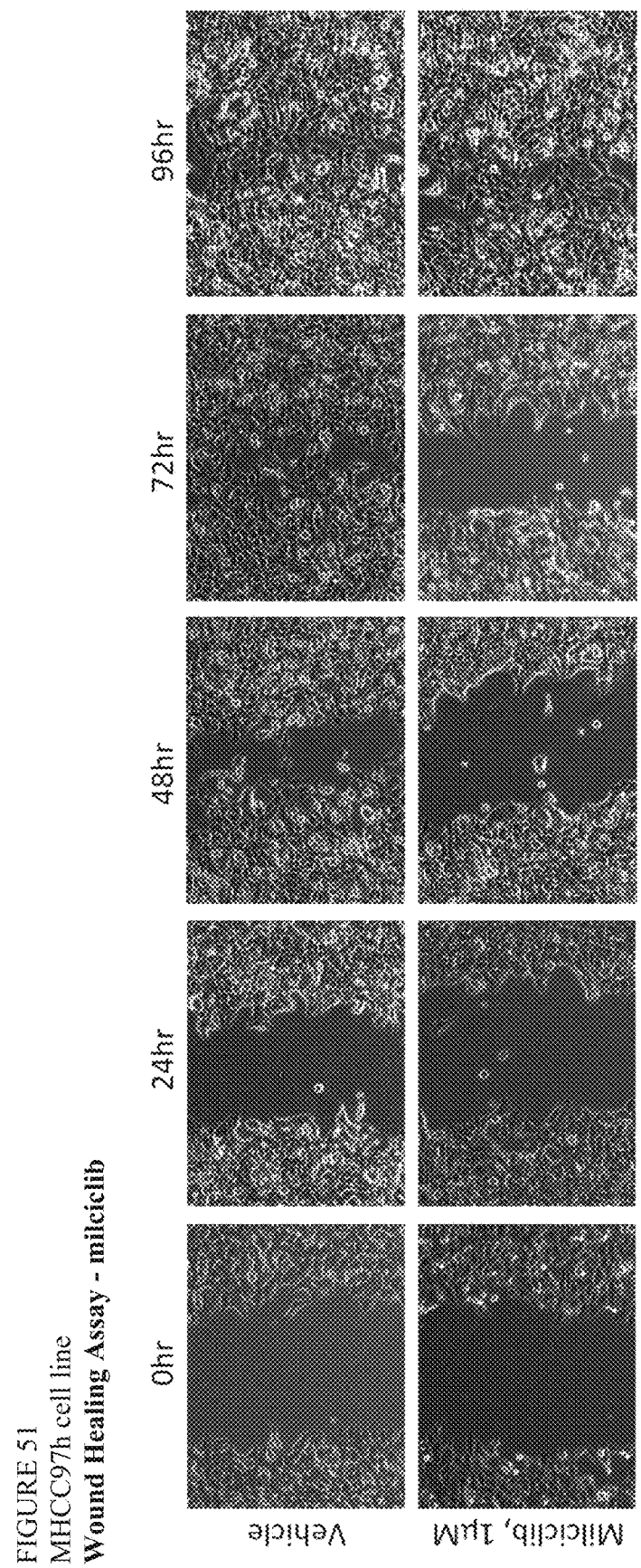
FIG. 51 is a series of photographs depicting the results of a wound-healing assay with milciclib in MHCC97H cells.
Figure 52:
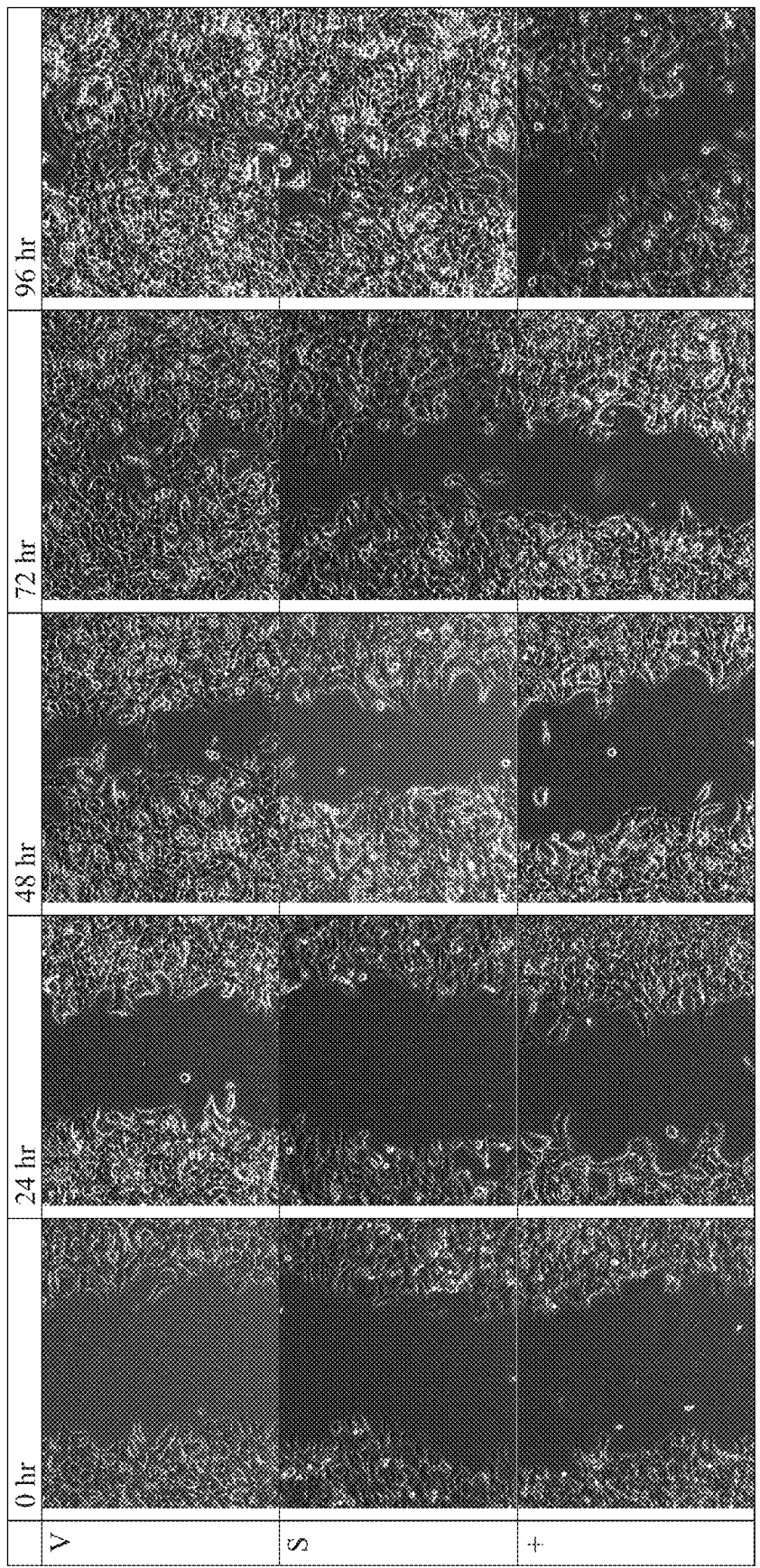
FIG. 52 is a series of photographs depicting the results of a wound-healing assay with sorafenib and the combination of sorafenib and milciclib in MHCC97H cells.
Figure 53:
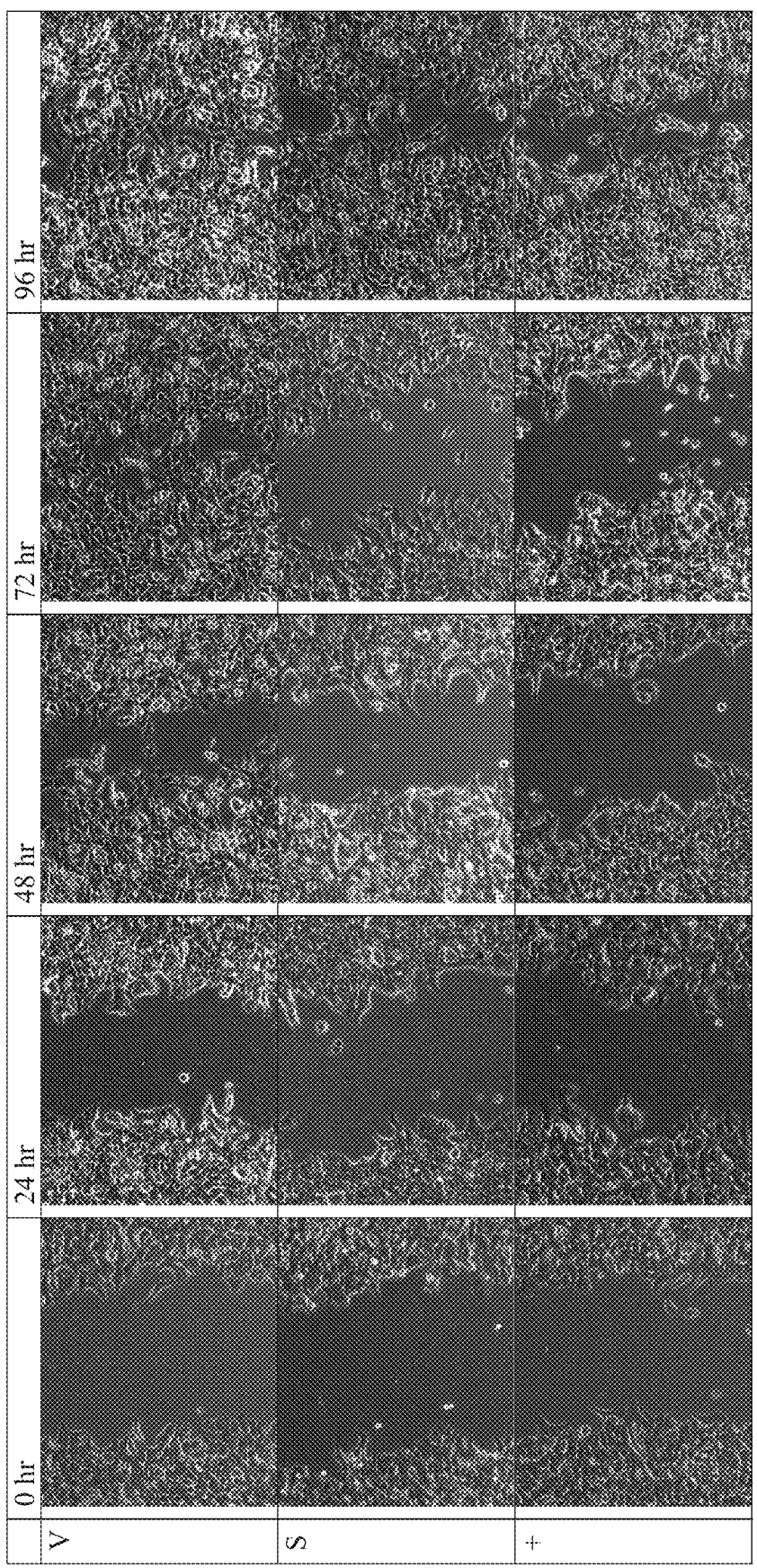
FIG. 53 is a series of photographs depicting the results of a wound-healing assay with sunitinib and the combination of sunitinib and milciclib in MHCC97H cells.
Figure 54:
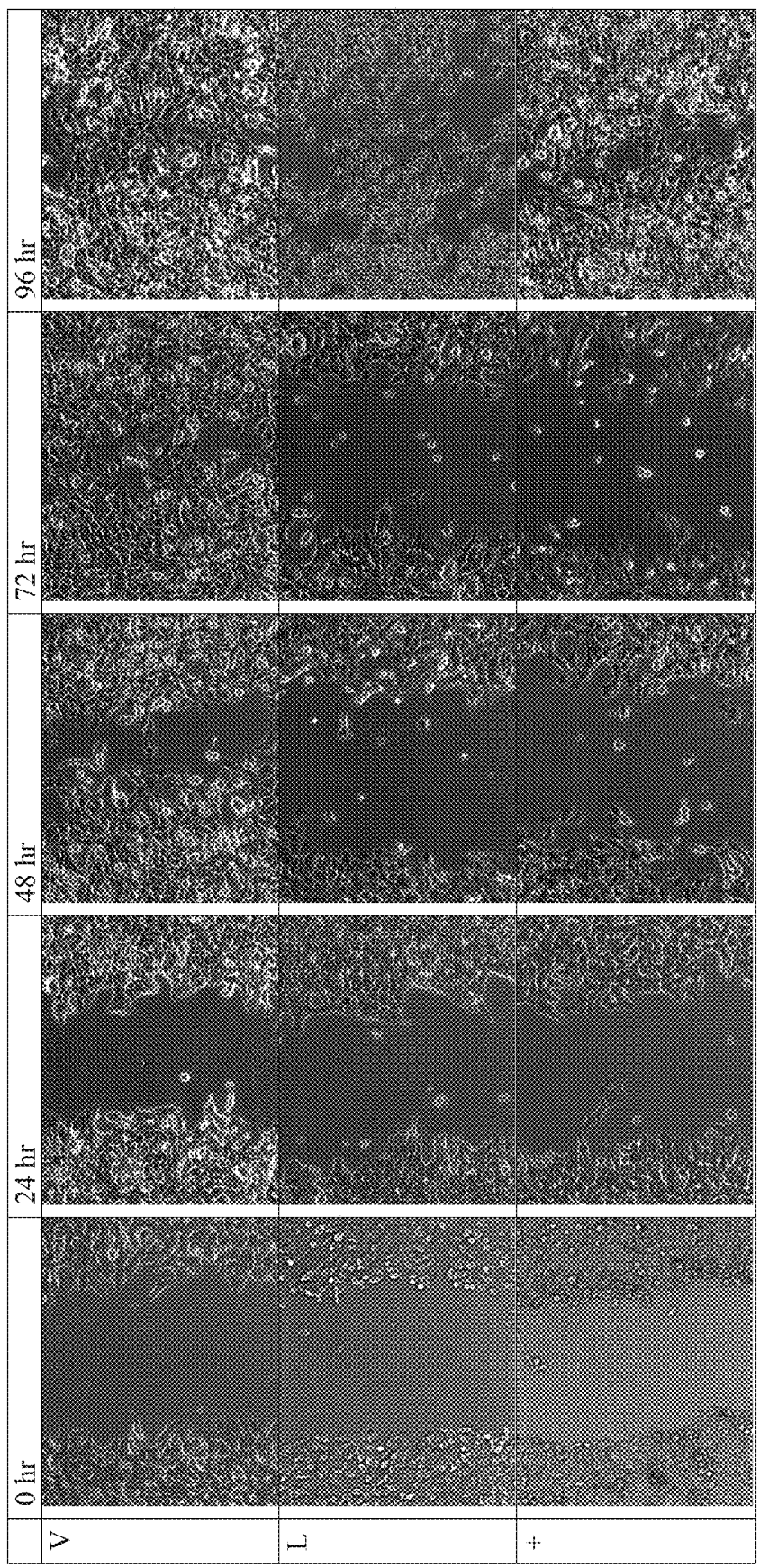
FIG. 54 is a series of photographs depicting the results of a wound-healing assay with lenvatinib and the combination of lenvatinib and milciclib in MHCC97H cells.
Figure 55:
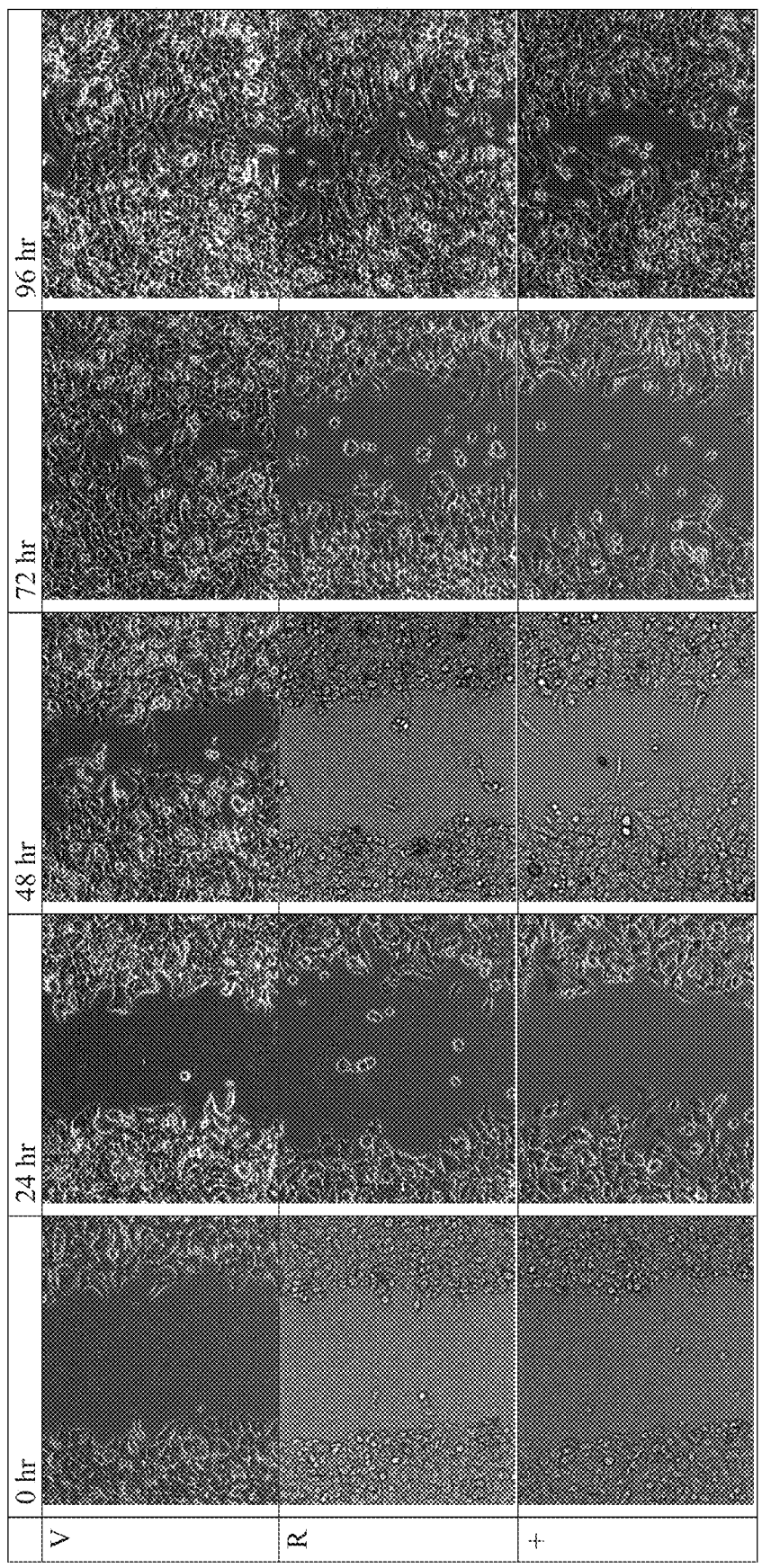
FIG. 55 shows is a series of photographs depicting the results of a wound-healing assay with regorafenib and the combination of regorafenib and milciclib in MHCC97H cells.
Figure 56:
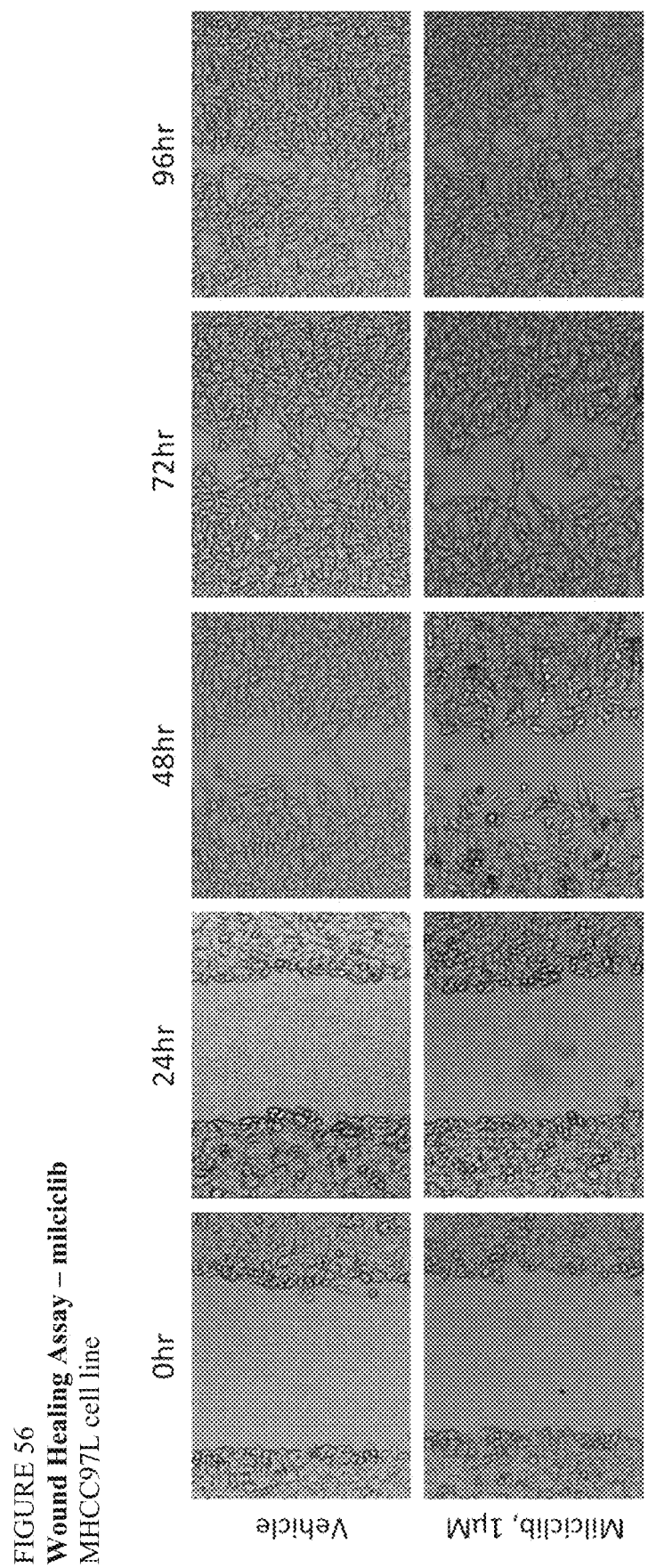
FIG. 56 is a series of photographs depicting the results of a wound-healing assay with milciclib in MHCC97L cells.
Figure 57:
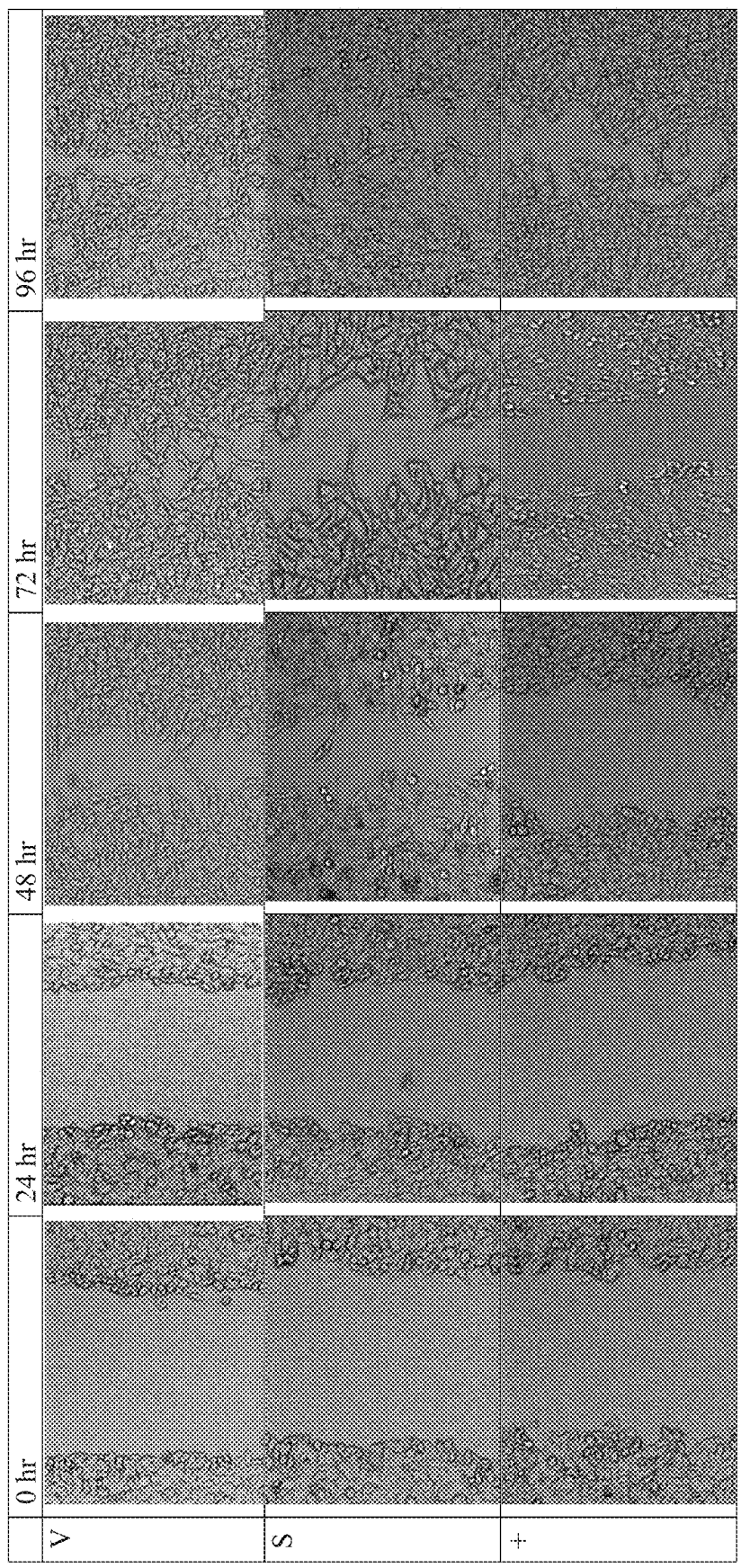
FIG. 57 is a series of photographs depicting the results of a wound-healing assay with sorafenib and the combination of sorafenib and milciclib in MHCC97L cells.
Figure 58:
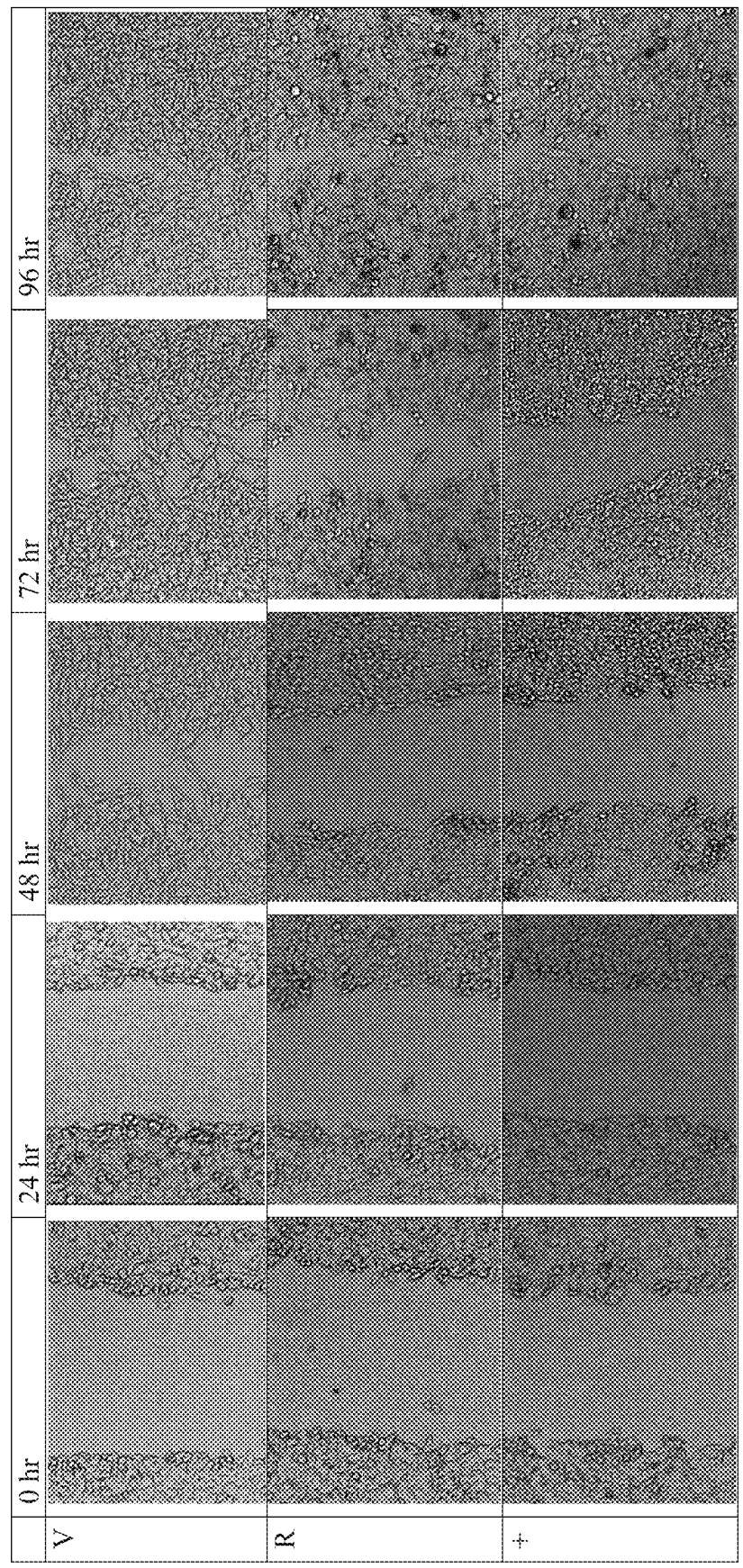
FIG. 58 is a series of photographs depicting the results of a wound-healing assay with sorafenib and the combination of regorafenib and milciclib in MHCC97L cells.
Figure 59:
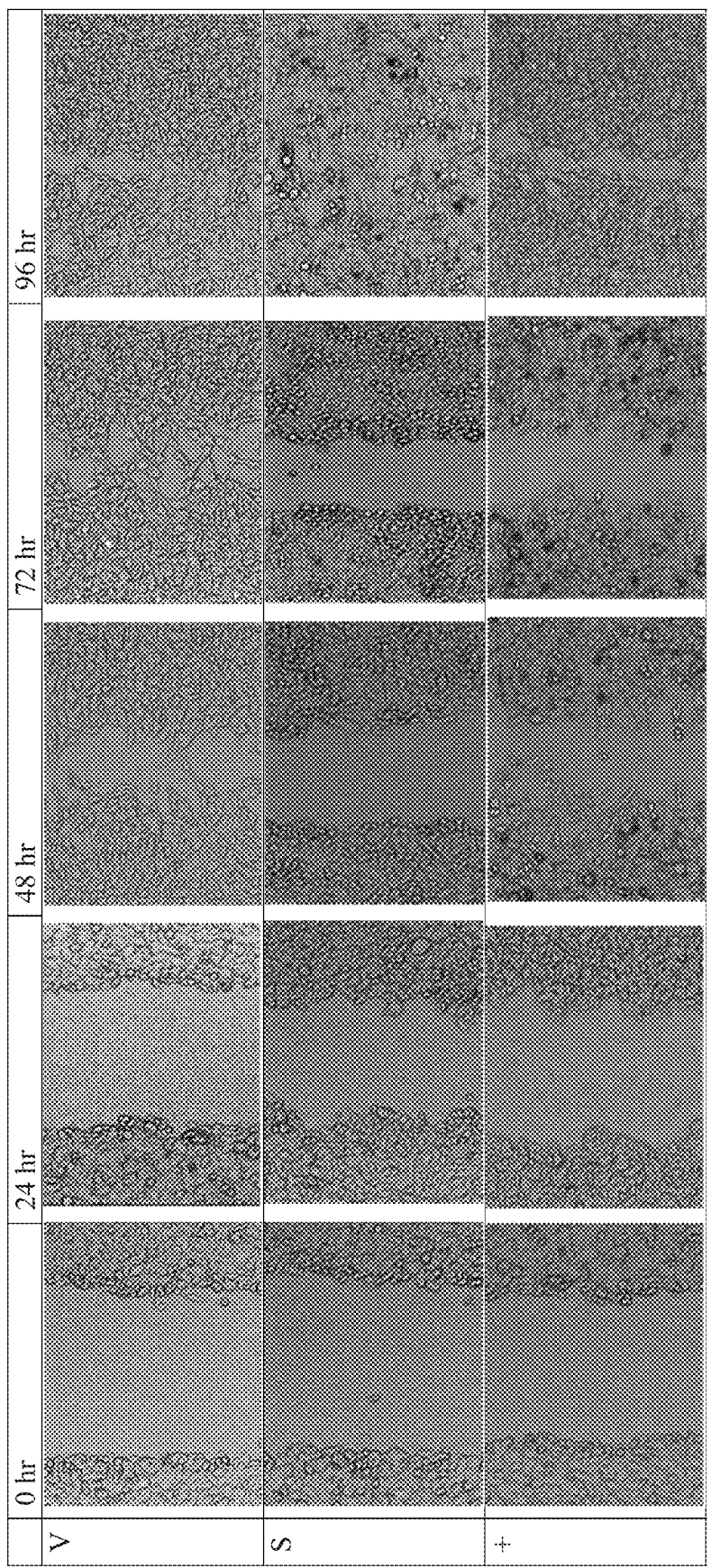
FIG. 59 is a series of photographs depicting the results of a wound-healing assay with sorafenib and the combination of sunitinib and milciclib in MHCC97L cells.
Figure 60:
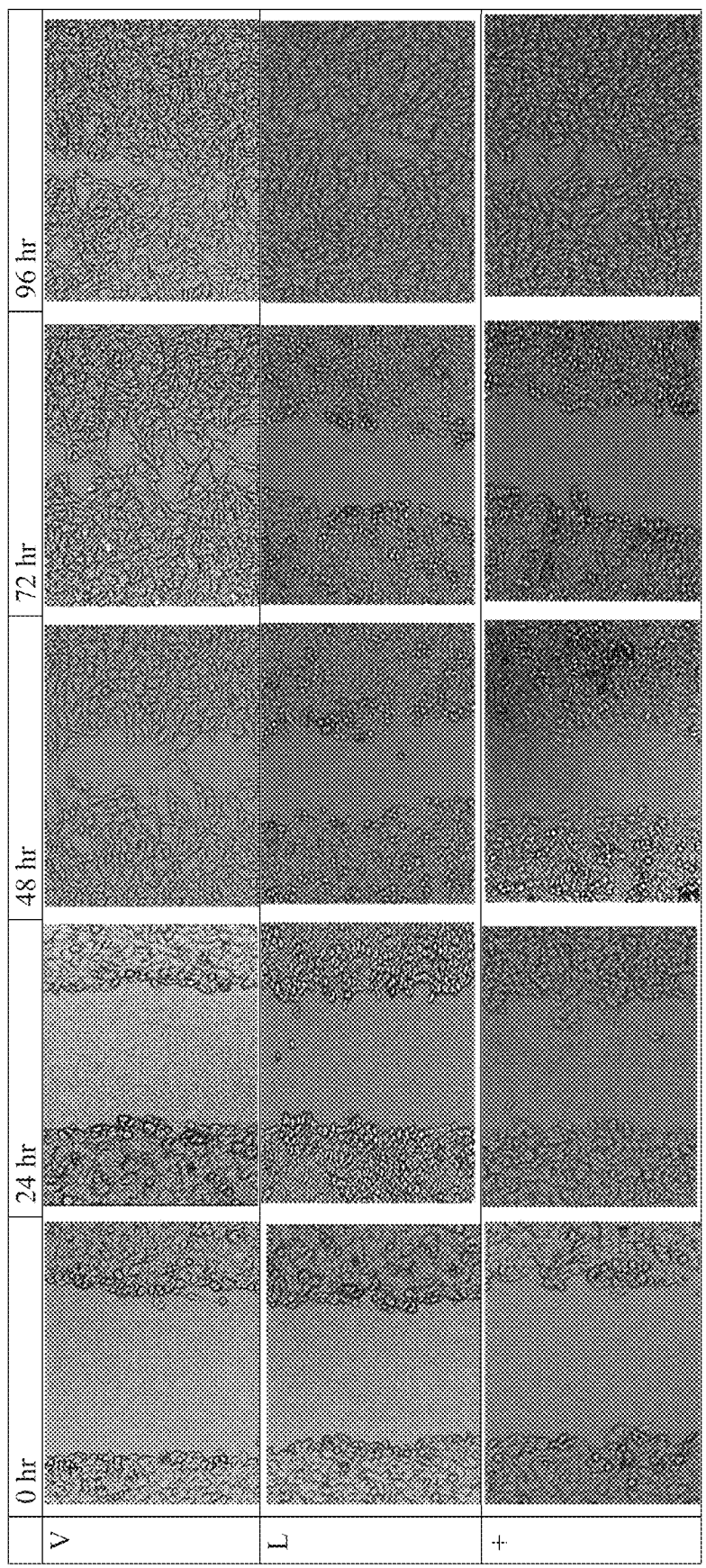
FIG. 60 is a series of photographs depicting the results of a wound-healing assay with sorafenib and the combination of lenvatinib and milciclib in MHCC97L cells.

MHCC97H cells were shown to produce human Alphafetoprotein (AFP) AFP ELISA Assay. Appreciably lower levels of AFP were detected in milciclib treated cells as compared to vehicle control (FIG. 30).

Promega ApoTox-Glo™ Triplex assays were also performed. Milciclib in combination with other TKIs at various concentrations decreased the cell viability and increased caspase 3/7 activity in MHCC97H cells (FIGS. 31-39) and MHCC97L cells (FIGS. 40-50) in a dose-dependent manner compared to those in vehicle-treated cells.

Figure 61:
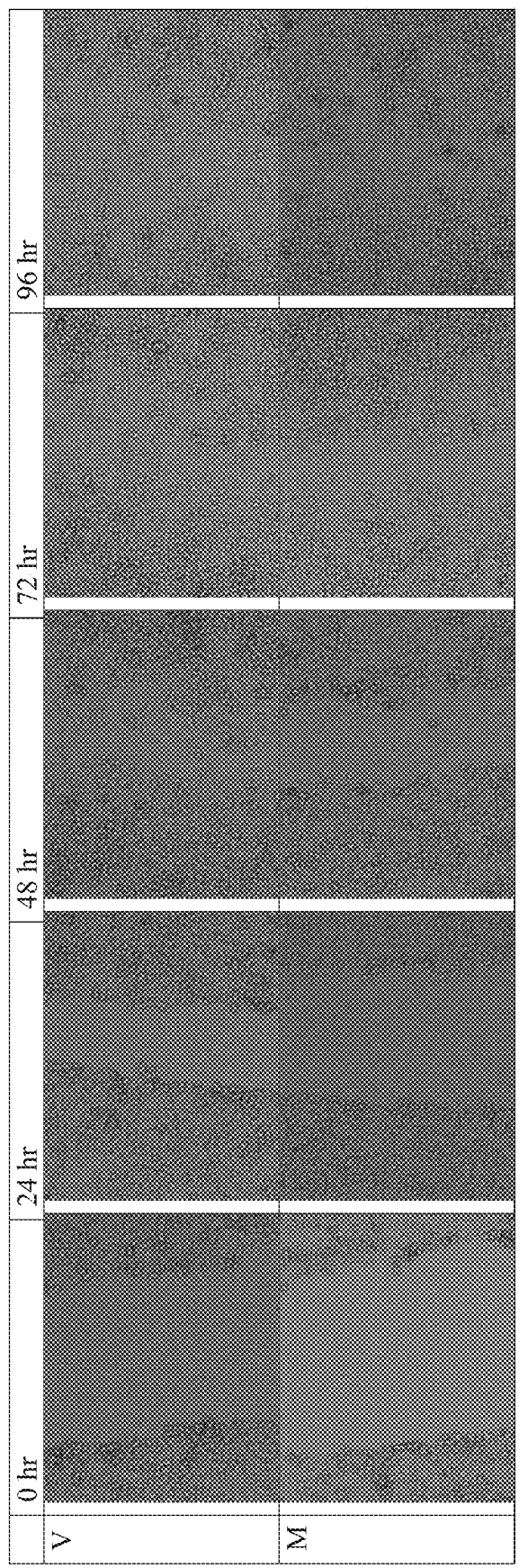
FIG. 61 is a series of photographs depicting the results of a wound-healing assay with milciclib in HepG2.2.15 cells.
Figure 62:
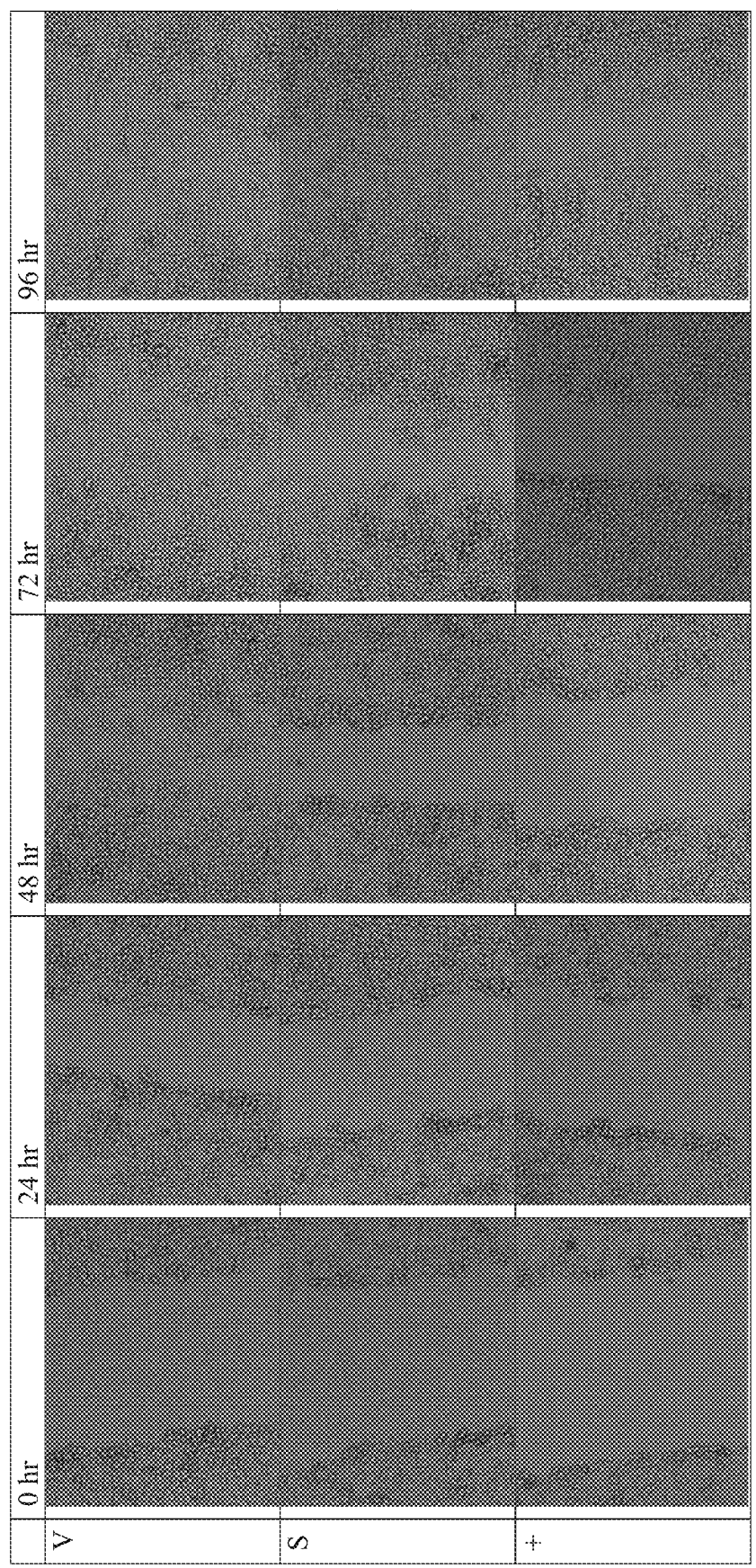
FIG. 62 is a series of photographs depicting the results of a wound-healing assay with sorafenib and the combination of sorafenib and milciclib in HepG2.2.15 cells.
Figure 63:
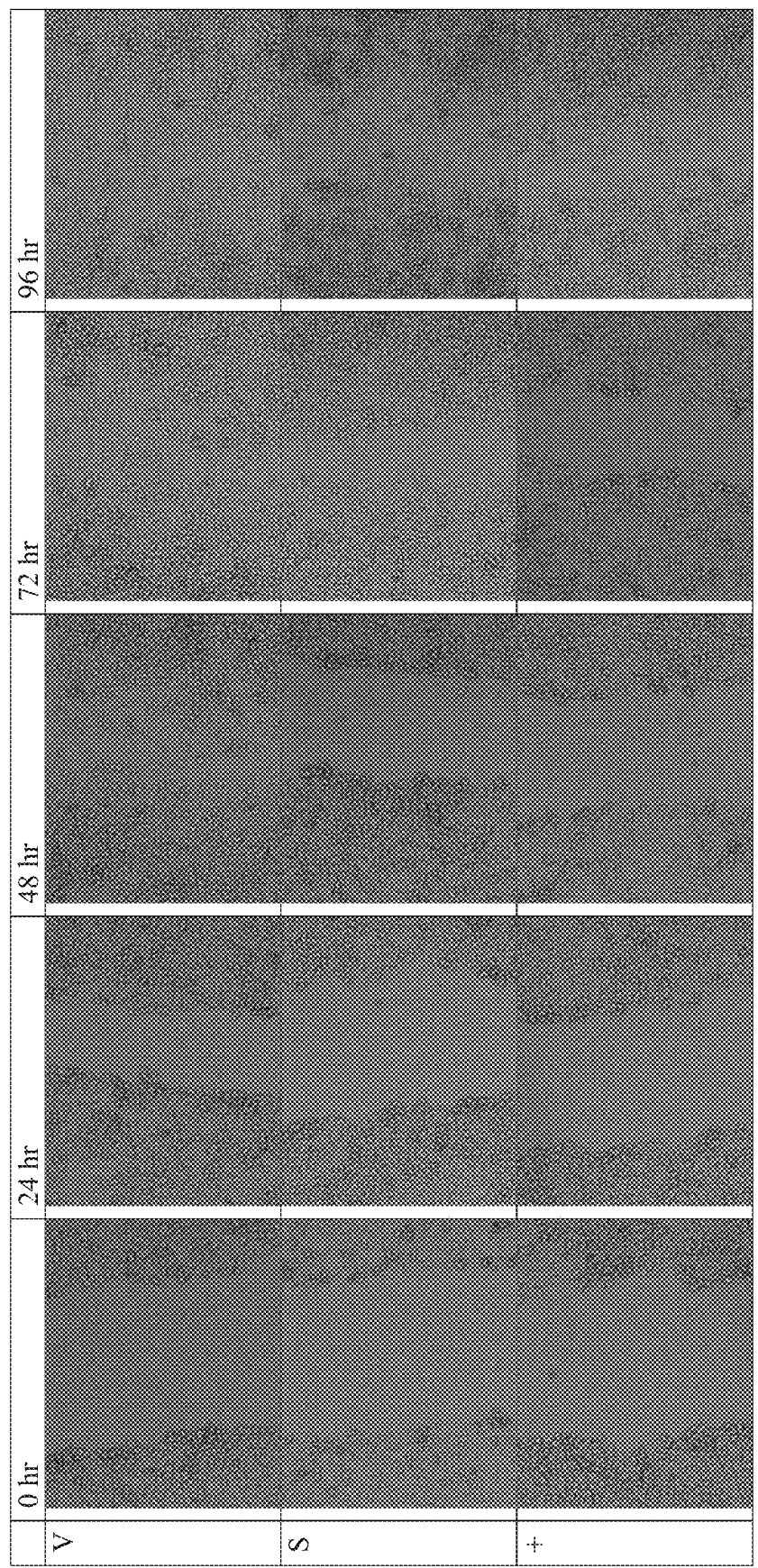
FIG. 63 is a series of photographs depicting the results of a wound-healing assay with regorafenib and the combination of regorafenib and milciclib in HepG2.2.15 cells.

Wound healing experiments were also performed. Treatment of scratched monolayer of MHCC97H cells with TKIs (tyrosine kinase inhibitors) in combination with milciclib (1.3 µM) for 96 h, reduced cell migration as compared to corresponding vehicle control (FIGS. 51-55). Treatment of scratched monolayer of MHCC97L cells with milciclib alone or in combination with other TKIs for 96 hours, reduced cell migration as compared to corresponding vehicle control (FIGS. 56-60). Treatment of scratched monolayer of HepG2.2.15 cells with milciclib alone or in combination with other TKIs for 96 hours, reduced cell migration as compared to corresponding vehicle control (FIGS. 61-63).

Figure 64:
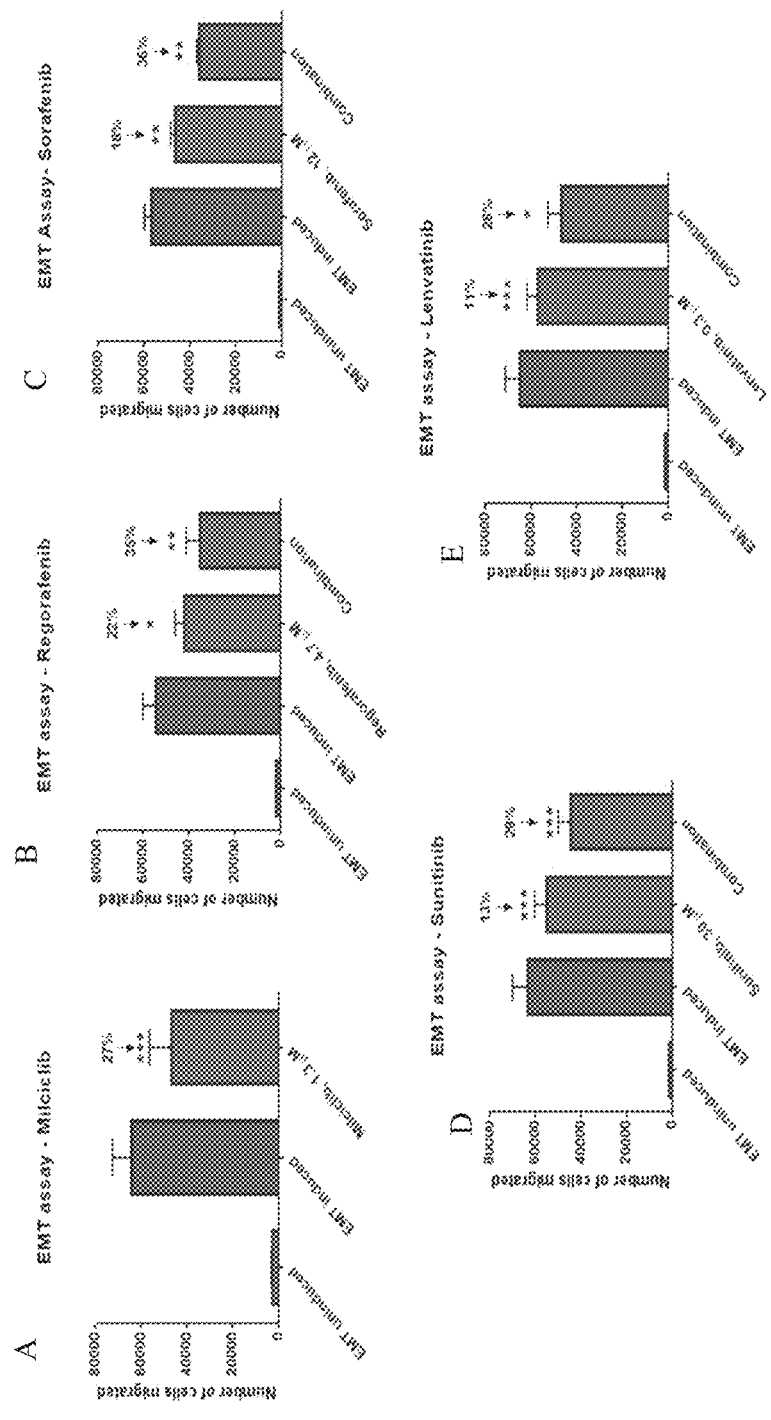
FIG. 64 is series of bar graphs displaying the results of an EMT assay with milciclib (A), regorafenib (B), sorafenib (C), sunitinib (D), and lenvatinib (E) in MHCC97L cells.
Figure 65:
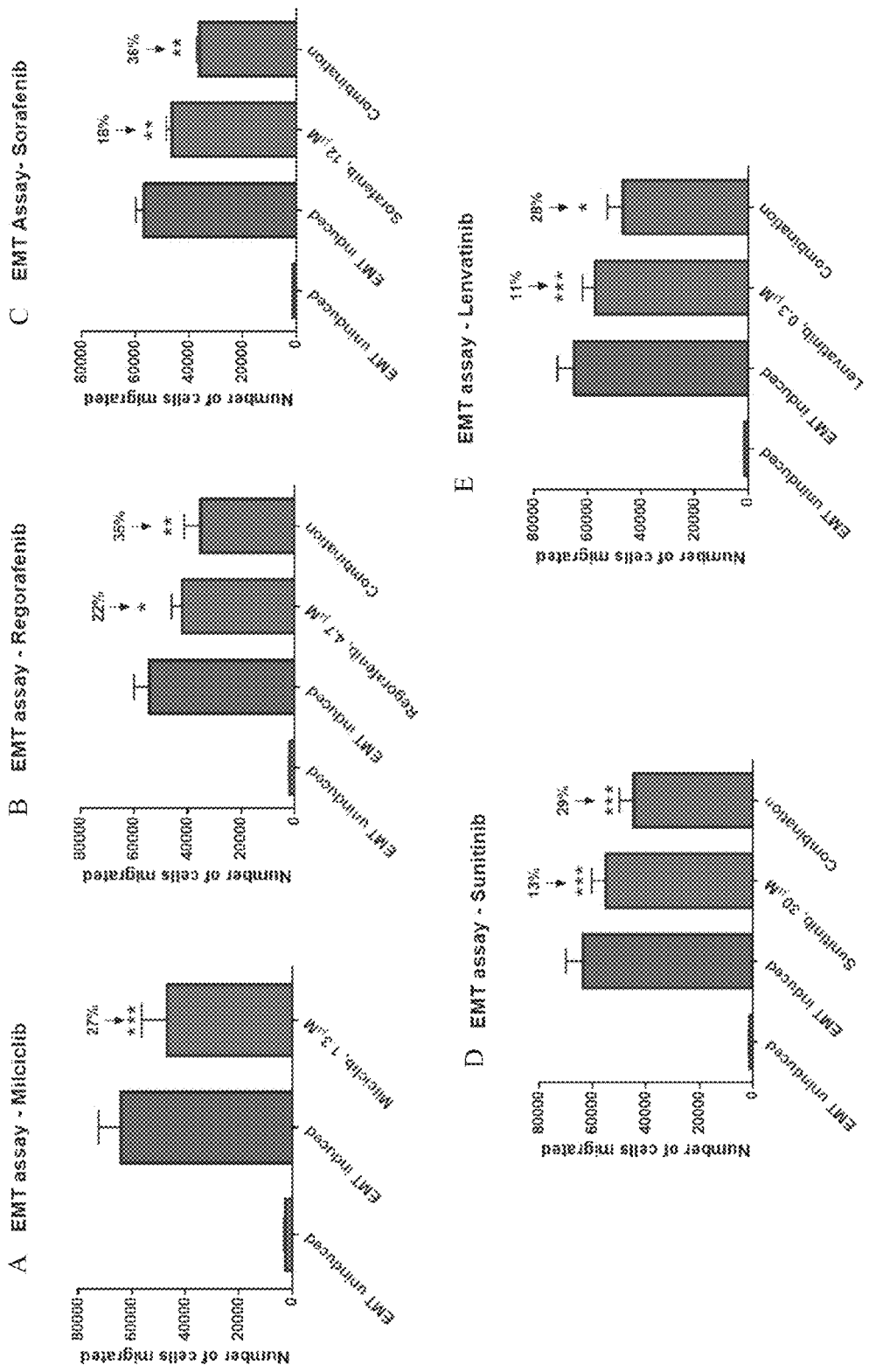
FIG. 65 is series of bar graphs displaying the results of an EMT assay with milciclib (A), regorafenib (B), sorafenib (C), sunitinib (D), and lenvatinib (E) in MHCC97H cells.

EMT (Epithelial to Mesenchymal Transition) assays were also performed. Regorafenib, sorafenib, sunitinib and lenvatinib in combination with milciclib reduced the invasion potential to a greater extent as compared to individual treatment (P<0.005) (FIG. 64). The inclusion of milciclib or TKIs alone resulted in statistically significant inhibition (P<0.05) in cell migration in MHCC97H cells. Regorafenib, sorafenib, sunitinib and lenvatinib in combination with milciclib reduced the invasion potential to a greater extent as compared to individual treatment (P<0.005), demonstrative of the anti-invasive potential of milciclib (FIG. 65).

Figure 67:
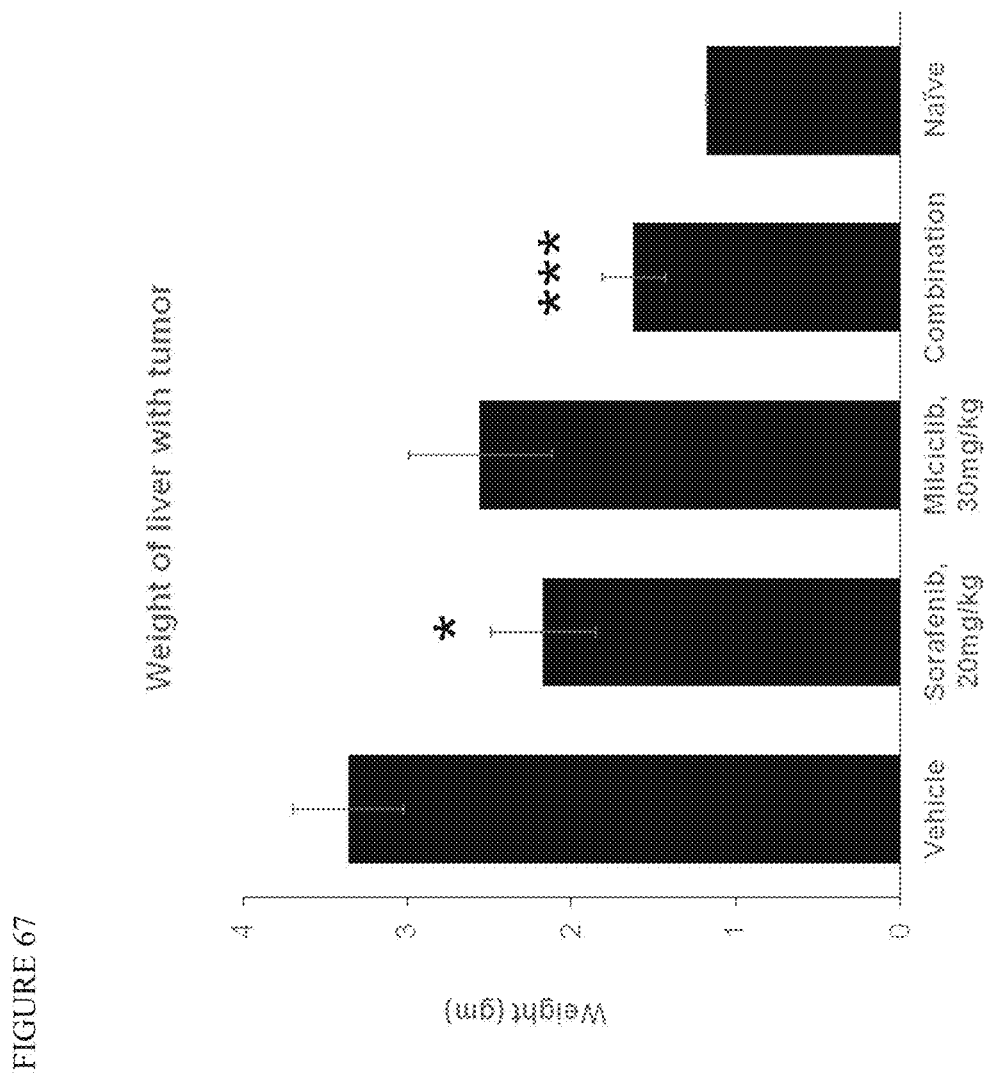
FIG. 67 is a graph showing weight of mice livers following treatment via oral administration with sorafenib, milciclib, sorafenib+milciclib.
Figure 68:
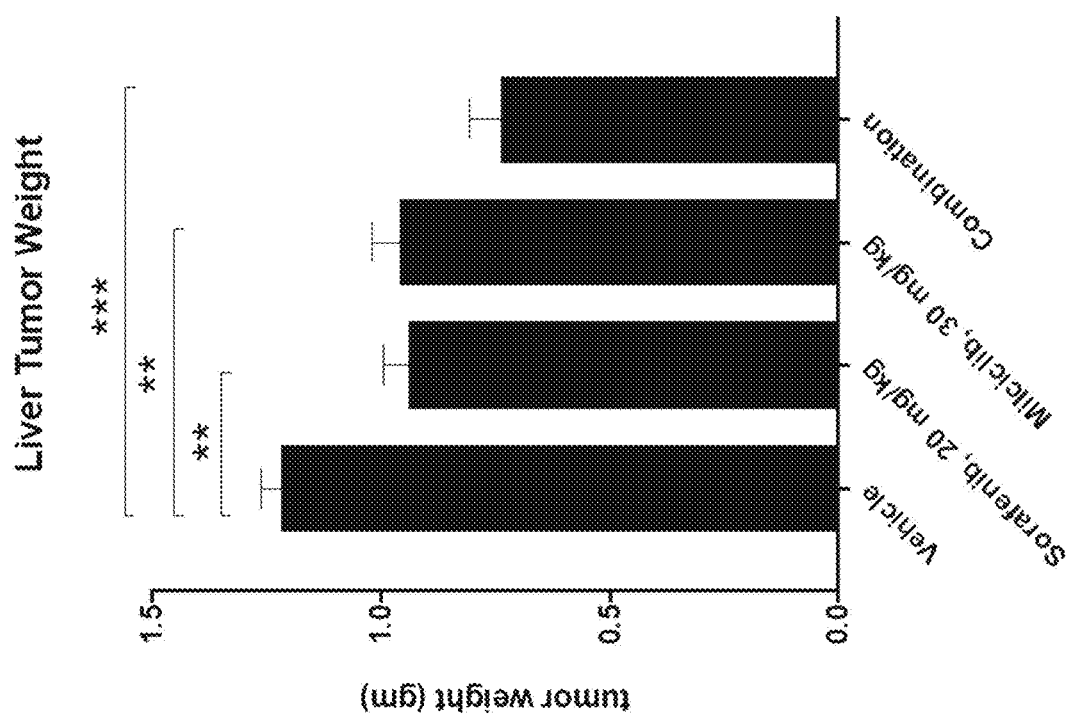
FIG. 68 is a graph showing weight of mice liver tumors following treatment via oral administration with sorafenib, milciclib, sorafenib+milciclib.
Figure 69:
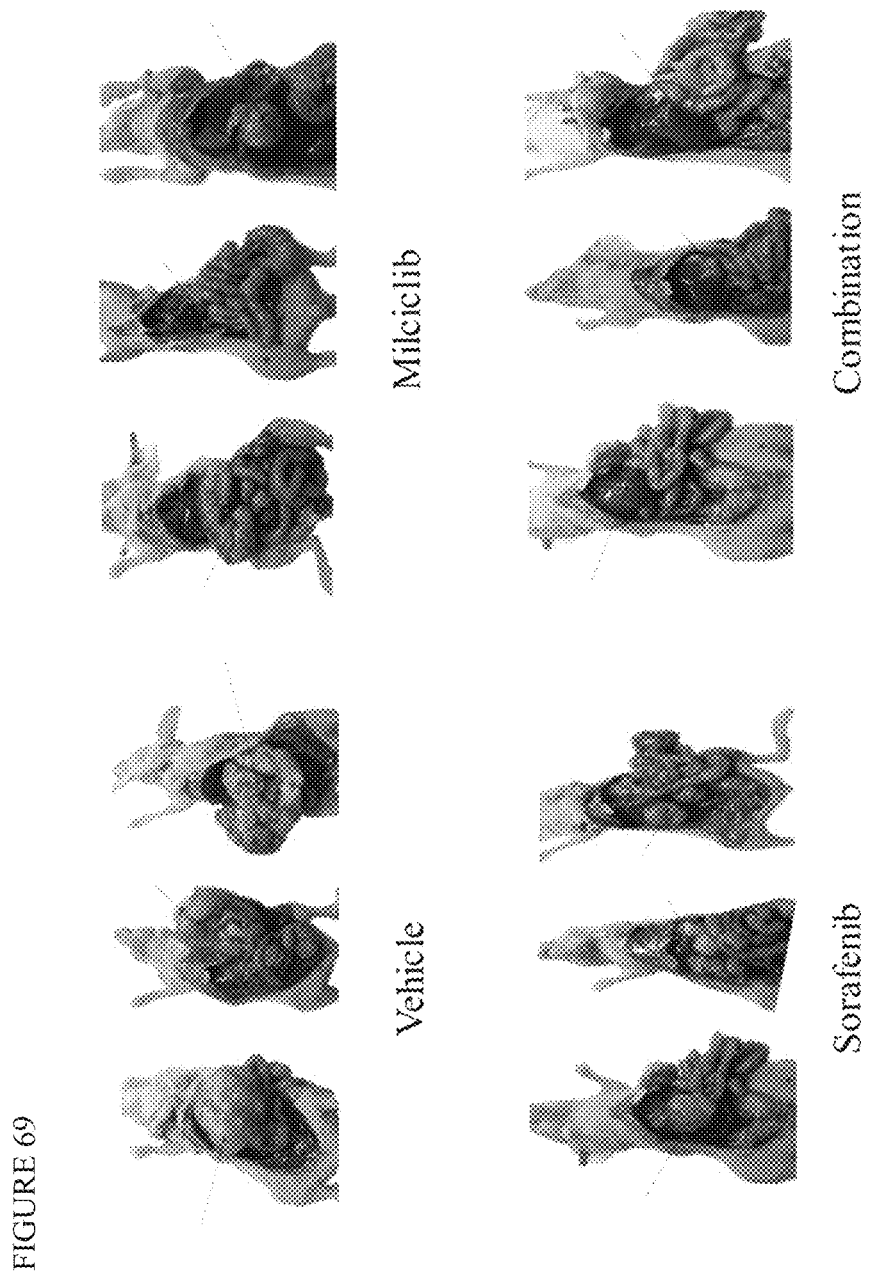
FIG. 69 is a series of photographs depicting changes in MHCC97H orthotopic HCC mouse liver tumor burden following treatment with vehicle, milciclib, sorafenib, or milciclib+sorafenib.
Figure 70:
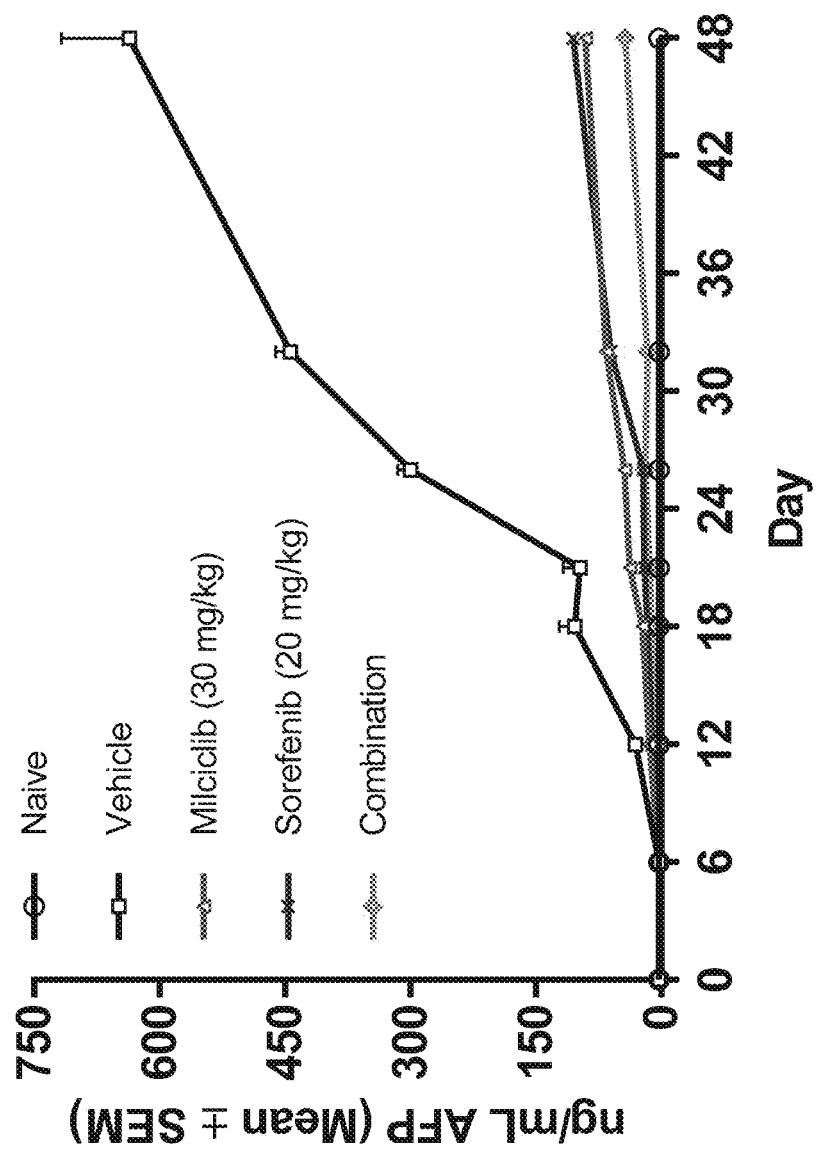
FIG. 70 is a graph depicting changes in AFP serum levels in athymic mice with livers injected with MHCC97H cells were treated with vehicle, sorafenib, milciclib, or milciclib+sorafenib.

Mouse experiments (tumor induction) were performed. Oral administration of milciclib (30 mg/kg/day) either alone or in combination with sorafenib (20 mg/kg/day) produced synergistic effect in reducing tumor growth [milciclib—20% (p<0.002) or sorafenib—21% (p<0.001) vs combination—38% (p<0.0002) as compared to vehicle (FIG. 67). Vehicle group had more liver weight but with combination the liver weight goes down (FIG. 68). Pictures were taken showing the difference in tumor burden with the treatment of milciclib, sorafenib, and the combination. Vehicle group has an enlarged tumor but with the combination, the tumor burden goes down (FIG. 69). A steady increase in serum AFP was observed in vehicle administered animals until the end of the study. Significantly lower serum AFP levels were recorded for animals treated with milciclib (30 mg/kg), sorafenib (20 mg/kg) alone or in combination (FIG. 70).

Figure 71A:
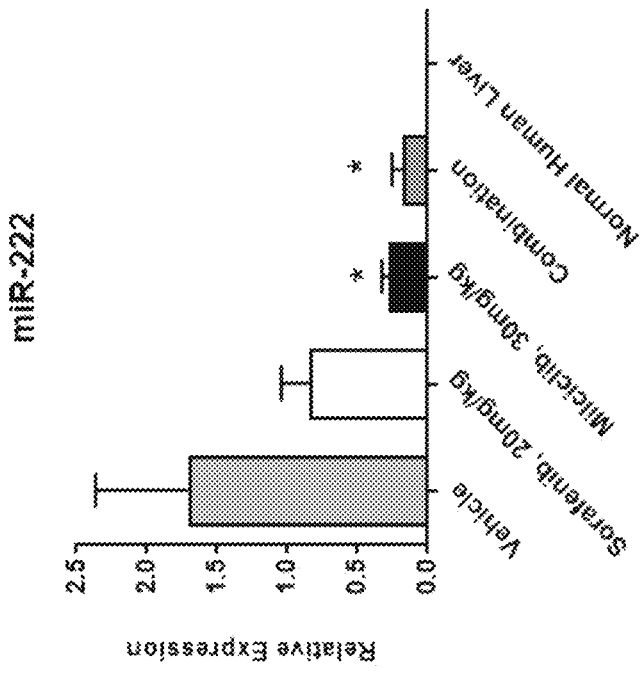
FIGS. 71A and 71B are a series of graphs depicting relative expression of miR-221 (71A) and miR-222 (71B) miRNAs in athymic mice with livers injected with MHCC97H cells treated with vehicle, sorafenib, milciclib, or milciclib+sorafenib.
Figure 71B:
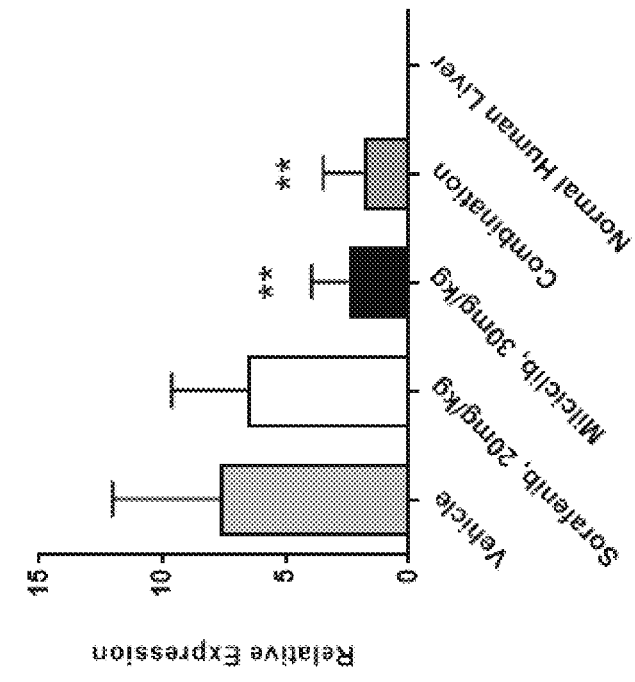

It was determined that milciclib acts via specifically downregulating miR221/222. Gene expression studies suggest that milciclib possibly exerts its action through downregulation of miR-221 and miR-222. Data suggest that oral treatment with milciclib exerts its activity via downregulation of miR-221 and miR-222 (FIGS. 71A and 71B). These data suggest that milciclib specifically acts via reducing expression of miR-221 and miR-222, which are known to be major culprits of hepatocarcinogenesis.

Figure 72:
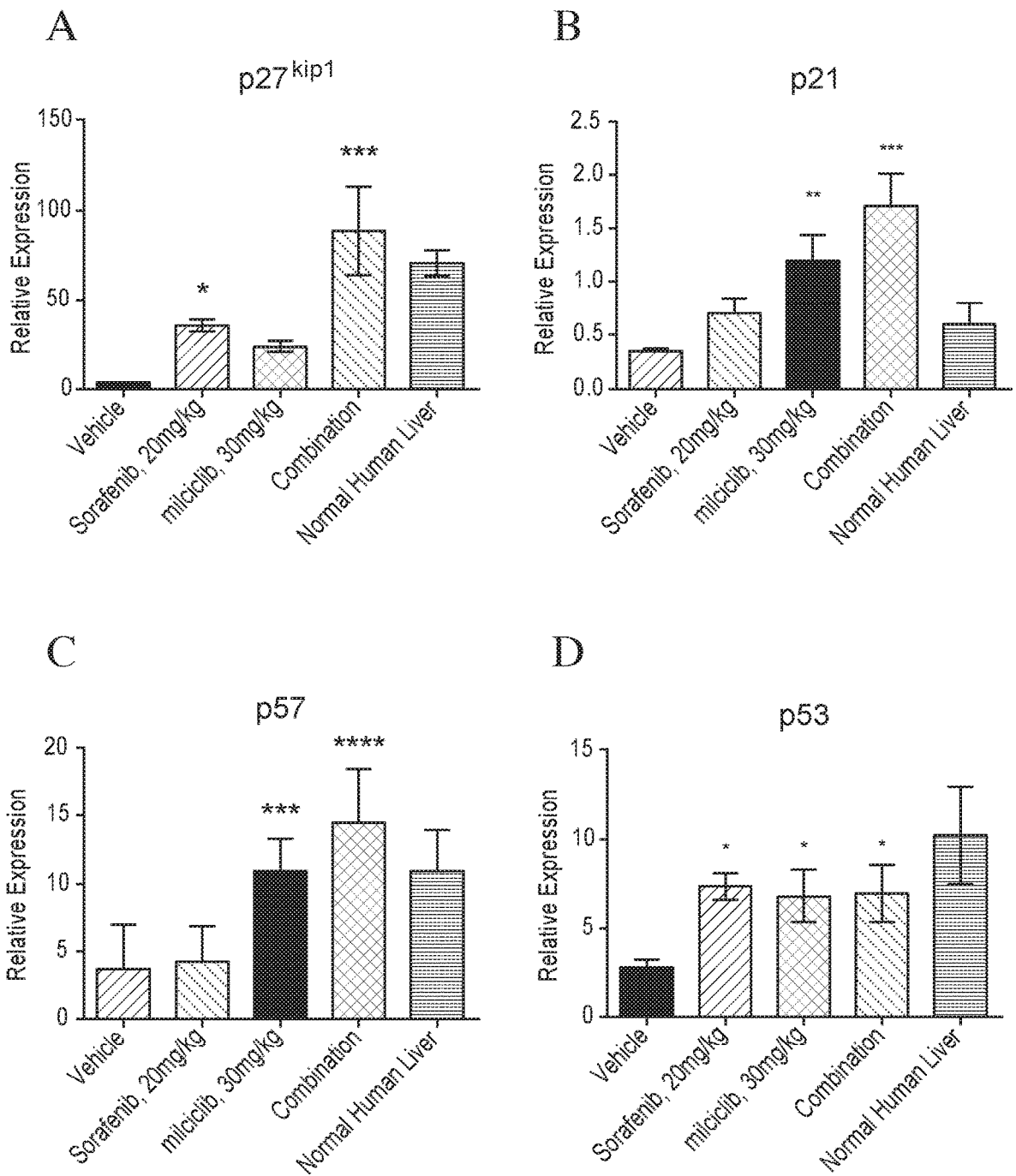
FIG. 72 is a series of graphs depicting relative expression of p27$^{kip1}$(A), p21 (B), p57 (C), and p53 (D) in athymic mice with livers injected with MHCC97H cells following treatment with vehicle, sorafenib, milciclib, or milciclib+sorafenib.
Figure 73B:
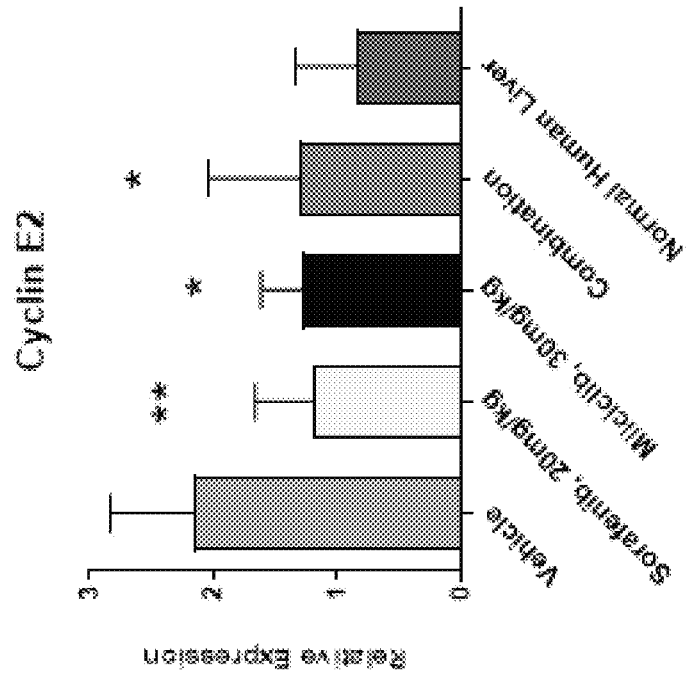
FIGS. 73A and 73B are a series of graphs depicting relative expression of Cyclin D1 (73A) and Cyclin E2 (73B) in athymic mice with livers injected with MHCC97H cells following treatment with vehicle, sorafenib, milciclib, or milciclib+sorafenib.
Figure 73A:
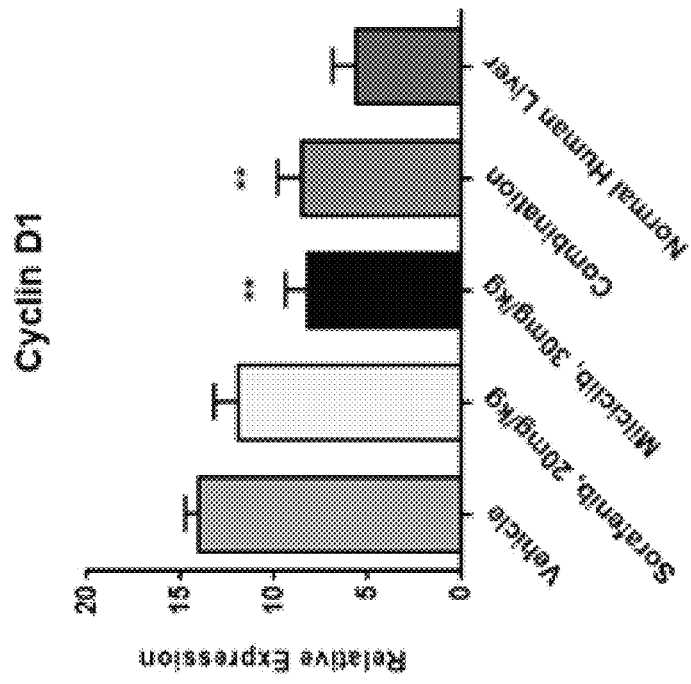

Mechanism of action studies with milciclib were also performed. The mechanism of action of milciclib appears to be distinct from the mechanism of action of sorafenib as it upregulated the expression of tumor suppressors such as p27, p21, p53 and p57 (FIGS. 72A, B, C, D). Oral administration of milciclib alone or in combination with sorafenib downregulated expression of cyclins such as cyclin E2 and cyclin D1 (FIGS. 73A and 73B). Oral administration of milciclib alone or in combination with sorafenib downregulated expression of cell proliferation genes such as MKI67, cdc6, c-Myc (FIGS. 74A, 74B, 74C). The mechanism of action of milciclib appears to be distinct from the mechanism of action of sorafenib.

Figure 75:
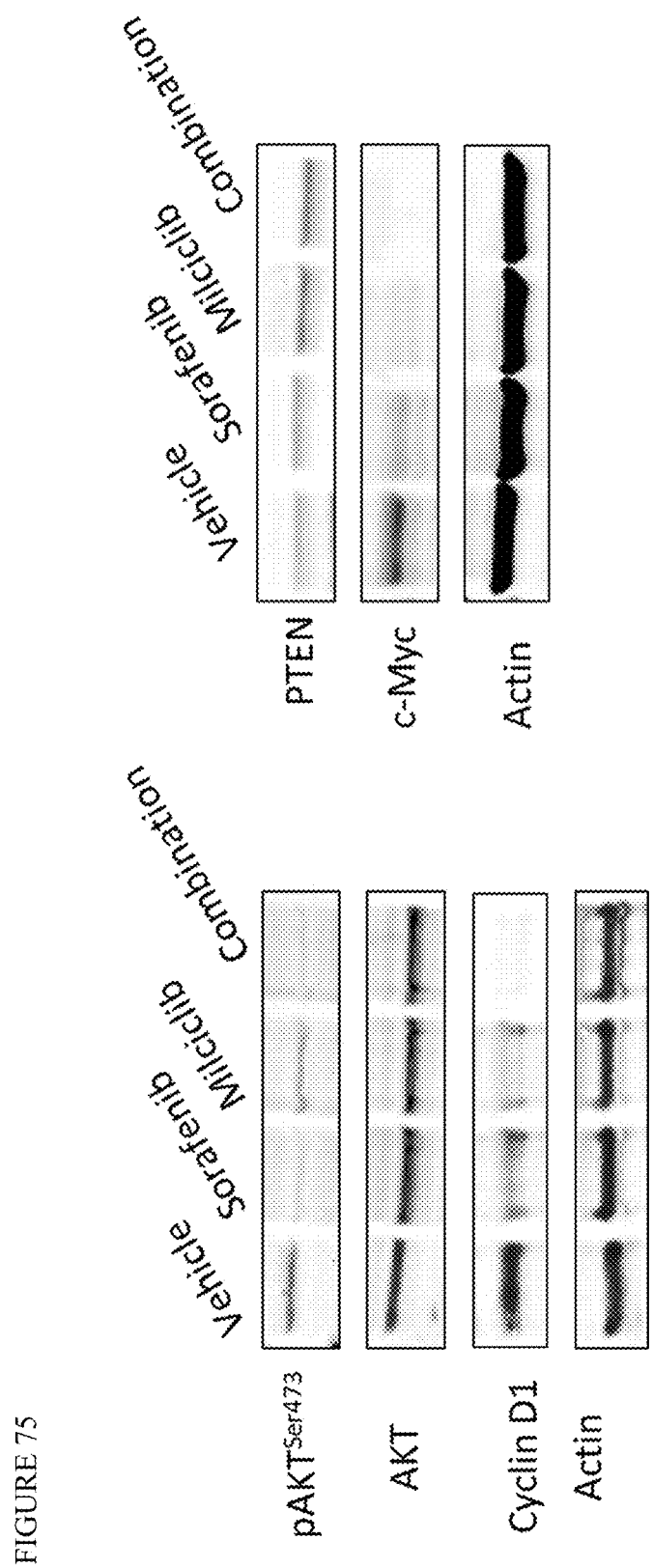
FIG. 75 is a series of western blots depicting changes in expression of pAKT$^{Ser473}$, AKT, Cyclin D1, c-Myc, and PTEN in cells cultured from orthotopic HCC model mice following treatment with vehicle, sorafenib, milciclib, or milciclib+sorafenib. Actin is used as a loading control.

Mechanistic studies revealed a reduction in pAKT, c-Myc and cyclin D1 expression and upregulation of PTEN in liver samples derived from milciclib and milciclib and sorafenib administered animals as compared to vehicle treated group (FIG. 75). Data from cell culture studies and from orthotopic HCC model in nude mice suggest that oral treatment with milciclib exerts its activity via a new mechanism.

Hepatocellular Carcinoma (HCC)

Figure 76:
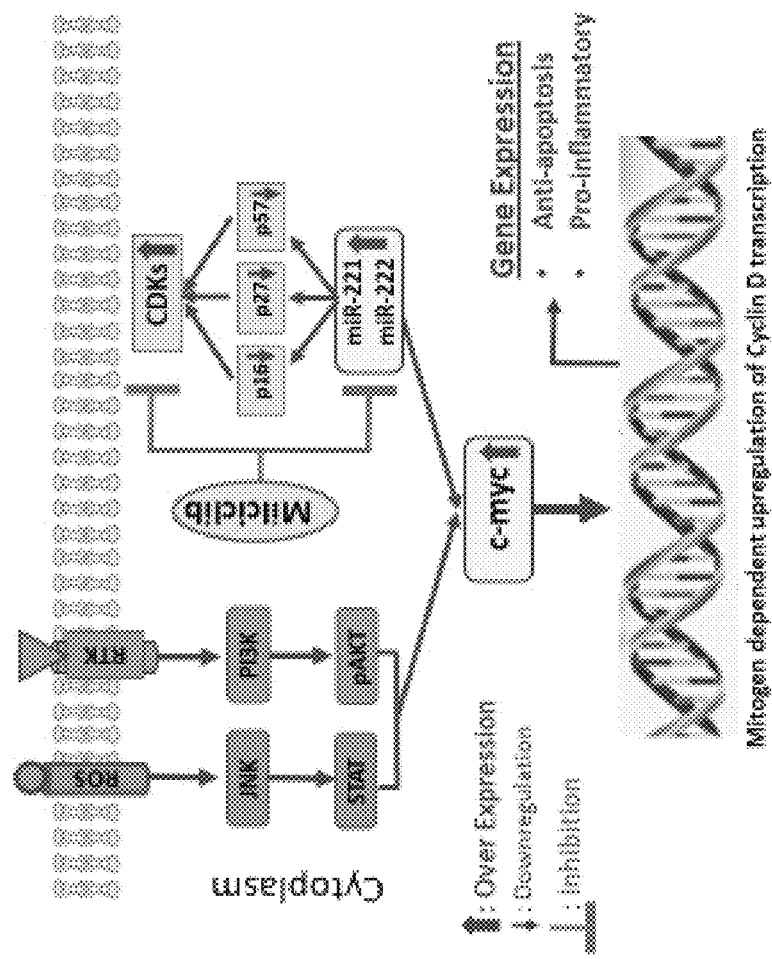
FIG. 76 is a schematic depicting milciclib mechanism of action in hepatocellular carcinoma.

Hepatocellular carcinoma (HCC) is an extremely complex multi-factorial condition associated with many confounding factors affecting disease course and patient prognosis. A broad range of mechanisms, including telomere dysfunction, activation of oncogenic pathways, abrogation of DNA damage checkpoints, activation of pro-inflammatory and metastatic pathways, and induction of the oxidative stress response. Consequently, HCC is typically associated with overexpression of receptor tyrosine kinases (RTK) and excessive oxidative stress (ROS). Collectively, overexpression of RTK and ROS lead to increased expression of c-myc, resulting in high metastatic potentials of hepatocytes. Thus, metastatic potential of hepatocytes can be reduced with specific inhibitors of RTK. On the other hand, HCC is also associated with overexpression of miR-221, miR-222 and CDKs, resulting in dysregulation of cell cycle, which leads to excessive proliferation of hepatocytes. Treatment with milciclib is known to inhibit miR-221/miR-222 and a number of CDKs and it can effectively reduce proliferation of hepatocytes. Therefore, collectively combination of milciclib with an inhibitor of RTK may produce synergistic effect in reducing expression of c-myc and in total tumor growth and progression. Thus, an effective therapy for HCC needs to control proliferation of hepatocytes and also suppress their metastatic potential. (FIG. 76)

Pharmaceutical Compositions and Formulations

A pharmaceutical composition of the application is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the application can be administered to a subject in many of the well-known methods currently used for chemotherapeutic treatment. For example, for treatment of cancers, a compound of the application may be injected directly into tumors, injected into the blood stream or body cavities or taken orally or applied through the skin with patches. The dose chosen should be sufficient to constitute effective treatment but not so high as to cause unacceptable side effects. The state of the disease condition and the health of the patient should preferably be closely monitored during and for a reasonable period after treatment.

The term "therapeutically effective amount," as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

The therapeutically effective amount of milciclib is 1-500 mg administered one or more times over a day for up to 30 or more days, followed by 1 or more days of non-administration of milciclib. This type of treatment schedule, i.e., administration of milciclib on consecutive days followed by non-administration of milciclib on consecutive days may be referred to as a treatment cycle. A treatment cycle may be repeated as many times as necessary to achieve the intended affect.

In one embodiment, the therapeutically effective amount of milciclib is 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, or 500 mg once or twice daily for one, two, three, four, five, six, seven, eight, nine, ten, eleven, twelve, thirteen, fourteen, or fifteen consecutive days, followed by non-administration for one, two, three, four, five, six, or seven consecutive days, wherein the cycle is optionally repeated 1, 2, or 3 times.

In one embodiment, the therapeutically effective amount of milciclib is 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 mg once or twice daily for one, two, three, four, five, six, seven, eight, nine, or ten consecutive days, followed by non-administration for one, two, three, four, five, six, or seven consecutive days, wherein the cycle is optionally repeated 1, 2, or 3 times.

In one embodiment, the therapeutically effective amount of milciclib is 40, 45, 50, 55, 60, 65, 70, 75, 80, 85, 90, 95, 100, 105, 110, 115, 120, 125, 130, 135, 140, 145, or 150 mg once or twice daily for one, two, three, four, five, six, or seven consecutive days, followed by non-administration for one, two, three, four, five, six, or seven consecutive days, wherein the cycle is optionally repeated 1, 2, or 3 times.

In one embodiment, the therapeutically effective amount of milciclib is 75, 80, 85, 90, 95, 100, 105, 110, 115, 120, or 125 mg once daily for four consecutive days, followed by non-administration for three consecutive days, wherein the cycle is optionally repeated 1, 2, or 3 times.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between toxic and therapeutic effects is the therapeutic index, and it can be expressed as the ratio, LD50/ED50. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present application may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one aspect, the active compounds are prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the application are dictated by and directly dependent on the unique characteristics of the active compound and the particular therapeutic effect to be achieved.

In therapeutic applications, the dosages of the pharmaceutical compositions used in accordance with the application vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 3000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in m2, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can include co-formulations of milciclib and any of the compounds described herein.

The pharmaceutical compositions can be included in a container, pack, or dispenser together with instructions for administration.

The present application also relates to the following:

A. A method of treating or preventing cancer in a patient in need thereof, comprising administering to the patient a therapeutically effective amount of milciclib, or a pharmaceutically acceptable salt, isomer, or tautomer thereof, in combination with a therapeutically effective amount of another anticancer drug selected from the group consisting of sorafenib, lenvatinib, regorafenib, sunitinib, nivolumab, gemcitabine, and palbociclib, or a pharmaceutically acceptable salt thereof.

B. A method of treating or preventing non-small cell lung cancer, renal cell carcinoma, hepatocellular carcinoma, thyroid carcinoma, colorectal cancer, gastrointestinal stromal tumors, breast cancer, prostate cancer, pancreatic cancer, or thymoma in a patient in need thereof, comprising administering to the patient a therapeutically effective amount of milciclib, or a pharmaceutically acceptable salt, isomer, or tautomer thereof, in combination with a therapeutically effective amount of another anticancer drug.

C. A method of treating or preventing non-small cell lung cancer, renal cell carcinoma, hepatocellular carcinoma, thyroid carcinoma, colorectal cancer, gastrointestinal stromal tumors, breast cancer, prostate cancer, pancreatic cancer, or thymoma in a patient in need thereof, comprising administering to the patient a therapeutically effective amount of milciclib, or a pharmaceutically acceptable salt, isomer, or tautomer thereof, in combination with a therapeutically effective amount of another anticancer drug selected from the group consisting of sorafenib, lenvatinib, regorafenib, sunitinib, nivolumab, gemcitabine, and palbociclib.

D. Any of methods disclosed herein, wherein the other anticancer drug is sorafenib or a pharmaceutically acceptable salt thereof. In one embodiment, the therapeutically effective amount of sorafenib is 400 mg twice daily, 200 mg twice daily, or 200 mg once daily. In one embodiment, the cancer is renal cell carcinoma, hepatocellular carcinoma, or thyroid carcinoma.

E. Any of methods disclosed herein, wherein the other anticancer drug is lenvatinib or a pharmaceutically acceptable salt thereof. In one embodiment, the therapeutically effective amount of lenvatinib is 8, 10, 12, 14, 18, 20, 22, 24, 26, 28, 30, 32, or 34 mg once daily. In one embodiment, the cancer is renal cell carcinoma or thyroid carcinoma.

F. Any of methods disclosed herein, wherein the other anticancer drug is regorafenib or a pharmaceutically acceptable salt thereof. In one embodiment, the therapeutically effective amount of regorafenib is 80, 100, or 120 mg once daily for three weeks, followed by one week of no administration, wherein the cycle is optionally repeated. In one embodiment, the cancer is colorectal cancer or gastrointestinal stromal tumors.

G. Any of methods disclosed herein, wherein the other anticancer drug is sunitinib or a pharmaceutically acceptable salt thereof. In one embodiment, the therapeutically effective amount of sunitinib is 12.5, 25, 37.5, 50, 62.5, 75, 87.5, or 100 mg once daily continuously or for 4 weeks followed by two weeks of no administration, wherein the cycle is optionally repeated. In one embodiment, the cancer is renal cell carcinoma or gastrointestinal stromal tumors.

H. Any of methods disclosed herein, wherein the other anticancer drug is nivolumab. In one embodiment, the cancer is non-small cell lung cancer or renal cell carcinoma.

I. Any of methods disclosed herein, wherein the other anticancer drug is palbociclib or a pharmaceutically acceptable salt thereof. In one embodiment, the therapeutically effective amount of palbociclib is 75, 100, or 125 mg once daily for 3 weeks followed by one week of no administration, wherein the cycle is optionally repeated. In one embodiment, the cancer is breast cancer.

J. Any of methods disclosed herein, wherein the other anticancer drug is gemcitabine. In one embodiment, the therapeutically effective amount of gemcitabine is 1000 mg/m$^2$ over 30 minutes once weekly for seven weeks, followed by one week of no administration, wherein the cycle is optionally repeated. In one embodiment, the cancer is breast cancer.

K. Any of methods disclosed herein, wherein the therapeutically effective amount of milciclib is 50, 75, 100, 125, or 150 mg once daily for four consecutive days, followed by non-administration for 3 consecutive days, wherein the cycle is optionally repeated. For example, the therapeutically effective amount of milciclib is 50, 75, 100, 125, or 150 mg once daily for four consecutive days, followed by non-administration for 3 consecutive days, wherein the cycle is repeated as multiple times, e.g., 1, 2, 3, 4, 5, 6, 7, 8, or more times. For example, the therapeutically effective amount of milciclib is about 100 mg once daily for four consecutive days, followed by non-administration for 3 consecutive days, wherein the cycle is optionally repeated. For example, the therapeutically effective amount of milciclib is 100 mg once daily for four consecutive days, followed by non-administration for 3 consecutive days, wherein the cycle is optionally repeated.

L. Any of methods disclosed herein, wherein milciclib and the other anticancer drug are administered to the patient simultaneously.

M. Milciclib and the other anticancer drug are administered in a single pharmaceutical formulation that further includes a pharmaceutically acceptable excipient. In one embodiment, wherein the pharmaceutical formulation is in a controlled release form.

N. Milciclib and the other anticancer drug are each administered in separate pharmaceutical formulations, wherein each formulation further includes a pharmaceutically acceptable excipient. In one embodiment, one or both of the pharmaceutical formulations is in a controlled release form.

O. Any of methods disclosed herein, wherein milciclib and the other anticancer drug are administered to the patient sequentially. In one embodiment, the administration of milciclib begins before administration of the other anticancer drug to the patient. In one embodiment, the administration of milciclib begins after administration of the other anticancer drug to the patient.

P. Milciclib is administered in a single pharmaceutical formulation that further includes a pharmaceutically acceptable excipient. In one embodiment, the other anticancer drug is administered in a single pharmaceutical formulation that further includes a pharmaceutically acceptable excipient. In one embodiment, any of the pharmaceutical formulations are formulated for oral administration. For example, in one embodiment, the pharmaceutical formulation is in the form of a tablet, pill, or capsule.

Q. Any of methods disclosed herein, wherein the method of treating or preventing renal cell carcinoma in a patient in need thereof comprising administering to the patient a therapeutically effective amount of milciclib, or a pharmaceutically acceptable salt, isomer, or tautomer thereof, in combination with a therapeutically effective amount of sorafenib.

R. Any of methods disclosed herein, wherein the therapeutically effective amount of sorafenib is 400 mg twice daily, 200 mg twice daily, or 200 mg once daily.

S. Any of methods disclosed herein, wherein the therapeutically effective amount of milciclib is 50, 75, 100, 125, or 150 mg once daily for four consecutive days, followed by non-administration for 3 consecutive days, wherein the cycle is optionally repeated.

T. Any of methods disclosed herein, wherein the method of treating or preventing hepatocellular carcinoma in a patient in need thereof comprising administering to the patient a therapeutically effective amount of milciclib, or a pharmaceutically acceptable salt, isomer, or tautomer thereof, in combination with a therapeutically effective amount of sorafenib.

U. Any of methods disclosed herein, wherein the therapeutically effective amount of sorafenib is 400 mg twice daily, 200 mg twice daily, or 200 mg once daily.

V. Any of methods disclosed herein, wherein the therapeutically effective amount of milciclib is 50, 75, 100, 125, or 150 mg once daily for four consecutive days, followed by non-administration for 3 consecutive days, wherein the cycle is optionally repeated.

W. A method of treating or preventing thyroid carcinoma in a patient in need thereof comprising administering to the patient a therapeutically effective amount of milciclib, or a pharmaceutically acceptable salt, isomer, or tautomer thereof, in combination with a therapeutically effective amount of sorafenib.

X. Any of methods disclosed herein, wherein the therapeutically effective amount of sorafenib is 400 mg twice daily, 200 mg twice daily, or 200 mg once daily.

Y. Any of methods disclosed herein, wherein the therapeutically effective amount of milciclib is 50, 75, 100, 125, or 150 mg once daily for four consecutive days, followed by non-administration for 3 consecutive days, wherein the cycle is optionally repeated.

Z. Any of methods disclosed herein, wherein milciclib and sorafenib are administered to the patient simultaneously.

AA. Any of methods disclosed herein, wherein milciclib and sorafenib are administered in a single pharmaceutical formulation that further includes a pharmaceutically acceptable excipient.

BB. Any of methods disclosed herein, wherein the pharmaceutical formulation is in a controlled release form.

CC. Any of methods disclosed herein, wherein milciclib and sorafenib are administered in separate pharmaceutical formulations, wherein each formulation further includes a pharmaceutically acceptable excipient. In one embodiment, one or both of the pharmaceutical formulations is in a controlled release form.

DD. Any of methods disclosed herein, wherein milciclib and sorafenib are administered to the patient sequentially.

EE. Any of methods disclosed herein, wherein, the administration of milciclib begins before administration of sorafenib to the patient.

FF. Any of methods disclosed herein, wherein the administration of milciclib begins after administration of sorafenib to the patient.

GG. Any of methods disclosed herein, wherein milciclib and sorafenib are each administered in separate pharmaceutical formulations that each further include a pharmaceutically acceptable excipient. In one embodiment, one or both pharmaceutical formulations are formulated for oral administration. For example, in one embodiment, each pharmaceutical formulation is independently in the form of a tablet, pill, or capsule.

HH. Milciclib, or a pharmaceutically acceptable salt, isomer, or tautomer thereof, for use in the treatment or prevention of cancer in a patient in need thereof, further comprising the use of another anticancer drug that is selected from the group consisting of sorafenib, lenvatinib, regorafenib, sunitinib, nivolumab, gemcitabine, and palbociclib.

II. Milciclib, or a pharmaceutically acceptable salt, isomer, or tautomer thereof, for use in the treatment or prevention of non-small cell lung cancer, renal cell carcinoma, hepatocellular carcinoma, thyroid carcinoma, colorectal cancer, gastrointestinal stromal tumors, breast cancer, prostate cancer, pancreatic cancer, or thymoma in a patient in need thereof, further comprising the use of another anticancer drug.

JJ. Milciclib, or a pharmaceutically acceptable salt, isomer, or tautomer thereof, for use in the treatment or prevention of non-small cell lung cancer, renal cell carcinoma, hepatocellular carcinoma, thyroid carcinoma, colorectal cancer, gastrointestinal stromal tumors, breast cancer, prostate cancer, pancreatic cancer, or thymoma in a patient in need thereof, further comprising the use of another anticancer drug that is selected from the group consisting of sorafenib, lenvatinib, regorafenib, sunitinib, nivolumab, gemcitabine, and palbociclib.

KK. Milciclib, or a pharmaceutically acceptable salt, isomer, or tautomer thereof, for use in the manufacture of a medicament for the treatment or prevention of cancer in a patient in need thereof, further comprising the use of another anticancer drug that is selected from the group consisting of sorafenib, lenvatinib, regorafenib, sunitinib, nivolumab, gemcitabine, and palbociclib.

LL. Milciclib, or a pharmaceutically acceptable salt, isomer, or tautomer thereof, for use in the manufacture of a medicament for the treatment or prevention of non-small cell lung cancer, renal cell carcinoma, hepatocellular carcinoma, thyroid carcinoma, colorectal cancer, gastrointestinal stromal tumors, breast cancer, prostate cancer, pancreatic cancer, or thymoma in a patient in need thereof, further comprising the use of another anticancer drug.

MM. Milciclib, or a pharmaceutically acceptable salt, isomer, or tautomer thereof, for use in the manufacture of a medicament for the treatment or prevention of non-small cell lung cancer, renal cell carcinoma, hepatocellular carcinoma, thyroid carcinoma, colorectal cancer, gastrointestinal stromal tumors, breast cancer, prostate cancer, pancreatic cancer, or thymoma in a patient in need thereof, further comprising the use of another anticancer drug that is selected from the group consisting of sorafenib, lenvatinib, regorafenib, sunitinib, nivolumab, gemcitabine, and palbociclib.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application, in particular the claims of this application.

It is to be understood that while the invention has been described in conjunction with the preferred specific embodiments thereof, that the foregoing description is intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains.

EXAMPLES

Example 1. IC50 Values by Cell Proliferation Assay

See Shailubhai, K et al. "Atiprimod is an inhibitor of cancer cell proliferation and angiogenesis." J Exp Ther Oncol. 2004; 4: 267-279; and Choudhari et al. "Deactivation of Akt and STAT3 signaling promotes apoptosis, inhibits proliferation, and enhances the sensitivity of hepatocellular carcinoma cells to an anticancer agent, atiprimod" Molecular Cancer Therapeutics. 2007; 6: 112-121. References are incorporated herein in their entireties.

MHCC97H and MHCC97L (highly metastatic hepatocellular carcinoma cell line, derived from humans)

HepG2.2.15 cells are derived from the human hepatoblastoma cell line HepG2.

Cells (MHCC97H, MHCC97L, and HepG2.2.15) were cultured for 24 hours in 2% FBS and then were trypsinized, resuspended in 2% FBS and seeded in a rat collagen coated 96-well plate at a density of 10,000 cells/100 µl/well, a day before the experiment and cultured at 37° C. in 5% $CO_2$. The cells were treated the next day with milciclib, sorafenib, regorafenib, sunitinib, and lenvatinib, individually or in combination in DMEM/F12+2% FBS+for 72 hours prior to the addition of WST-1 reagent. About 100 µL media was added to control well. After cells had been cultured for 72 hours with different drug concentrations, cells were washed 3 times with sterile 1× Phosphate buffered saline (PBS). To determine cell proliferation by the colorimetric test, 10 µL of WST-1 reagent (Sigma Aldrich, St Louis, Mo.) was added in 100 µL cell culture media and incubated for 2 hours in 5% $CO_2$ at 37° C. At the end of incubation period, the plate was placed on a plate shaker for 1 minute and was monitored using a spectrophotometer at an optical density of 450 nm with a reference wavelength of 600 nm using Tecan F200 and iControl software. $IC_{50}$ values were determined using GraphPad Prism (GraphPad Software, La Jolla, Calif.). Each experiment was performed in duplicate and repeated 2 times.

Figure 4:
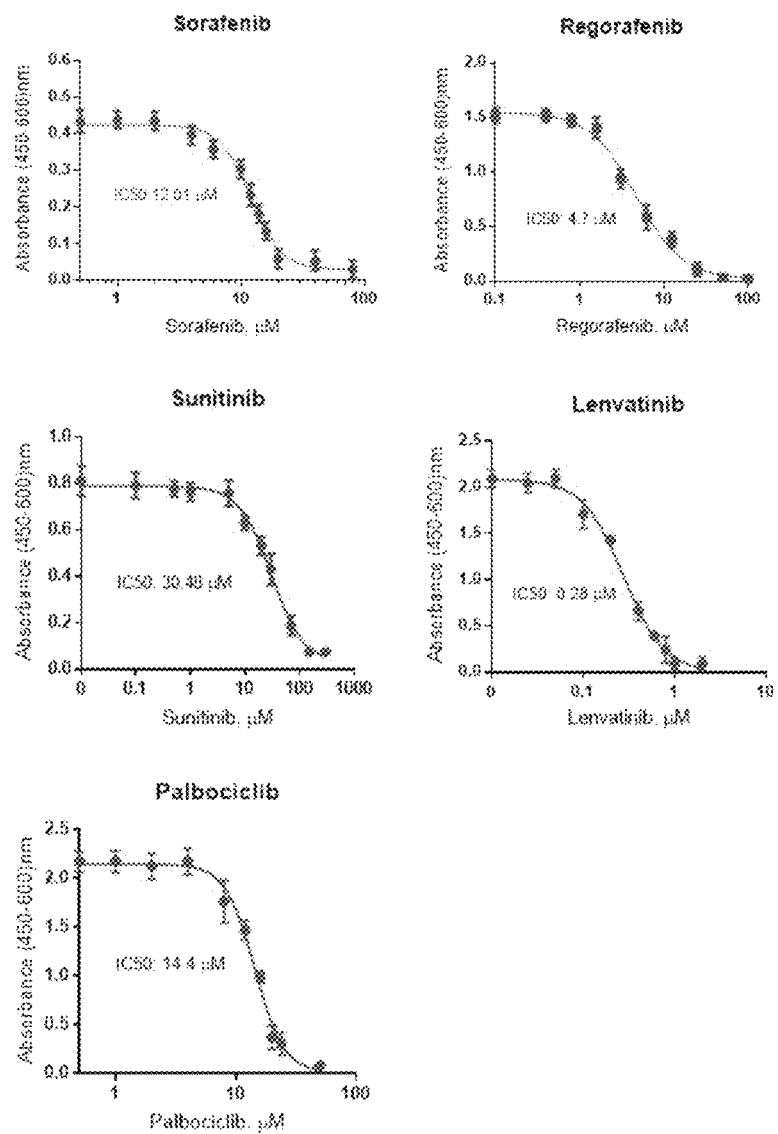
FIG. 4 is a series of graphs depicting the IC50 of sorafenib, regorafenib, sunitinib, lenvatinib, and palbociclib in a MHCC97H cell proliferation assay.
Figure 5:
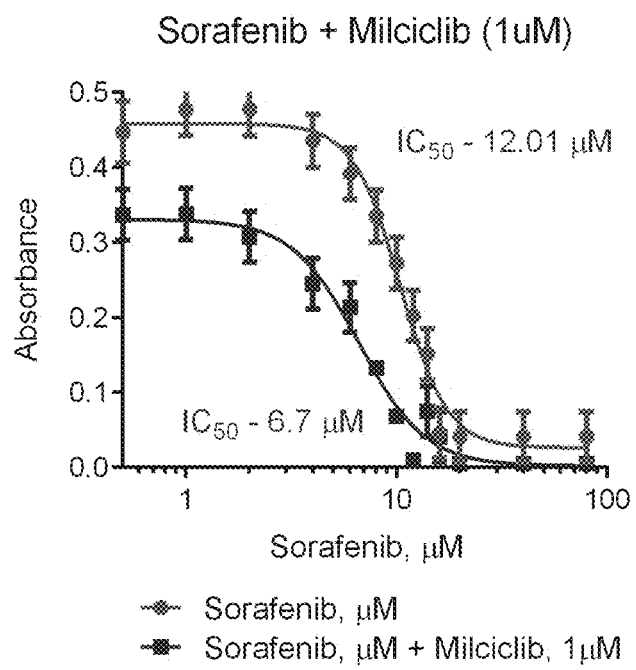
FIG. 5 is a set of two graphs showing the IC50 value of sorafenib and the combination of sorafenib and milciclib in MHCC97H cells.
Figure 6:
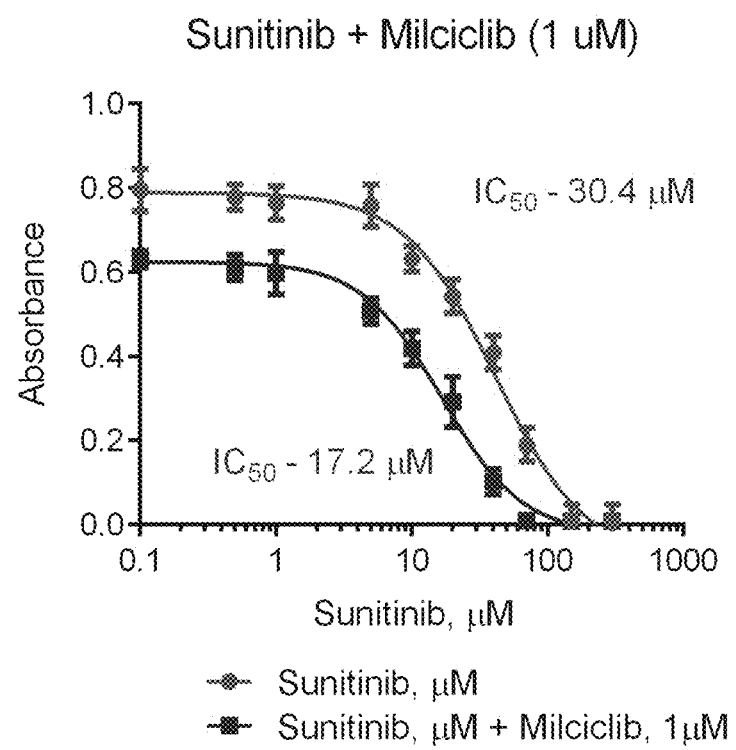
FIG. 6 is a set of two graphs showing the IC50 value of sunitinib and the combination of sunitinib and milciclib in MHCC97H cells.
Figure 7:
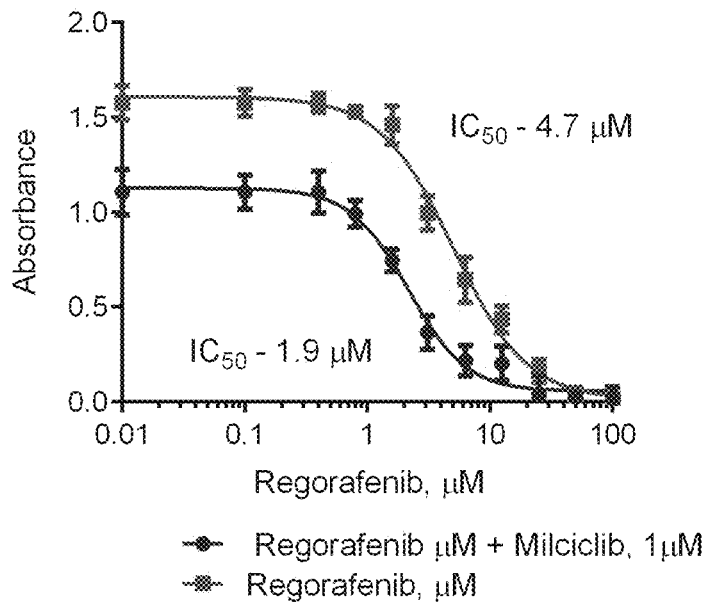
FIG. 7 is a set of two graphs showing the IC50 value of regorafenib and the combination of regorafenib and milciclib in MHCC97H cells.
Figure 8:
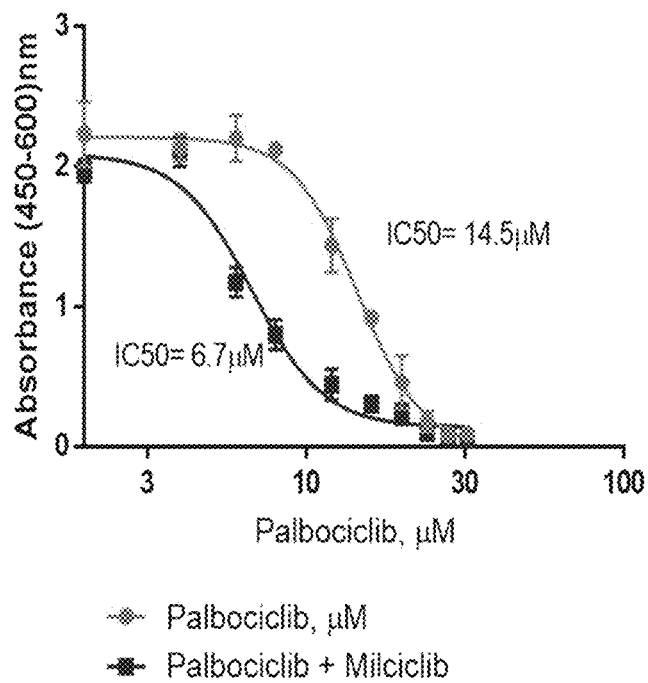
FIG. 8 is a set of two graphs showing the IC50 value of palbociclib and the combination of palbociclib and milciclib in MHCC97H cells.
Figure 9:
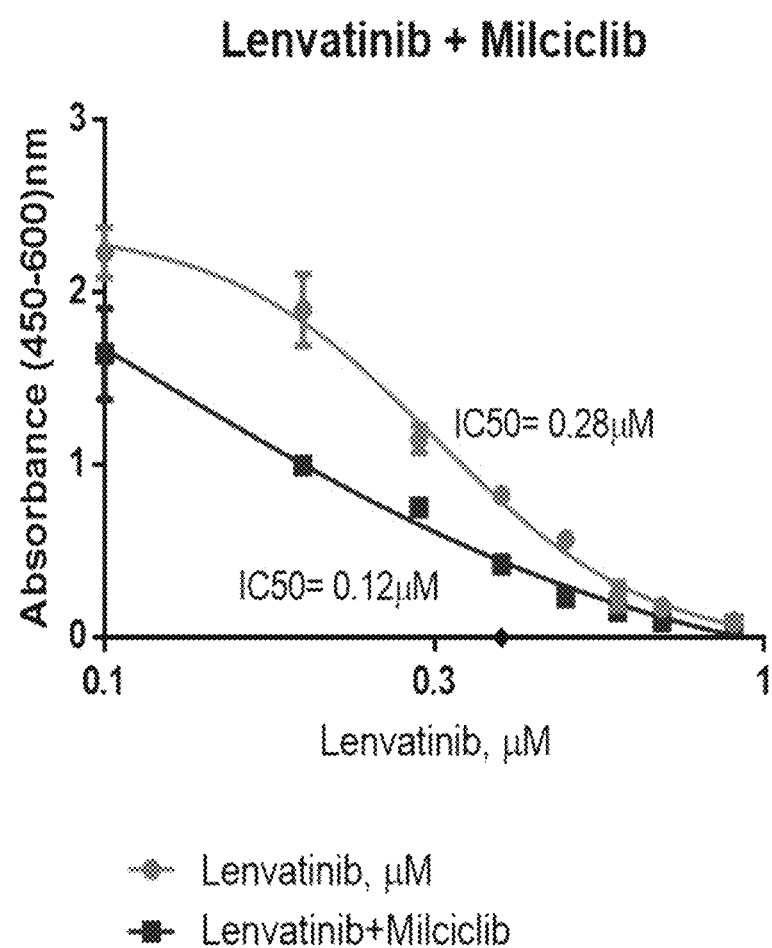
FIG. 9 is a set of two graphs showing the IC50 value of lenvatinib and the combination of lenvatinib and milciclib in MHCC97H cells.
Figure 10:
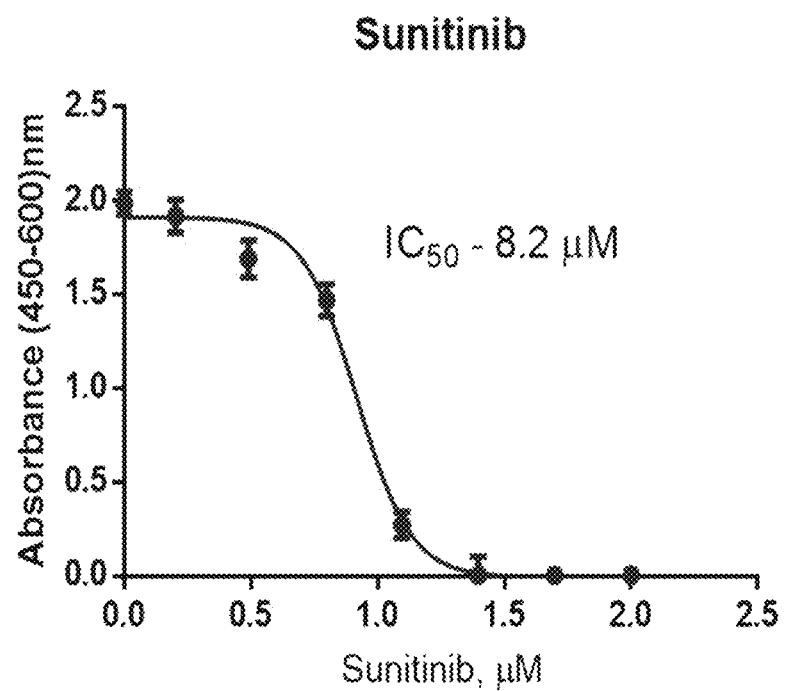
FIG. 10 is a graph showing the IC50 value of sunitinib in MHCC97L cells.
Figure 11:
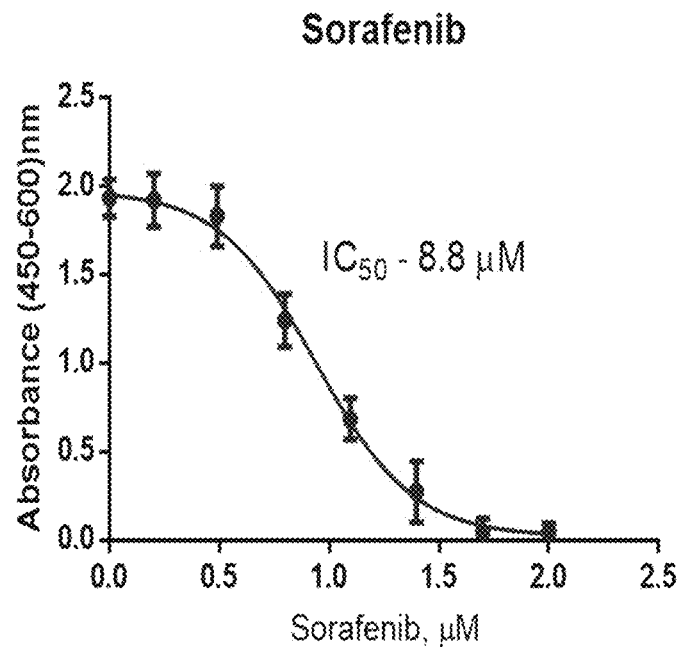
FIG. 11 is a graph showing the IC50 value of sorafenib in MHCC97L cells.
Figure 12:
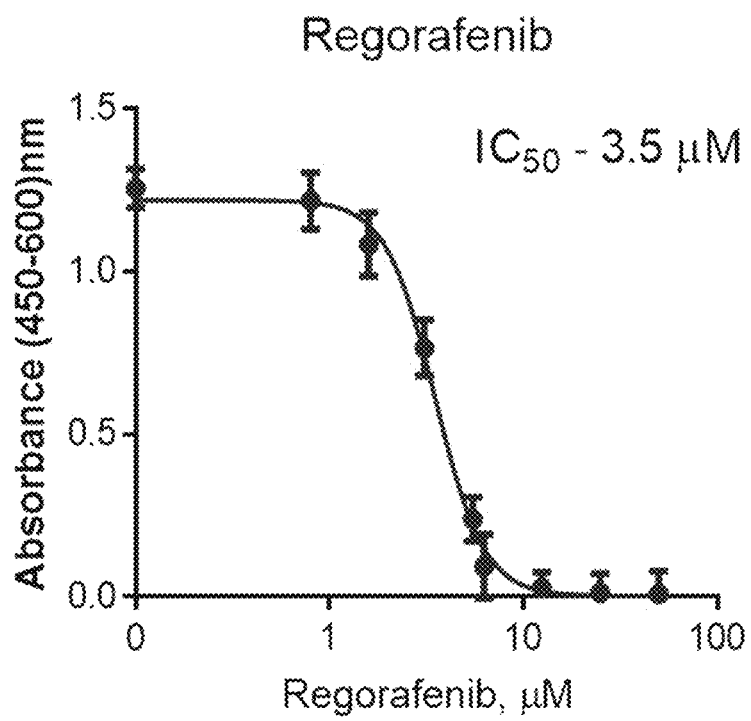
FIG. 12 is a graph showing the IC50 value of regorafenib in MHCC97L cells.
Figure 13:
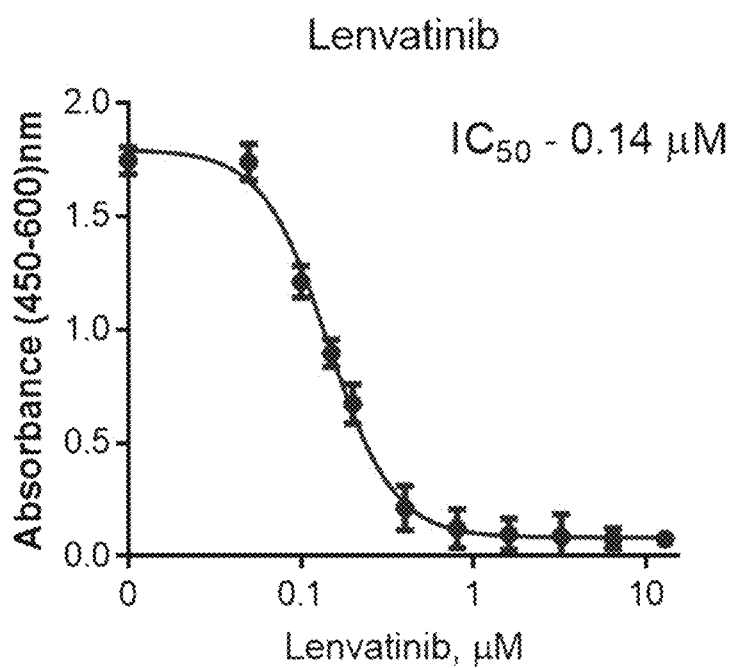
FIG. 13 is a graph showing the IC50 value of lenvatinib in MHCC97L cells.
Figure 14:
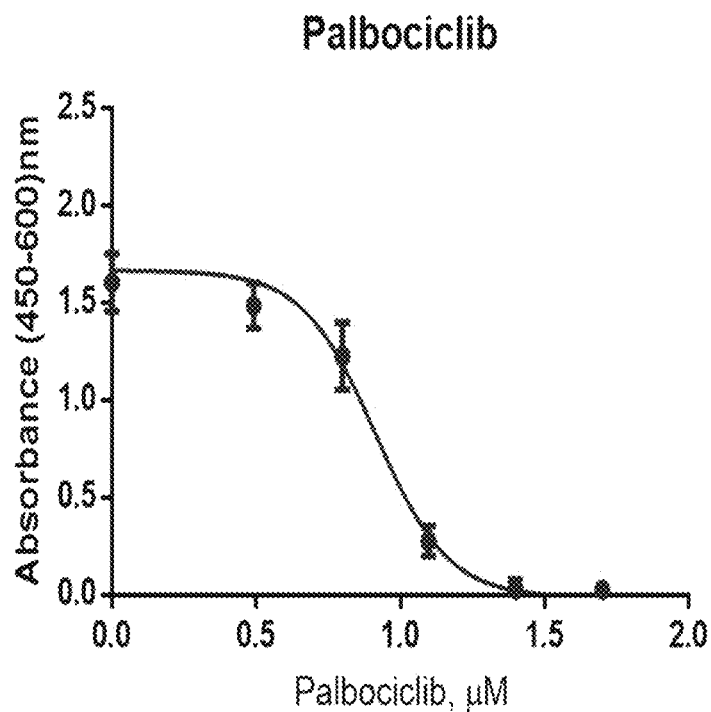
FIG. 14 is a graph showing the IC50 value of palbociclib in MHCC97L cells.
Figure 15:
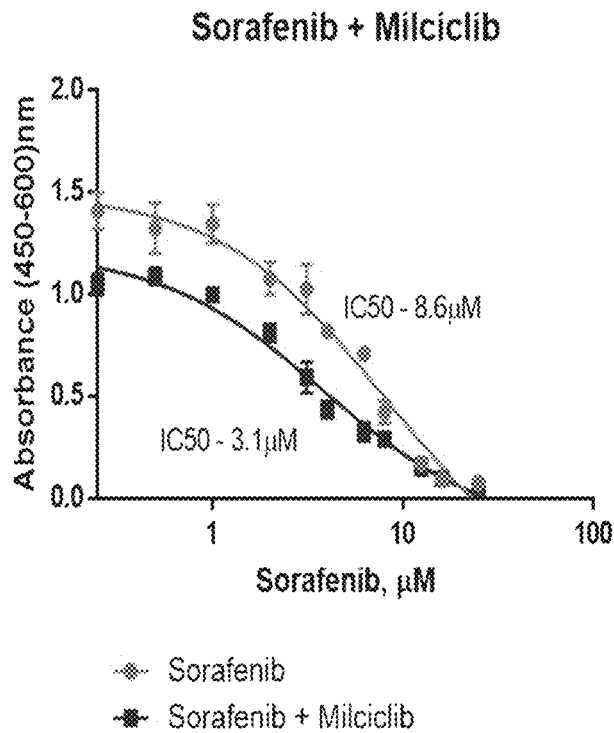
FIG. 15 is a set of two graphs showing the IC50 value of sorafenib and the combination of sorafenib and milciclib in MHCC97L cells.
Figure 16:
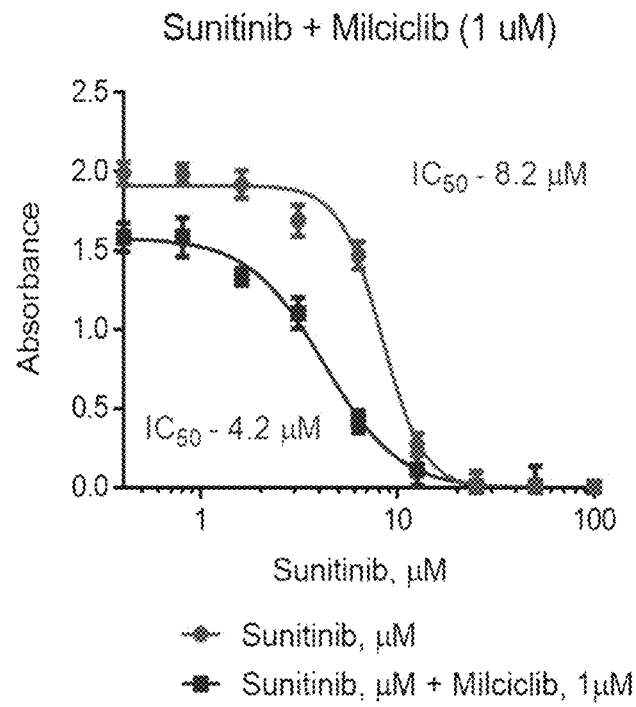
FIG. 16 is a set of two graphs showing the IC50 value of sunitinib and the combination of sunitinib and milciclib in MHCC97L cells.
Figure 17:
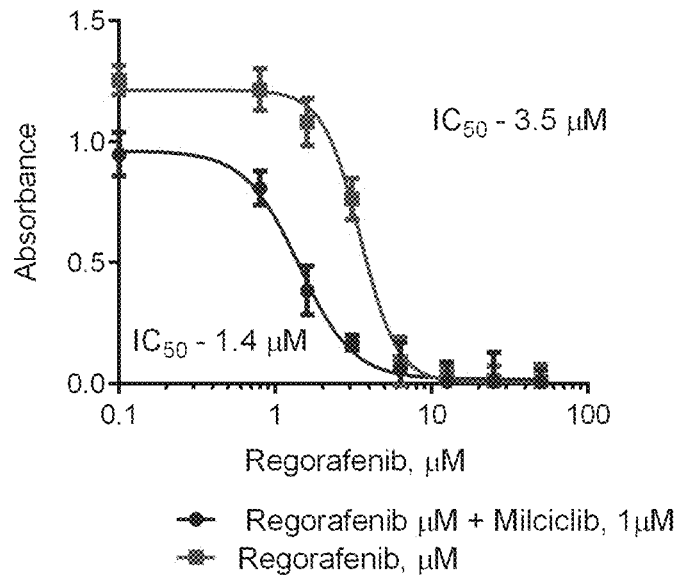
FIG. 17 is a set of two graphs showing the IC50 value of regorafenib and the combination of regorafenib and milciclib in MHCC97L cells.
Figure 18:
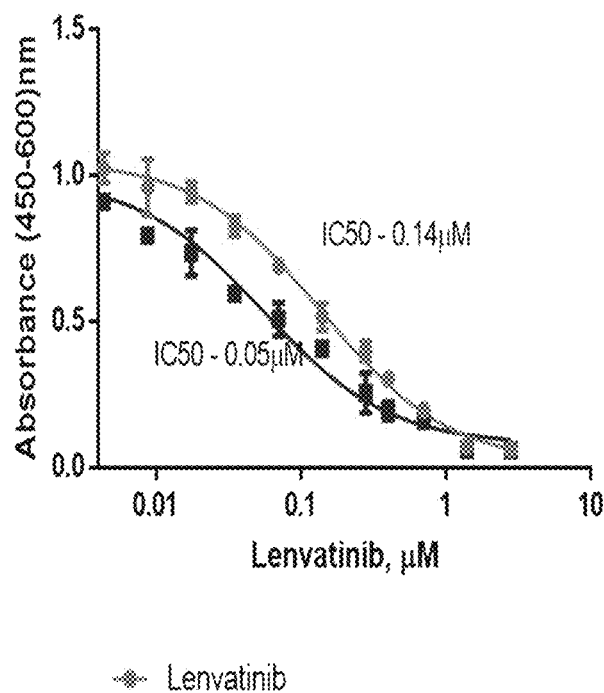
FIG. 18 is a set of two graphs showing the IC50 value of lenvatinib and the combination of lenvatinib and milciclib in MHCC97L cells.
Figure 19:
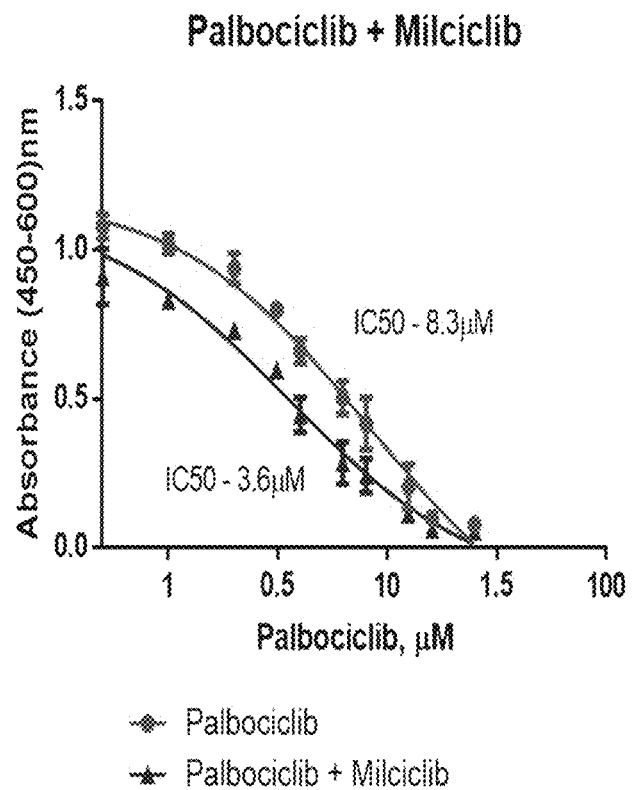
FIG. 19 is a set of two graphs showing the IC50 value of palbociclib and the combination of palbociclib and milciclib in MHCC97L cells.
Figure 20:
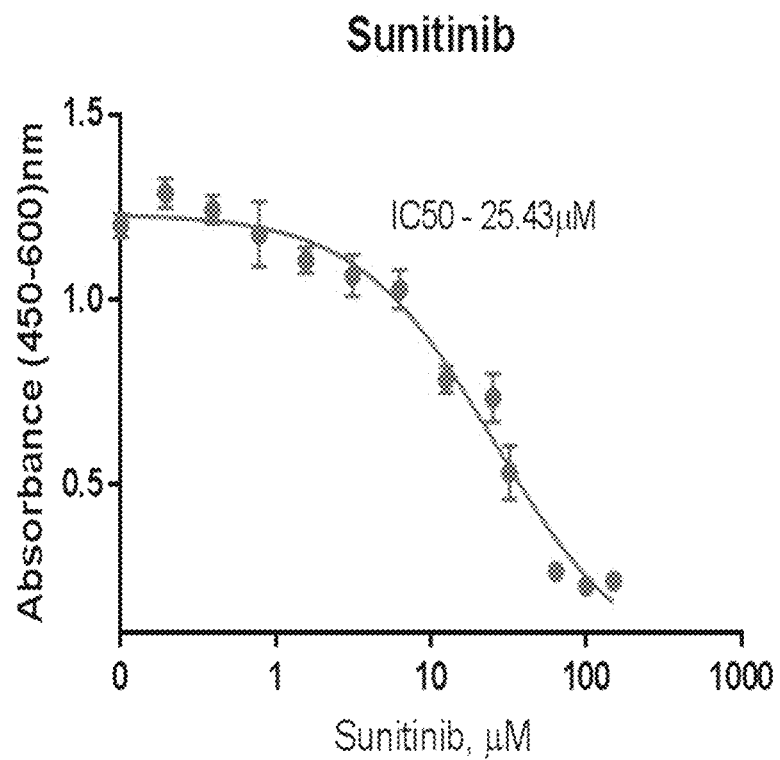
FIG. 20 is a graph showing the IC50 value of sunitinib in HepG2.2.15 cells.
Figure 21:
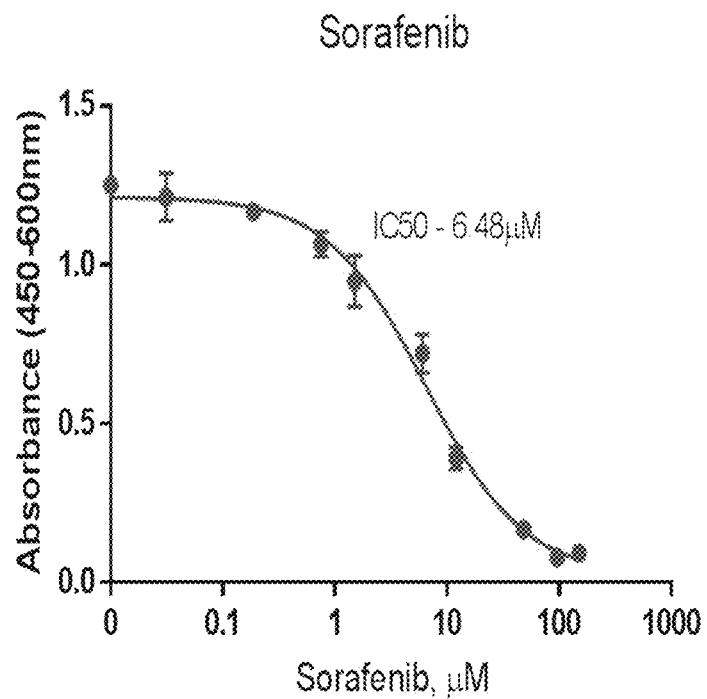
FIG. 21 is a graph showing the IC50 value of sorafenib in HepG2.2.15 cells.
Figure 22:
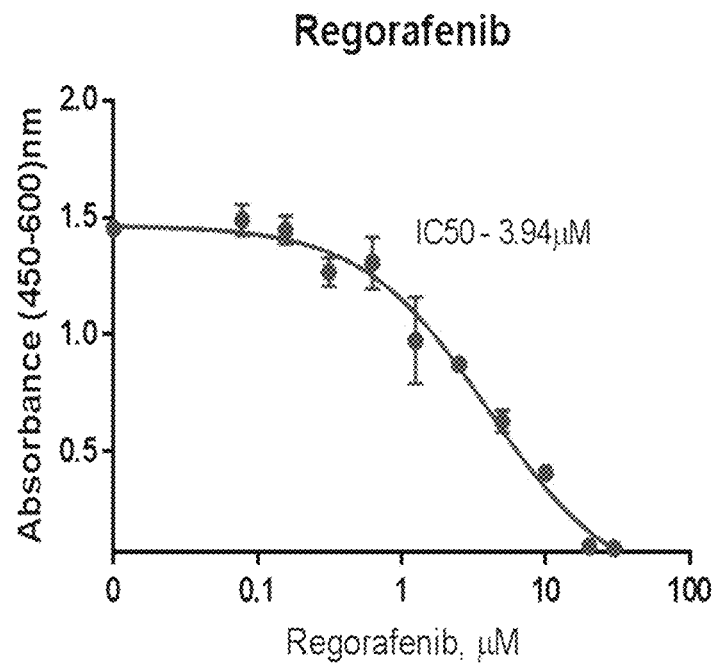
FIG. 22 is a graph showing the IC50 value of regorafenib in HepG2.2.15 cells.
Figure 23:
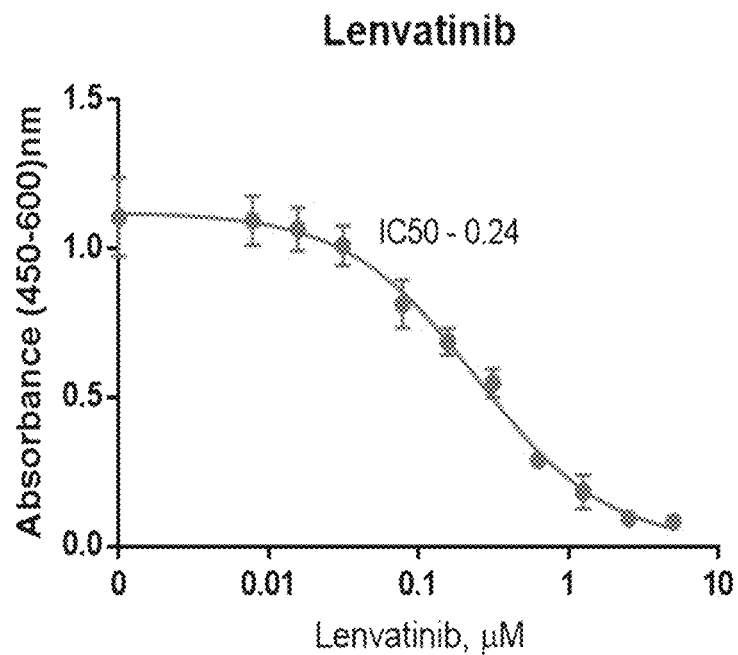
FIG. 23 is a graph showing the IC50 value of lenvatinib in HepG2.2.15 cells.
Figure 24:
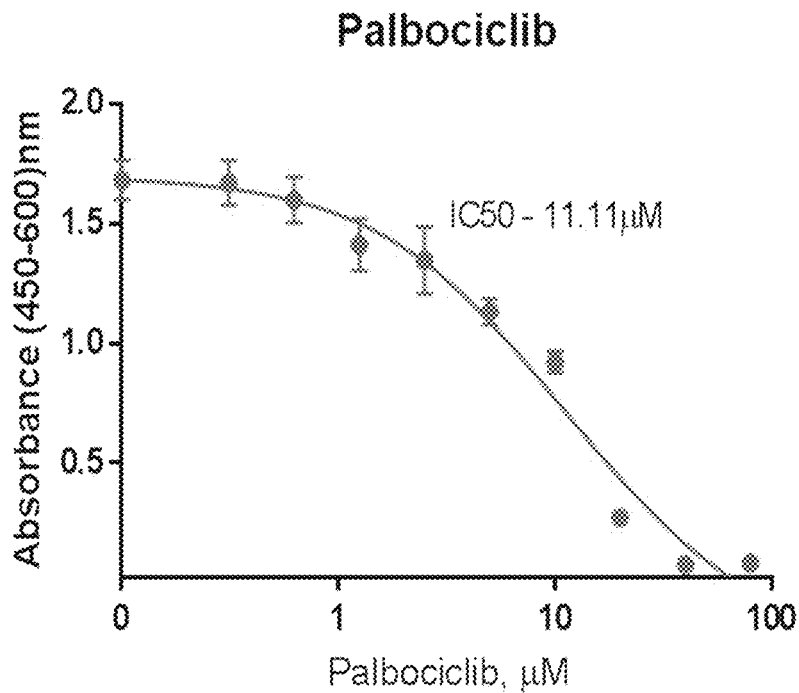
FIG. 24 is a graph showing the IC50 value of palbociclib in HepG2.2.15 cells.
Figure 25:
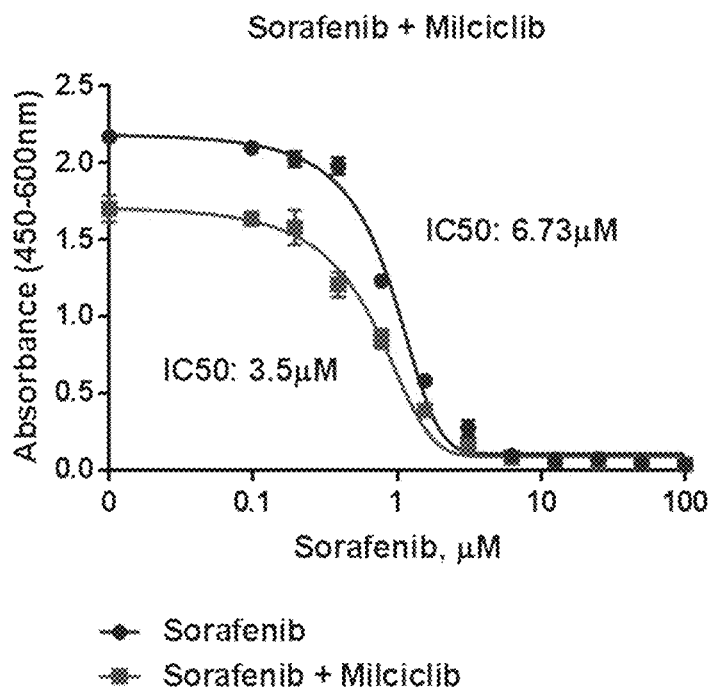
FIG. 25 is a set of two graphs showing the IC50 value of sorafenib and the combination of sorafenib and milciclib in HepG2.2.15 cells.
Figure 26:
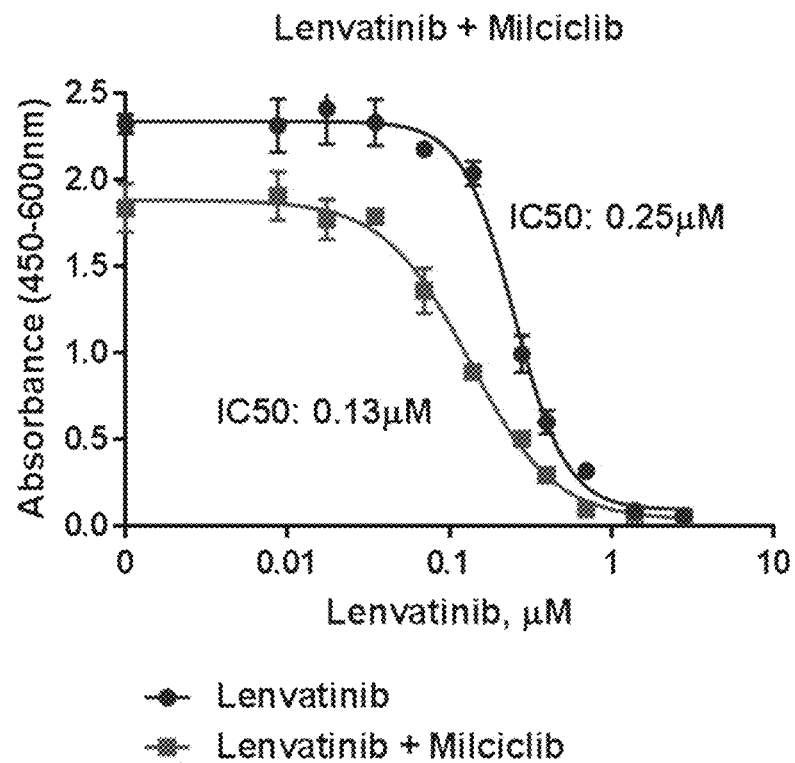
FIG. 26 is a set of two graphs showing the IC50 value of lenvatinib and the combination of lenvatinib and milciclib in HepG2.2.15 cells.
Figure 27:
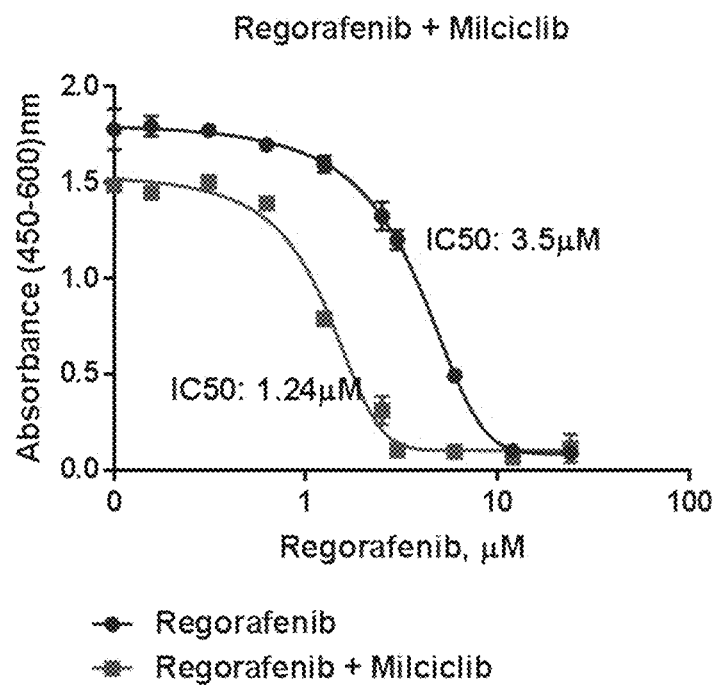
FIG. 27 is a set of two graphs showing the IC50 value of regorafenib and the combination of regorafenib and milciclib in HepG2.2.15 cells.
Figure 28:
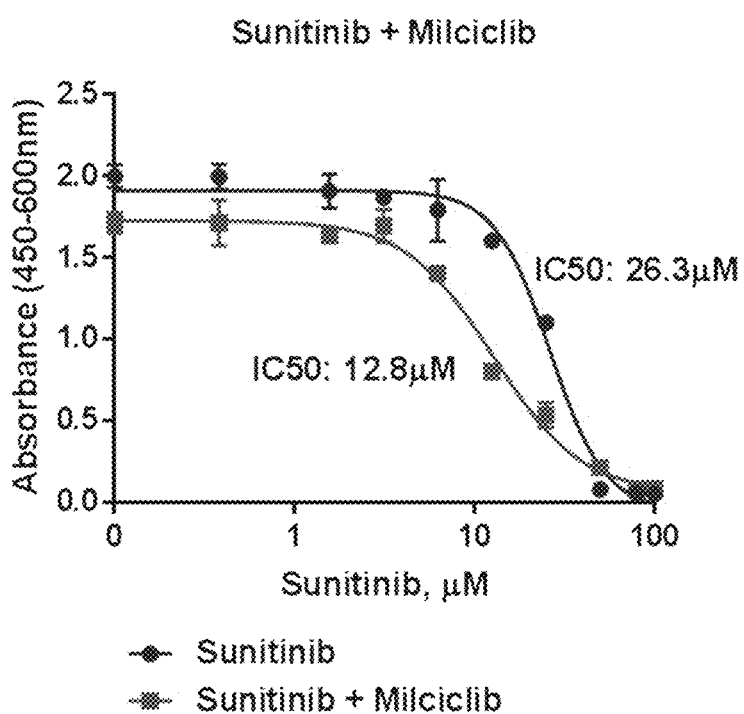
FIG. 28 is a set of two graphs showing the IC50 value of sunitinib and the combination of sunitinib and milciclib in HepG2.2.15 cells.

Each inhibitor exhibited a dose dependent decrease in cell proliferation with comparable half maximal inhibitory concentration (IC50) across the three cell lines: FIGS. 1 and 4—MHCC97H cells; FIGS. 2 and 10-14—MHCC97L cells; and FIGS. 3 and 20-24—HepG2.2.15 cells.

Lenvatinib exhibited the lowest $IC_{50}$ value followed by milciclib, regorafenib, sorafenib and sunitinib.

| PROTEIN KINASE INHIBITORS | CELL LINE | | |
|---|---|---|---|
| | MHCC97H $IC_{50}$, µM | MHCC97L $IC_{50}$, µM | HepG2.2.15 $IC_{50}$, µM |
| MILCICLIB | 1.3 | 1 | 1.16 |
| SORAFENIB | 12.01 | 8.8 | 6.48 |
| REGORAFENIB | 4.7 | 3.5 | 3.94 |
| LENVATINIB | 0.28 | 0.14 | 0.24 |
| SUNITINIB | 30.48 | 8.2 | 25.43 |
| PALBOCICLIB | 14.5 | 8.2 | 11.11 |

Example 2. IC50 Values of Inhibitors in Combination with Milciclib by Cell Proliferation Assay in MHCC97H Cells Synergy Studies

| PROTEIN KINASE INHIBITORS | $IC_{50}$ (µM) OF KINASE INHIBITORS | $IC_{50}$ (µM) KINASE INHIBITORS + 1.3 µM MILCICLIB |
|---|---|---|
| SORAFENIB | 12.01 | 6.7 |
| REGORAFENIB | 4.7 | 1.9 |
| LENVATINIB | 0.28 | 0.12 |

| PROTEIN KINASE INHIBITORS | IC$_{50}$ (μM) OF KINASE INHIBITORS | IC$_{50}$ (μM) KINASE INHIBITORS + 1.3 μM MILCICLIB |
|---|---|---|
| SUNITINIB | 30.4 | 17.2 |
| PALBOCICLIB | 14.5 | 6.7 |

A synergistic effect on inhibition of cell proliferation was observed upon treating MHCC97H, MHCC97L, and HepG2.2.15 cells with increasing concentration of TKIs in the presence of fixed concentration corresponding to milciclib IC$_{50}$ value. In all cases, the IC$_{50}$ value of each TKI was reduced by ~50% (MHCC97H: FIGS. 5-9; MHCC97L: FIGS. 15-19; HepG2.2.15: FIGS. 25-28).

Increasing concentration of inhibitors with a fixed concentration of milciclib was tested on MHCC97L and MHCC97H cells to determine the synergistic effect on inhibition of cell proliferation.

In the synergy studies the arrow represents the mid-point of combination of TKIs with milciclib. For sorafenib, the individual IC$_{50}$ was 12 μM but with the combination with milciclib the IC$_{50}$ was 6.7 μM in MHCC97H (FIG. 29A).

For lenvatinib, the individual IC$_{50}$ was 0.28 μM but with the combination with milciclib the IC$_{50}$ was 0.12 μM in MHCC97H (FIG. 29B).

For regorafenib, the individual IC$_{50}$ was 4.7 μM but with the combination with milciclib the IC$_{50}$ was 1.9 μM in MHCC97H (FIG. 29C).

Example 3. MHCC97H Cells Produce Human Alphafetoprotein (AFP)

AFP ELISA Assay

MHCC97H cells were seeded at a density of 500,000 cells/2 mL/well on a 6 well culture plate and incubated overnight at 37° C. in a humidified $CO_2$ incubator. Cells were then treated with 1.3 μM milciclib or vehicle in DMEM/F12+2% FBS for 72 hours. Subsequently, cells were lysed in RIPA buffer, the supernatant was collected and used to perform ELISA assay as per the manufacturer's instructions. In orthotopic HCC mouse model, levels of serum marker alpha-fetoprotein (AFP) were determined on day 0, 6, 12, 18, 24, 30, 36, 42 and 48 using High Range AFP kit as per manufacturer's instructions.

Freshly cultured MHCC97H cells were treated with 1.3 μM milciclib for 72 hours to determine the AFP levels. Appreciably lower levels of AFP were detected in milciclib treated cells as compared to vehicle control (FIG. 30).

Example 4. Promega ApoTox-Glo™ Triplex Assay

The HCC cells were seeded at a density of 10,000 cells/100 μL in each well of a rat collagen coated 96 well plate and allowed to grow overnight in 5% $CO_2$ at 37° C. The cells were then treated with different concentrations of each agent alone or in combination with 1.3 μM milciclib in MHCC97H and 1.16 μM milciclib in MHCC97L cells for 48 hours. Promega ApoTox-Glo Triplex assay (Madison, Wis.) was used according to manufacturer's instructions to determine the number of viable cells, cell death because of apoptosis and cytotoxic effect on cells. After 48 hours the viability/cytotoxicity reagent, containing both the GF-AFC substrate and the bis-AAF-R110 substrate, was added to all wells and incubated for 30 minutes and was measured at an optical density of 400EX/505EM for viability and 485EX/520EM for cytotoxicity. For apoptosis, caspase-glo 3/7 was added to all wells, mixed briefly at 500 rpm for 30 seconds, then incubated at room temperature for 30 minutes and luminescence was measured which is proportional to the amount of caspase activity present. See Ito H, Uchida T, Makita K. Ketamine causes mitochondrial dysfunction in human induced pluripotent stem cell-derived neurons. PLoS One. 2015; 10: e0128445) for experimental details. Reference is incorporated herein in its entirety.

Milciclib in combination with other TKIs at various concentrations decreased the cell viability and increased caspase 3/7 activity in MHCC97H cells (FIGS. 31-39) and MHCC97L cells (FIGS. 40-50) in a dose-dependent manner compared to those in vehicle-treated cells.

Example 5. Wound Healing (Using 0.5×10$^6$ Cells)

Cells were seeded at a density of 500,000 cells/2 mL/well on to a collagen-coated 6-well culture plate and incubated overnight in a humidified $CO_2$ incubator at 37° C. to form a uniform monolayer. The monolayer was then scratched in a straight line with a new 10 μL pipette tip across the center of the well. After scratching, cells were washed with sterile PBS once to remove detached cells. Subsequently, wells were replenished with fresh DMEM/F12 containing 2% FBS and the test article either alone or in combination with milciclib. Photos were taken of the scratched monolayer immediately T$_0$ and after various times 24, 48, and 72 hours using an Olympus IX81 microscope. Images were analyzed using SlideBook™ 5 software. The values were expressed as a percentage of migration. See Saxena N K, Sharma D, Ding X, et al. Concomitant activation of the JAK/STAT, PI3K/AKT, and ERK signaling is involved in leptin-mediated promotion of invasion and migration of hepatocellular carcinoma cells. Cancer Res. 2007; 67: 2497-2507.

Treatment of scratched monolayer of MHCC97H cells with TKIs (tyrosine kinase inhibitors) in combination with milciclib (1.3 μM) for 96 h, reduced cell migration as compared to corresponding vehicle control (FIGS. 51-55).

Treatment of scratched monolayer of MHCC97L cells with milciclib alone or in combination with other TKIs for 96 hours, reduced cell migration as compared to corresponding vehicle control (FIGS. 56-60).

Treatment of scratched monolayer of HepG2.2.15 cells with milciclib alone or in combination with other TKIs for 96 hours, reduced cell migration as compared to corresponding vehicle control (FIGS. 61-63).

Example 6. EMT Assays

EMT (Epithelial to Mesenchymal Transition) induction employing kit from R&D systems (Cat # CCM017)

For transwell invasion assay HCC cells were seeded in the top chamber in 6 well transwell plates (Sigma-Aldrich, St. Louis, Mo.) at a density of 100,000 cells/500 μL/well in standard culture media containing 100× StemXVivo® EMT Inducing Media Supplement (R&D systems, Minneapolis, Minn.) and was incubated overnight at 37° C. in humidified $CO_2$ incubator. Next day, EMT inducing media with or without the test articles was added and incubation was continued for 10 days with media changes every 3 days. On the 10th day, the number of cells migrated to the lower chamber was determined using Bio-Rad (Hercules, Calif.) automatic cell counter. Values obtained were expressed as a percentage of invasion and the cell counts of control cells were considered 100%.

The invasive potential of cancer cells is dependent on losing epithelial characteristics and acquiring a migratory mesenchymal property referred to as Epithelial to Mesenchymal Transition (EMT).

The inclusion of milciclib or TKIs alone resulted in statistically significant inhibition (P<0.05) in cell migration in MHCC97L cells. Regorafenib, sorafenib, sunitinib and lenvatinib in combination with milciclib reduced the invasion potential to a greater extent as compared to individual treatment (P<0.005) (FIG. 64).

The inclusion of milciclib or TKIs alone resulted in statistically significant inhibition (P<0.05) in cell migration in MHCC97H cells. Regorafenib, sorafenib, sunitinib and lenvatinib in combination with milciclib reduced the invasion potential to a greater extent as compared to individual treatment (P<0.005), demonstrative of the anti-invasive potential of milciclib (FIG. 65).

Example 7. Orthotopic Tumor Induction in Athymic Nude Mice

Figure 66:
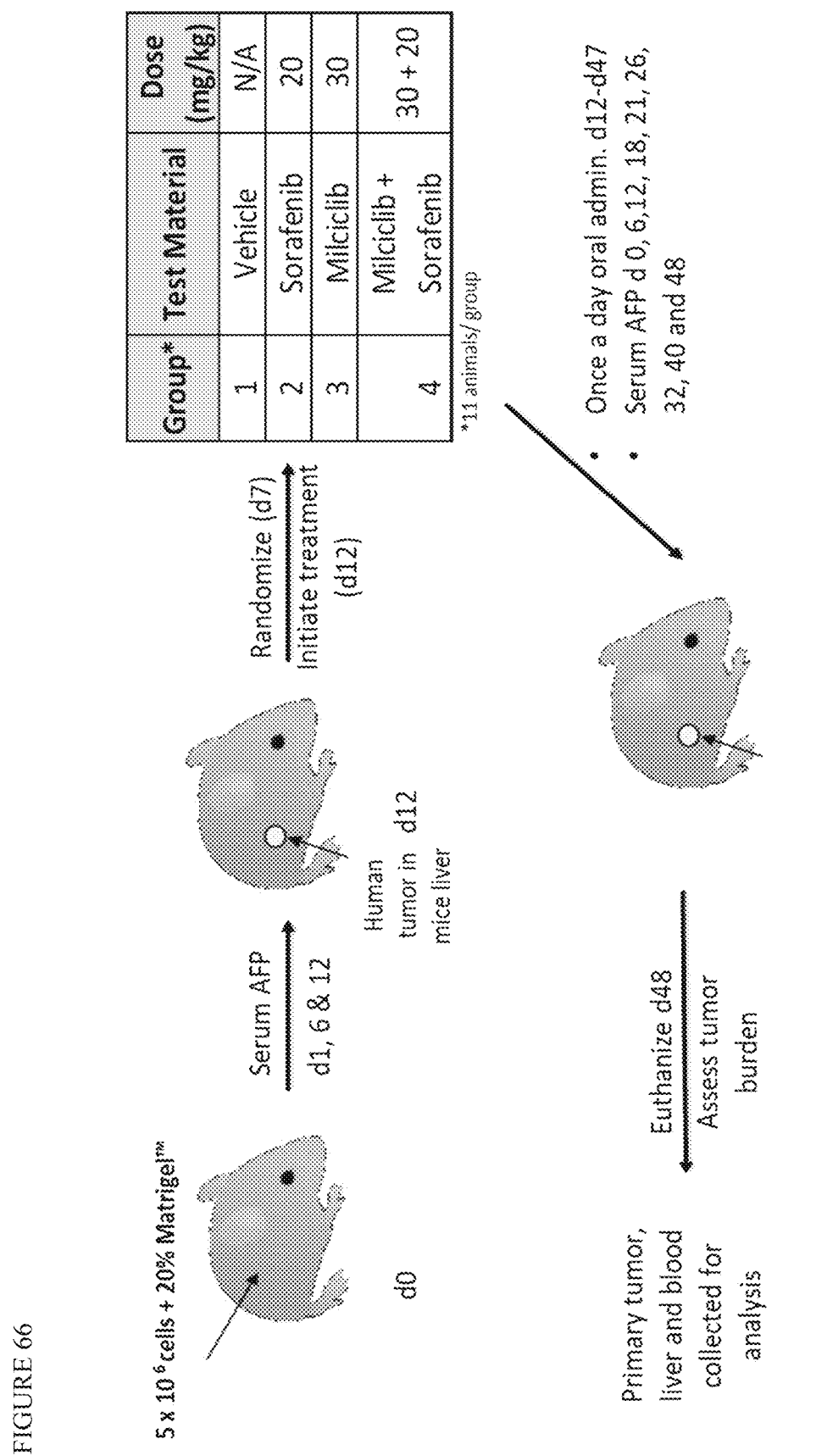
FIG. 66 is a schematic depicting the experimental design of in vivo studies wherein athymic mice with livers injected with MHCC97H cells were treated with vehicle, sorafenib, milciclib, or milciclib+sorafenib.

Mouse experiments were performed in accordance with the guidelines approved by the Institutional Animal Care and use committee of Washington Biotechnology Inc (Baltimore, Md.) where the studies were conducted. (FIG. 66) Test agents were dissolved in chremophor/ethanol (1:1) to make a 5× stock solution and diluted in water when used. MHCC97H human liver cells (5×106) in PBS were mixed with 20% Matrigel and then inoculated orthotopically into the right flank of female Balb/c nude mice. Seven days after cell inoculation, the mice were randomly allocated to either the treatment group (n=12) or the control group (n=12) based on the levels of AFP. The daily animal inspection was conducted for general appearance and tumor growth. Milciclib (30 mg/Kg), sorafenib (20 mg/Kg), milciclib+sorafenib or the corresponding vehicle was given orally to individual mice once daily from day 12 until day 47. After completion of the treatment at day 48, animals were euthanized and blood, liver tissues and tumor were collected for gene expression and mechanistic assays. Liver tumors developed 100% of animals challenged with orthotopic MHCC97H injection.

Oral administration of milciclib (30 mg/kg/day) either alone or in combination with sorafenib (20 mg/kg/day) produced synergistic effect in reducing tumor growth [milciclib—20% (p<0.002) or sorafenib—21% (p<0.001) vs combination—38% (p<0.0002) as compared to vehicle (FIG. 67). Vehicle group had more liver weight but with combination the liver weight goes down (FIG. 68).

Pictures showing the difference in tumor burden with the treatment of milciclib, sorafenib, and the combination are provided. Vehicle group has an enlarged tumor but with the combination, the tumor burden goes down (FIG. 69).

A steady increase in serum AFP was observed in vehicle administered animals until the end of the study. Significantly lower serum AFP levels were recorded for animals treated with milciclib (30 mg/kg), sorafenib (20 mg/kg) alone or in combination (FIG. 70).

Example 8. Milciclib Acts Via Specifically Downregulating miR221/222 miRNA Isolation and Expression Analysis miRNA from athymic nude mice following treatment with vehicle, milciclib, sorafenib, or milciclib+sorafenib was isolated from Total RNA using the TaqMan Advanced miRNA cDNA Synthesis Kit (Thermo Fisher Scientific, Rockford, Ill.) according to the manufacturer's instructions. miRNA-221 and miR-222 quantifications were performed in duplicates using TaqMan Advanced miRNA Assay (Thermo Fisher Scientific, Rockford, Ill.) with a sample dilution of 1:10. The PCR mixture was incubated at 95° C. for 20 seconds, followed by 40 cycles of 95° C. for 3 seconds and 60° C. for 30 seconds. Results were normalized to hsa-miR-192-5p as reference miRNA and the relative gene expression calculated as 2−ΔCT was expressed as fold increase over control samples.

Gene expression studies suggest that milciclib possibly exerts its action through downregulation of miR-221 and miR-222.

Data suggest that oral treatment with milciclib exerts its activity via downregulation of miR-221 and miR-222 (FIGS. 71A and 71B).

Tumor tissues from mice treated with vehicle, sorafenib, milciclib, milciclib+sorafenib and normal liver tissues from naïve untreated mice were collected and levels of miR-221 and miR-222 were determined. The levels of both of miR-221 and miR-222 were elevated in tumors from vehicle treated mice. Treatment with sorafenib alone modestly reduced the expression of these miRs but treatment with milciclib alone significantly reduced expression of both miR-221 and miR-222. These data suggest that milciclib specifically acts via reducing expression of miR-221 and miR-222, which are known to be major culprits of hepatocarcinogenesis (See Park J K, et al. "miR-221 silencing blocks hepatocellular carcinoma and promotes survival." Cancer Res. 2011; 71:7608-76.) These data also imply that oral treatment with milciclib reduced tumor growth via a mechanism distinct from orally administered sorafenib.

Example 9. Milciclib Mechanism of Action Studies

Western Blot Analysis

The tumor tissues from a thymic nude mice were weighed and homogenized with RIPA lysis buffer (Sigma-Aldrich, St. Louis, Mo.) and protease inhibitor cocktail (Sigma-Aldrich, St. Louis, Mo.). Tumor lysates were cleared by centrifugation and the protein concentration was determined using Bradford reagent (Sigma-Aldrich, St. Louis, Mo.). Equal amounts of protein (30 μg) were resolved on precast polyacrylamide gels (Thermo Fisher Scientific, Rockford, Ill.) and transferred to nitrocellulose membrane, 0.2 μm pore size (Thermo Fisher Scientific, Rockford, Ill.). The blots were blocked with 5% (w/v) nonfat dry milk for 2 h at room temperature and then probed with primary antibody overnight at 4° C. The primary antibodies were directed against the following proteins: human PTEN, human AKT and phospho-AKT (Ser473), human c-Myc, human CyclinD1 and human β-actin (Cell Signaling Technology, Beverly, Mass.). After three washes, incubation was followed by the reaction with horseradish peroxidase-conjugated secondary antibody for 1 h at room temperature. The immunoreactive bands were visualized using Image Studio 4.0-Western Analysis Ribbon (Li-Cor, Lincoln, Nebr.).

Reverse Transcription and Quantitative Real-Time PCR

Total RNA was extracted using the RNeasy Mini kit according to the manufacturer's instructions (Qiagen, Germantown, Md.). RNA was quantified using Nanodrop Lite (Thermo Scientific, Wilmington, Del.). Complementary DNA (cDNA) synthesis was performed by reverse transcription of total RNA using the High Capacity cDNA Reverse Transcription Kit (Thermo Fisher Scientific, Rockford, Ill.). Real-time quantitative PCR was employed using the Light-Cycler 480 Instrument II (Roche Diagnostics Corporation, Indianapolis, Ind.) using TaqMan Fast Advanced Master Mix and TaqMan Gene Expression probes for human p27, cyclin E2, cyclin A2, CdC6, MKI67, cyclin D1, p21, p57, c-Myc and p53 (Thermo Fisher Scientific). The expression of target genes was normalized to the housekeeping gene GAPDH in each sample. All samples were run in duplicate and the relative gene expression calculated as 2–ΔCT was expressed as fold increase over control samples.

The mechanism of action of milciclib appears to be distinct from the mechanism of action of sorafenib as it upregulated the expression of tumor suppressors such as p27, p21, p53 and p57 (FIGS. 72A, B, C, D).

Oral administration of milciclib alone or in combination with sorafenib downregulated expression of cyclins such as cyclin E2 and cyclin D1 (FIGS. 73A and 73B).

Oral administration of milciclib alone or in combination with sorafenib downregulated expression of cell proliferation genes such as MKI67, cdc6, c-Myc (FIGS. 74A, 74B, 74C).

The mechanism of action of milciclib appears to be distinct from the mechanism of action of sorafenib.

Mechanistic studies revealed a reduction in pAKT, c-Myc and cyclin D1 expression and upregulation of PTEN in liver samples derived from milciclib and milciclib and sorafenib administered animals as compared to vehicle treated group (FIG. 75).

Data from cell culture studies and from orthotopic HCC model in nude mice suggest that oral treatment with milciclib exerts its activity via a new mechanism.

Example 10. AFP ELISA Assay

MHCC97H cells were seeded at a density of 500,000 cells/2 mL/well on a 6 well culture plate and incubated overnight at 37° C. in a humidified $CO_2$ incubator. Cells were then treated with 1.3 μM milciclib or vehicle in DMEM/F12+2% FBS for 72 hours. Subsequently, cells were lysed in RIPA buffer, the supernatant was collected and used to perform ELISA assay as per the manufacturer's instructions. In orthotopic HCC mouse model, levels of serum marker alpha-fetoprotein (AFP) were determined on day 0, 6, 12, 18, 24, 30, 36, 42 and 48 using High Range AFP kit as per manufacturer's instructions.

Example 11. Mechanism of Action

Hepatocellular carcinoma (HCC) is an extremely complex multi-factorial condition associated with many confounding factors affecting disease course and patient prognosis. A broad range of mechanisms, including telomere dysfunction, activation of oncogenic pathways, abrogation of DNA damage checkpoints, activation of pro-inflammatory and metastatic pathways, and induction of the oxidative stress response. Consequently, HCC is typically associated with overexpression of receptor tyrosine kinases (RTK) and excessive oxidative stress (ROS). Collectively, overexpression of RTK and ROS lead to increased expression of c-myc, resulting in high metastatic potentials of hepatocytes. Thus, metastatic potential of hepatocytes can be reduced with specific inhibitors of RTK. On the other hand, HCC is also associated with overexpression of miR-221, miR-222 and CDKs, resulting in dysregulation of cell cycle, which leads to excessive proliferation of hepatocytes. Treatment with milciclib is known to inhibit miR-221/miR-222 and a number of CDKs and it can effectively reduce proliferation of hepatocytes. Therefore, collectively combination of milciclib with an inhibitor of RTK may produce synergistic effect in reducing expression of c-myc and in total tumor growth and progression. Thus, an effective therapy for HCC needs to control proliferation of hepatocytes and also suppress their metastatic potential. (FIG. 76)

I claim:

1. A method of treating liver cancer in a patient in need thereof, comprising administering to the patient a therapeutically effective amount of milciclib, or a pharmaceutically acceptable salt, isomer, or tautomer thereof, in combination with a therapeutically effective amount of another anticancer drug, wherein the other anticancer drug is sorafenib, lenvatinib, regorafenib, or a pharmaceutically acceptable salt thereof.

2. The method of claim 1, wherein the liver cancer is hepatocellular carcinoma.

3. The method of claim 1, wherein the other anticancer drug is sorafenib or a pharmaceutically acceptable salt thereof.

4. The method of claim 3, wherein the therapeutically effective amount of sorafenib is 400 mg twice daily, 200 mg twice daily, or 200 mg once daily.

5. The method of claim 3, wherein the cancer is hepatocellular carcinoma.

6. The method of claim 1, wherein the other anticancer drug is lenvatinib or a pharmaceutically acceptable salt thereof.

7. The method of claim 6, wherein the therapeutically effective amount of lenvatinib is 8, 10, 12, 14, 18, 20, 22, 24, 26, 28, 30, 32, or 34 mg once daily.

8. The method of claim 1, wherein the other anticancer drug is regorafenib or a pharmaceutically acceptable salt thereof.

9. The method of claim 8, wherein the therapeutically effective amount of regorafenib is 80, 100, or 120 mg once daily for three weeks, followed by one week of no administration, wherein the cycle is optionally repeated.

10. The method of claim 1, wherein the therapeutically effective amount of milciclib is 50, 75, 100, 125, or 150 mg once daily for four consecutive days, followed by non-administration for 3 consecutive days, wherein the cycle is optionally repeated.

11. The method of claim 1, wherein milciclib and the other anticancer drug are administered to the patient simultaneously.

12. The method of claim 1, wherein milciclib and the other anticancer drug are administered in a single pharmaceutical formulation that further includes a pharmaceutically acceptable excipient.

13. The method of claim 12, wherein the pharmaceutical formulation is in a controlled release form.

14. The method of claim 1, wherein milciclib and the other anticancer drug are each administered in separate pharmaceutical formulations, wherein each formulation further includes a pharmaceutically acceptable excipient.

15. The method of claim 14, wherein one or both of the pharmaceutical formulations is in a controlled release form.

16. The method of claim 1, wherein milciclib and the other anticancer drug are administered to the patient sequentially.

17. The method of claim 16, wherein administration of milciclib begins before administration of the other anticancer to the patient.

18. The method of claim 16, wherein administration of milciclib begins after administration of the other anticancer to the patient.

19. The method of claim 17, wherein milciclib is administered in a single pharmaceutical formulation that further includes a pharmaceutically acceptable excipient.

20. The method of claim 19, wherein the pharmaceutical formulation is formulated for oral administration.

21. The method of claim 20, wherein the pharmaceutical formulation is in the form of a tablet, pill, or capsule.

22. A method of treating hepatocellular carcinoma in a patient in need thereof comprising administering to the patient a therapeutically effective amount of milciclib, or a pharmaceutically acceptable salt, isomer, or tautomer thereof, in combination with a therapeutically effective amount of sorafenib, or a pharmaceutically acceptable salt, isomer, or tautomer thereof.

23. The method of claim 22, wherein the therapeutically effective amount of sorafenib is 400 mg twice daily, 200 mg twice daily, or 200 mg once daily.

24. The method of claim 22, wherein the therapeutically effective amount of milciclib is 50, 75, 100, 125, or 150 mg once daily for four consecutive days, followed by non-administration for 3 consecutive days, wherein the cycle is optionally repeated.

25. The method of claim 1, wherein milciclib and the other anticancer drug are administered in temporal proximity.

26. The method of claim 18, wherein milciclib is administered in a single pharmaceutical formulation that further includes a pharmaceutically acceptable excipient.

27. The method of claim 26, wherein the pharmaceutical formulation is formulated for oral administration.

28. The method of claim 27, wherein the pharmaceutical formulation is in the form of a tablet, pill, or capsule.

29. A method of treating hepatocellular carcinoma in a patient in need thereof, comprising administering to the patient:
   (a) 200, 400, or 800 mg/day of sorafenib; and
   (b) 50, 75, 100, 125, or 150 mg/day of milciclib.

30. The method of claim 29, wherein the milciclib is administered to the patient for four consecutive days, followed by non-administration for 3 consecutive days, wherein the cycle is optionally repeated.

* * * * *